US011331368B2

(12) United States Patent
Widdop et al.

(10) Patent No.: US 11,331,368 B2
(45) Date of Patent: May 17, 2022

(54) ANGIOTENSIN RECEPTOR AGONISTS AND USES THEREOF

(71) Applicant: Monash University, Clayton (AU)

(72) Inventors: Robert Widdop, Melbourne (AU); Marie-Isabel Aguilar, Melbourne (AU); Mark Del Borgo, Melbourne (AU); Emma Jones, Melbourne (AU); Baydaa Hirmiz, Melbourne (AU); Yan Wang, Melbourne (AU)

(73) Assignee: Monash University, Clayton (AU)

( * ) Notice: Subject to any disclaimer, the term of this patent is extended or adjusted under 35 U.S.C. 154(b) by 0 days.

(21) Appl. No.: 16/630,053

(22) PCT Filed: Jul. 17, 2018

(86) PCT No.: PCT/AU2018/050744
§ 371 (c)(1),
(2) Date: Jan. 10, 2020

(87) PCT Pub. No.: WO2019/014710
PCT Pub. Date: Jan. 24, 2019

(65) Prior Publication Data
US 2020/0222494 A1    Jul. 16, 2020

(30) Foreign Application Priority Data

Jul. 17, 2017 (AU) ............................... 2017902801

(51) Int. Cl.
*A61K 38/08* (2019.01)
*A61P 17/02* (2006.01)

(52) U.S. Cl.
CPC ............ *A61K 38/085* (2013.01); *A61P 17/02* (2018.01)

(58) Field of Classification Search
None
See application file for complete search history.

(56) References Cited

FOREIGN PATENT DOCUMENTS

| WO | WO 00/53211 | * | 9/2000 |
|---|---|---|---|
| WO | WO 2000/056345 A2 | | 9/2000 |
| WO | WO 2013/090833 A1 | | 6/2013 |
| WO | WO 2016/139475 A1 | | 9/2016 |
| WO | WO 2017/015720 | * | 2/2017 |
| WO | WO 2017/015720 A1 | | 2/2017 |

OTHER PUBLICATIONS

Jones et al. (Hypertension. 2011;57[part 2]:570-576) (Year: 2011).*
Panos et al. (Am J Med. Apr. 1990;88(4):396-404) (Year: 1990).*
Leslie, Science Now, May 2012 (Year: 2012).*
PubChem (CID44365220, Nov. 19, 2009) (Year: 2009).*
Del Borgo et al. (Clinical Science (2015) 129, 505-513) (Year: 2015).*
Bosnyak, S. et al. "Relative affinity of angiotensin peptides and novel ligands at AT1 and AT2 receptors." Clinical Science, 2011, vol. 121, No. 7, p. 297-303.
Bruce, E. et al. "Selective activation of angiotensin AT2 receptors attenuates progression of pulmonary hypertension and inhibits cardiopulmonary fibrosis." Br J Pharmacol, 2015, vol. 172, No. 9, p. 2219-2231.
Chow, B.S., et al. "The angiotensin 11 type 2 receptor agonist Compound 21 is protective in experimental diabetes-associated atherosclerosis." Diabetologia, 2016, vol. 59, No. 8, p. 1778-1790.
Clayton, D. et al. "Beta-Amino acid substitution to investigate the recognition of angiotensin II (AngII) by angiotensin converting enzyme 2 (ACE2)" J Mol Recognit., 2011, vol. 24, No. 2, p. 235-244.
Del Borgo M., et al. "(b-Pro7Ang III is a novel highly selective angiotensin II type 2 receptor (AT2R) agonist, which acts as a vasodepressor agent via the AT2R in conscious spontaneously hypertensive rats" Clin Sci (Lond), 2015, vol. 129, No. 6, p. 505-513.
Jones, E.S. et al. "A single beta-amino acid substitution to angiotensin 11 confers AT2 receptor selectivity and vascular function" Hypertension, 2011, vol. 57, No. 3, p. 570-576.
Barber, Melissa N., Donella B. Sampey, and Robert E. Widdop. "AT2 receptor stimulation enhances antihypertensive effect of AT1 receptor antagonist in hypertensive rats." *Hypertension* 34.5 (1999): 1112-1116.
Hallberg, Anders, Mathias Hallberg, and Jonas Savmarker. "Angiotensin peptides as AT2 receptor agonists." *Current Protein and Peptide Science* 18.8 (2017): 809-818.
Hansen, Jakob Lerche, et al. "Functional reconstitution of the angiotensin II type 2 receptor and Gi activation." *Circulation research* 87.9 (2000): 753-759.
Matsoukas, John M., et al. "Synthesis and biological activities of analogs of angiotensins II and III containing O-methyltyrosine and D-tryptophan." *Journal of medicinal chemistry* 28.6 (1985): 780-783.

(Continued)

*Primary Examiner* — Sergio Coffa
(74) *Attorney, Agent, or Firm* — Frost Brown Todd LLC; Nicole M. Tepe

(57) ABSTRACT

The present invention relates to compositions, methods and kits for the treatment of fibrosis. In particular, the compositions, methods and kits are particularly useful, but not limited to, the treatment of cardiac fibrosis. The invention provides a method of treating fibrosis in an individual comprising administering an AT2R selective agonist, thereby treating fibrosis.

17 Claims, 47 Drawing Sheets
Specification includes a Sequence Listing.

(56) References Cited

OTHER PUBLICATIONS

Rompe, Franziska, et al. "Direct angiotensin II type 2 receptor stimulation acts antiinflammatory through epoxyeicosatrienoic acid and inhibition of nuclear factor κB." *Hypertension* 55.4 (2010): 924-931.

Servant, G., et al. "Photoaffinity labeling of subtype 2 angiotensin receptor of human myometrium." *Molecular pharmacology* 43.5 (1993): 677-683.

Stoddart, Leigh A., et al. "Application of BRET to monitor ligand binding to GPCRs." *Nature methods* 12.7 (2015): 661-663.

Tsuzuki, Satoshi, et al. "Angiotensin II type 2 receptor inhibits cell proliferation and activates tyrosine phosphatase." *Hypertension* 28.5 (1996): 916-918.

Wang, Yan, et al. "Novel AT2 Receptor Agonists are Cardio-and Reno-Protective In Vitro and In Vivo." *Hypertension* 74. Suppl_1 (2019): A101-A101.

Wang (2018) High Blood Pressure Research Council of Australia: Joint HBPRCA, AAS and AVBS Meeting, South Australia, Nov. 27-30, 2018; A132.

Whitebread, Steven, et al. "Preliminary biochemical characterization of two angiotensin II receptor subtypes." *Biochemical and biophysical research communications* 163.1 (1989): 284-291.

Whitebread, Steven E., et al. "Radioiodinated CGP 42111 A: A novel high affinity and highly selective ligand for the characterization of angiotensin AT2 receptors." *Biochemical and biophysical research communications* 181.3 (1991): 1365-1371.

Widdop, Robert E., et al. "AT2 receptor-mediated relaxation is preserved after long-term AT1 receptor blockade." *Hypertension* 40.4 (2002): 516-520.

Widdop, Robert E., et al. "Angiotensin AT2 receptors: cardiovascular hope or hype?" *British journal of pharmacology* 140.5 (2003): 809-824.

Extended European Search Report dated Mar. 10, 2021, for Application No. 18835864.2, 14 pages.

International Search Report and Written Opinion dated Sep. 28, 2018, for International Application No. PCT/AU2018/050744, 18 pages.

* cited by examiner

AT$_2$R-mediated vasorelaxation (mouse aortae)

ANGIOTENSIN RECEPTOR AGONISTS AND USES THEREOF

CROSS-REFERENCE TO RELATED APPLICATIONS

This application is a national stage application, filed under 35 U.S.C. 371, of International Application No. PCT/AU2018/050744, filed on Jul. 17, 2018, which claims priority from, and benefit of Australian provisional application No. AU 2017902801, filed Jul. 17, 2017. The entire contents of each of the aforementioned patent applications are incorporated herein by reference in their entireties.

INCORPORATION-BY-REFERENCE OF SEQUENCE LISTING

The contents of the file named "53061919_ST25_UpdatedSequenceListing_April2021.TXT", which was created on Apr. 6, 2021, and is 4,981 bytes in size are hereby incorporated by reference in their entirety.

FIELD OF THE INVENTION

The present invention relates to compounds, compositions, methods and kits for the treatment of fibrosis. In particular, the compounds, compositions, methods and kits are particularly useful, but not limited to, the treatment of organ fibrosis.

BACKGROUND OF THE INVENTION

Fibrosis, or scarring, is a natural consequence of certain types of injury and inflammation and is characterized by abnormal and excessive deposition of collagen and other extracellular matrix (ECM) components in various tissues. Fibrosis can occur in various tissues, such as the heart, lungs, liver, skin, blood vessels and kidneys.

Cardiovascular diseases (CVDs) remain the world's leading cause of morbidity and mortality, claiming 17 million deaths annually, accounting for 1 death every 2s worldwide. Importantly, prevalence of major CVDs increases exponentially after the age of 60, with aged patients often suffering from cardiac dysfunction or chronic heart failure (CHF). CVDs are often initiated upon any cardiac insult or injury, which then triggers the innate defense mechanism and inflammatory response to counter-regulate and repair the injury, in a process known as cardiac remodeling. However, repetitive injury or dysregulated reactive remodeling eventually leads to accumulation of excessive collagens in the heart, driving towards a progressively irreversible fibrotic response, leading to permanent scarring or cardiac fibrosis. Subsequently, blood supply to the heart is impaired, while increased stiffness of the heart further hinders cardiac contractility which predisposes to myocardial infarction (MI), chronic heart failure (CHF) or end organ damage. Such events are more likely to occur in the aging population, thus further increasing the susceptibility towards myocardial infarction or injury, with ageing itself compromised by the inefficient reparative process. Moreover, there are few treatments available which are directed against fibrosis. Of these, angiotensin converting enzyme (ACE) inhibitor or angiotensin receptor blockers (ARBs) only reduced CV mortality rate by ~7% on top of standard treatment.

There is a need for new or improved therapies for the treatment and/or prevention of fibrosis.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention provides a method of treating fibrosis in an individual comprising administering a compound that has greater than about 100-fold selectivity for the Angiotensin II Receptor Type 2 (AT2R) than for the Angiotensin II Receptor Type 1 (AT1R) to the individual, thereby treating fibrosis in the individual.

In any method or use of the invention, the compound has greater than about 110, 120, 130, 140, 150, 160, 170, 180, 190, 200, 300, 400, 500, 600, 700, 800, 9000, 1000, 5000, 10000, 20000, 50000 or 100000 fold selectivity for the AT2R than the AT1R.

In any method or use of the invention, the compound is an AT2R agonist.

In any method or use of the invention, the compound is a peptide. Preferably the peptide comprises, consists essentially of, or consists of an amino acid sequence having at least about 60%, 70%, 75%, 80%, 85%, 90%, 91%, 92%, 93%, 94%, 95%, 96%, 97%, 98%, 99% or 100% identity to an angiotensin peptide. The angiotensin peptide may be angiotensin II (Ang II), angiotensin III (Ang III) or angiotensin IV (Ang IV).

In any method or use of the invention, the peptide comprises, consists essentially of, or consists of an amino acid sequence of the formula:

(SEQ ID NO: 1)
$Xaa_1$-$Xaa_2$-Val-Tyr-Ile-$Xaa_6$-Pro-$Xaa_8$ wherein $Xaa_1$ is a polar or hydrophilic amino acid (preferably Asp or a conservative substitution thereof such as Lys, His, Arg, Glu, Gln, Ser or Thr), absent, or a D-amino acid (preferably a D-amino acid of a polar or hydrophilic amino acid);

wherein $Xaa_2$ is a positively charged amino acid (preferably Arg or conservative substitution thereof such as Lys or His), absent, or a D-amino acid (preferably a D-amino acid of a positively charged amino acid such as D-Asp or D-Arg);

wherein $Xaa_6$ is His, Tyr, or a conservative substitution thereof (such as Lys); and wherein $Xaa_8$ is an aromatic ring containing amino acid (preferably Phe, Trp, or a conservative substitution thereof), a heterocyclic containing amino acid, Ala, Ile, or a conservative substitution thereof.

Preferably one or more amino acids are in beta (for example, $\beta^2$ or $\beta^3$) form, for example βArg, βVal, βTyr, β-Ile, βHis, βPro, βAla, βTrp, or βPhe. More preferably, where the amino acid is Proline, it is βhomoPro.

In certain methods or uses of the invention, $Xaa_1$ may be absent or both $Xaa_1$ and $Xaa_2$ may be absent from the peptide (meaning that there is no amino acid at this position in the peptide).

Alternatively, any one, any two or any three of $Xaa_1$, $Xaa_2$ or $Xaa_8$ may be glycine residues.

Further, the peptide may be modified at the N-terminus. Preferably, the modification increases the plasma stability of the peptide, for example by reducing or inhibiting degradation by aminopeptidases. More preferably the modification is selected from: acetylation, N-terminal pyroglutamate, a non-natural amino acid substitution, PEGylation, lipidation, glycosylation, N-methylation. The modification may be an addition to the N-terminus of the peptide, including conjugation to vitamins or bile acids (including Nicotinamide conjugation), capping with imidazole carboxylate or tetrazole carboxylate or where the N-acyl cap (designated herein as N—Ac—) can be selected from; —$C_{1-6}$ alkyl, optionally substituted —$C_{1-6}$ haloalkyl, optionally substituted —$C_{2-6}$ alkenyl, optionally substituted —$C_{3-6}$ cycloalkyl, optionally substituted phenyl, optionally substituted —$C_{1-3}$ alkyl, —$C_{3-6}$ cycloalkyl and optionally substituted —$C_{1-3}$ alkylphenyl and any other N-terminal modification as described herein.

Accordingly, in any method or use of the invention, the peptide comprises, consists essentially of, or consists of any one of the following amino acid sequences:

Asp-Arg-Val-Tyr-Ile-His-Pro-Xaa$_8$ (SEQ ID NO: 2), i.e., wherein Xaa$_1$ is Asp, Xaa$_2$ is Arg and Xaa$_6$ is His, according to the formula described above, and wherein Xaa$_8$ is any amino acid, preferably an aromatic hydrophobic amino acid or an aliphatic hydrophobic amino acid;

Arg-Val-Tyr-Ile-His-Pro-Xaa$_8$ (SEQ ID NO: 3), i.e., wherein Xaa$_1$ is absent, Xaa$_2$ is Arg and Xaa$_6$ is His, according to the formula described above, and wherein Xaa$_8$ is any amino acid, preferably an aromatic hydrophobic amino acid or an aliphatic hydrophobic amino acid; and Val-Tyr-Ile-His-Pro-Xaa$_8$ (SEQ ID NO: 4), i.e., wherein Xaa$_1$ and Xaa$_2$ are both absent and Xaa$_6$ is His, according to the formula described above, and wherein Xaa$_8$ is any amino acid, preferably an aromatic hydrophobic amino acid or an aliphatic hydrophobic amino acid. The amino acid of one or more residues may be in beta (for example, $\beta^2$ or $\beta^3$) form for example βArg, βVal, βTyr, βIle, βHis, βPro, βAla, βTrp, or βPhe. The N-terminal amino acid may be a D-amino acid (for example, D-Asp, D-Arg).

Further, the peptide may be modified at the N-terminus. Preferably, the modification reduces or inhibits degradation by aminopeptidases. More preferably the modification is selected from, acetylation, N-terminal pyroglutamate, a non-natural amino acid substitution, PEGylation, lipidation, glycosylation, N-methylation. The modification may be an addition to the N-terminus of the peptide, including conjugation to vitamins or bile acids (including Nicotinamide conjugation), capping with imidazole carboxylate or tetrazole carboxylate or where the N-acyl cap (designated herein as N—Ac—) can be selected from; —$C_{1-6}$ alkyl, optionally substituted —$C_{1-6}$ haloalkyl, optionally substituted —$C_{2-6}$ alkenyl, optionally substituted —$C_{3-6}$ cycloalkyl, optionally substituted phenyl, optionally substituted —$C_{1-3}$ alkyl, —$C_{3-6}$ cycloalkyl and optionally substituted —$C_{1-3}$ alkylphenyl and any other N-terminal modification as described herein. Preferably, the peptide comprises, consists essentially of, or consists of any one of the following amino acid sequences:

Asp-Arg-Val-Tyr-Ile-His-Pro-Xaa$_8$ (SEQ ID NO: 2), i.e., wherein Xaa$_1$ is Asp, Xaa$_2$ is Arg and Xaa$_6$ is His, according to the formula described above, and wherein Xaa$_8$ is Phe, Ile, Trp or Ala;

Arg-Val-Tyr-Ile-His-Pro-Xaa$_8$ (SEQ ID NO: 3), i.e., wherein Xaa$_1$ is absent, Xaa$_2$ is Arg and Xaa$_6$ is His, according to the formula described above, and wherein Xaa$_8$ is Phe, Ile, Trp or Ala; or Val-Tyr-Ile-His-Pro-Xaa$_8$ (SEQ ID NO:4), i.e., wherein Xaa$_1$ and Xaa$_2$ are both absent and Xaa$_6$ is His, according to the formula described above, and wherein Xaa$_8$ is Phe, Ile, Trp or Ala. The amino acid of one or more residues may be in beta (for example, $\beta^2$ or $\beta^3$) form for example βArg, βVal, βTyr, βIle, βHis, βPro, βAla, βTrp, or βPhe. The N-terminal amino acid may be a D-amino acid (for example, D-Asp, D-Arg). Further, the peptides may be modified at the N-terminus. Preferably, the modification is acetylation, N-terminal pyroglutamate, a non-natural amino acid substitution, PEGylation, lipidation, glycosylation, N-methylation. The modification may be an addition to the N-terminus of the peptide, including conjugation to vitamins or bile acids (including Nicotinamide conjugation), capping with imidazole carboxylate or tetrazole carboxylate or where the N-acyl cap (designated herein as N—Ac—) can be selected from; —$C_{1-6}$ alkyl, optionally substituted —$C_{1-6}$ haloalkyl, optionally substituted —$C_{2-6}$ alkenyl, optionally substituted —$C_{3-6}$ cycloalkyl, optionally substituted phenyl, optionally substituted —$C_{1-3}$ alkyl, —$C_{3-6}$ cycloalkyl and optionally substituted —$C_{1-3}$ alkylphenyl and any other N-terminal modification as described herein.

Further, the peptide comprises, consists essentially of, or consists of the following amino acid sequences:

Xaa$_1$-Xaa$_2$-Val-Tyr-Ile-His-Pro-Xaa$_8$ (SEQ ID NO: 20), i.e., wherein Xaa$_1$ is Gly or is absent, Xaa$_2$ is Gly or Arg or is absent, Xaa$_6$ is His, according to the formula described above, and wherein Xaa$_8$ is Gly, Phe, Ile, Trp or Ala. The amino acid of one or more residues may be in beta (for example, $\beta^2$ or $\beta^3$) form, for example βArg, βVal, βTyr, βIle, βHis, βPro, βAla, βTrp, or βPhe. The N-terminal amino acid may be a D-amino acid (for example, D-Asp, D-Arg). Further, the peptides may be modified at the N-terminus. Preferably, the modification is acetylation, N-terminal pyroglutamate, a non-natural amino acid substitution, PEGylation, lipidation, glycosylation, N-methylation. The modification may be an addition to the N-terminus of the peptide, including conjugation to vitamins or bile acids (including Nicotinamide conjugation), capping with imidazole carboxylate or tetrazole carboxylate or where the N-acyl cap (designated herein as N—Ac—) can be selected from; —$C_{1-6}$ alkyl, optionally substituted —$C_{1-6}$ haloalkyl, optionally substituted —$C_{2-6}$ alkenyl, optionally substituted —$C_{3-6}$ cycloalkyl, optionally substituted phenyl, optionally substituted —$C_{1-3}$ alkyl, —$C_{3-6}$ cycloalkyl and optionally substituted —$C_{1-3}$ alkylphenyl and any other N-terminal modification as described herein.

In any aspect of the invention, the peptide comprises, consists essentially of, or consists of any one of the following amino acid sequences:

```
                                            (SEQ ID NO: 5)
Asp-βArg-Val-Tyr-Ile-His-Pro-Phe;

(SEQ ID NO: 5)
Asp-Arg-Val-βTyr-Ile-His-Pro-Phe;

(SEQ ID NO: 5)
Asp-Arg-Val-Tyr-βIle-His-Pro-Phe;

(SEQ ID NO: 5)
Asp-Arg-Val-Tyr-Ile-His-βPro-Phe;

(SEQ ID NO: 6)
Arg-Val-βTyr-Ile-His-Pro-Phe;

(SEQ ID NO: 6)
Arg-Val-Tyr-Ile-His-βPro-Phe;

(SEQ ID NO: 6)
Arg-Val-Tyr-Ile-His-Pro-βPhe;
```

```
                                    (SEQ ID NO: 7)
Val-Tyr-Ile-His-βPro-Phe;

(SEQ ID NO: 8)
Asp-Arg-Val-Tyr-βIle-His-Pro-Ile;

(SEQ ID NO: 8)
Asp-Arg-Val-Tyr-Ile-His-Pro-βIle;

(SEQ ID NO: 9)
Arg-Val-Tyr-βIle-His-Pro-Ile;

(SEQ ID NO: 9)
Arg-Val-Tyr-Ile-His-βPro-Ile;

(SEQ ID NO: 9)
Arg-Val-Tyr-Ile-His-Pro-βIle;

(SEQ ID NO: 5)
D-Asp-Arg-Val-Tyr-βIle-His-Pro-Phe;

(SEQ ID NO: 6)
D-Arg-Val-Tyr-Ile-His-Pro-Phe;

(SEQ ID NO: 6)
D-Arg-Val-Tyr-βIle-His-Pro-Phe;

(SEQ ID NO: 6)
D-Arg-Val-Tyr-Ile-His-βPro-Phe;

(SEQ ID NO: 10)
D-Arg-Val-Tyr-Ile-His-βPro-Trp;

(SEQ ID NO: 6)
N-Ac-Arg-Val-Tyr-Ile-His-βPro-Phe;

(SEQ ID NO: 10)
N-Ac-Arg-Val-Tyr-Ile-His-βPro-Trp;

(SEQ ID NO: 11)
Asp-βArg-Val-Tyr-Ile-His-Pro-Ala;

(SEQ ID NO: 11)
Asp-Arg-βVal-Tyr-Ile-His-Pro-Ala;

(SEQ ID NO: 11)
Asp-Arg-Val-βTyr-Ile-His-Pro-Ala;

(SEQ ID NO: 11)
Asp-Arg-Val-Tyr-βIle-His-Pro-Ala;

(SEQ ID NO: 11)
Asp-Arg-Val-Tyr-Ile-His-βPro-Ala;

(SEQ ID NO: 12)
βArg-Val-Tyr-Ile-His-Pro-Ala;

(SEQ ID NO: 12)
Arg-βVal-Tyr-Ile-His-Pro-Ala;

(SEQ ID NO: 12)
Arg-Val-βTyr-Ile-His-Pro-Ala;

(SEQ ID NO: 12)
Arg-Val-Tyr-βIle-His-Pro-Ala;

(SEQ ID NO: 12)
Arg-Val-Tyr-Ile-His-βPro-Ala;

(SEQ ID NO: 10)
βArg-Val-Tyr-Ile-His-Pro-Trp;

(SEQ ID NO: 10)
Arg-βVal-Tyr-Ile-His-Pro-Trp;

(SEQ ID NO: 10)
Arg-Val-βTyr-Ile-His-Pro-Trp;

(SEQ ID NO: 10)
Arg-Val-Tyr-βIle-His-Pro-Trp;

(SEQ ID NO: 10)
Arg-Val-Tyr-Ile-His-βPro-Trp;

(SEQ ID NO: 10)
Arg-Val-Tyr-Ile-His-Pro-βTrp;

(SEQ ID NO: 13)
Val-Tyr-Ile-Tyr-βPro-Trp;

(SEQ ID NO: 14)
Val-Tyr-Ile-His-βPro-Trp;

(SEQ ID NO: 15)
Arg-Val-Tyr-Ile-Tyr-βPro-Trp;

(SEQ ID NO: 15)
Arg-Val-Tyr-Ile-βTyr-Pro-Trp;

(SEQ ID NO: 16)
Asp-Arg-Val-Tyr-Ile-Tyr-βPro-Trp;

(SEQ ID NO: 16)
Asp-Arg-Val-Tyr-Ile-βTyr-Pro-Trp;

(SEQ ID NO: 17)
Val-Tyr-Ile-Tyr-βPro-Phe;

(SEQ ID NO: 18)
Arg-Val-Tyr-Ile-Tyr-βPro-Phe;

(SEQ ID NO: 18)
Arg-Val-Tyr-Ile-βTyr-Pro-Phe;

(SEQ ID NO: 19)
Asp-Arg-Val-Tyr-Ile-Tyr-βPro-Phe;

(SEQ ID NO: 19)
Asp-Arg-Val-Tyr-Ile-βTyr-Pro-Phe;

(SEQ ID NO: 15)
Tetrazole-CONH-Arg-Val-Tyr-Ile-Tyr-βPro-Trp;

(SEQ ID NO: 18)
Tetrazole-CONH-Arg-Val-Tyr-Ile-Tyr-βPro-Phe;

(SEQ ID NO: 18)
Nicotinamido- Arg-Val-Tyr-Ile-Tyr-βPro-Phe;

(SEQ ID NO: 15)
Nicotinamido- Arg-Val-Tyr-Ile-Tyr-βPro-Trp;

(SEQ ID NO: 15)
Cholate- Arg-Val-Tyr-Ile-Tyr-βPro-Trp;

(SEQ ID NO: 18)
Cholate- Arg-Val-Tyr-Ile-Tyr-βPro-Phe;

(SEQ ID NO: 15)
Deoxycholate- Arg-Val-Tyr-Ile-Tyr-βPro-Trp;

(SEQ ID NO: 18)
Deoxycholate- Arg-Val-Tyr-Ile-Tyr-βPro-Phe;

(SEQ ID NO: 15)
Ursodeoxycholate- Arg-Val-Tyr-Ile-Tyr-βPro-Trp;

(SEQ ID NO: 18)
Ursodeoxycholate- Arg-Val-Tyr-Ile-Tyr-βPro-Phe;

(SEQ ID NO: 15)
Obeticholate- Arg-Val-Tyr-Ile-Tyr-βPro-Trp;
or (SEQ ID NO: 18)
Obeticholate- Arg-Val-Tyr-Ile-Tyr-βPro-Phe.
```

In a preferred embodiment, the present invention provides a method of treating fibrosis in an individual comprising administering a therapeutically effective amount of a peptide comprising or consisting of the sequence Arg-Val-Tyr-Ile-His-Pro-Trp (SEQ ID NO: 10), thereby treating fibrosis in the individual.

Preferably, one or more amino acid residues of the Arg-Val-Tyr-Ile-His-Pro-Trp (SEQ ID NO: 10) peptide are in β form (including β² or β³ forms), more preferably, wherein the Proline residue at position $Xaa_7$ is βPro, even more preferably, βhomoPro.

In one embodiment, the N-terminal amino acid residue of the peptide is a D-amino acid. In a further embodiment, the N-terminal amino acid residue of the Arg-Val-Tyr-Ile-His-Pro-Trp (SEQ ID NO: 10) peptide may be modified. Any N-terminal modification as described herein may be used, including acetylation, N-terminal pyroglutamate, a non-natural amino acid substitution, PEGylation, lipidation, glycosylation and N-methylation. In one embodiment, the N-terminal modification is acetylation (i.e., an N—Ac cap).

In one embodiment, the present invention provides a method of treating fibrosis in an individual comprising administering a therapeutically effective amount of a peptide comprising or consisting of the sequence D-Arg-Val-Tyr-Ile-His-βPro-Trp (SEQ ID NO: 10), thereby treating fibrosis in the individual.

In an alternative embodiment, the present invention provides a method of treating fibrosis in an individual comprising administering a therapeutically effective amount of a peptide comprising or consisting of the sequence N—Ac-Arg-Val-Tyr-Ile-His-βPro-Trp (SEQ ID NO: 10), thereby treating fibrosis in the individual.

Preferably, the peptide exhibits an $IC_{50}$ for the AT2R of less than about 100 nM, 50 nM, 20 nM, 10 nM, 9 nM, 8 nM, 7 nM, 6 nM, 5 nM, 4 nM, 3 nM, 2 nM, 1 nM. The $IC_{50}$ may be measured using any method as described herein, preferably the radioligand binding assay as described in Example 2.

Preferably, the peptide exhibits an $IC_{50}$ for the AT1R of greater than 100 nM, 200 nM, 300 nM, 400 nM, 500 nM, 600 nM, 700 nM, 800 nM, 1 µM, 10 µM, or 50 µM. The $IC_{50}$ may be measured using any method as described herein, preferably the radioligand binding assay as described in Example 2.

Preferably, an assay that determines the relative selectivity of a compound at AT2R compared to AT1R will involve using an iodinated version of Angiotensin II as a nonselective compound (such as $^{125}$I-AngII or $^{125}$I-Sar$^1$-Ile$^8$-AngII) that is able to bind both AT1Rs and AT2Rs using cells transfected with either human AT1Rs or human AT2Rs (such as HEK-293 cells or other cell lines), or using native tissue or cells that naturally express these AT1Rs and AT2R sub-types (either human or rodent). Typically, the ability of compounds of interest to displace the Ang II radioligand from both AT1Rs and AT2Rs will be determined. This will lead to the generation of $IC_{50}$ values that determine the relative ability of test compounds to interact with both receptors.

Preferably, the peptide reverses or prevents at least one biochemically observable characteristic of fibrosis selected from increases in the TGF-β signalling pathway, increases in the expression of α-SMA, increases in macrophage infiltration, increases in NF-kβ expression, increases in TGF-R protein expression, increases in tubulointerstitial fibrosis or increases in liver steatosis.

In any aspect of the present invention, the method or use reduces progression of at least one clinically or biochemically observable characteristic of fibrosis, thereby treating fibrosis.

In any aspect of the present invention, the method or use reverses at least one clinically or biochemically observable characteristic of fibrosis, thereby treating fibrosis. The clinically or biochemically observable characteristic may be any one or more of the following organ dysfunction, scarring, alteration of normal extracellular matrix balance, increase in collagen deposition, differentiation of fibroblasts to myofibroblasts, reduction in the level of matrix metalloproteinases and increase in the level of tissue Inhibitors of matrix metalloproteinases. Preferably, collagen is a precursor or mature forms of collagen al Type 1. A biochemically observable characteristic is selected from increases in the TGF-β signalling pathway, increases in the expression of α-SMA, increases in macrophage infiltration, increases in NF-kβ expression, increases in TGF-protein expression, increases in tubulointerstitial fibrosis or in increases in liver steatosis. Preferably the effect on any one or more of the above-mentioned clinical or biochemically observable characteristics is equal to, or significantly more, than the effect of candesartan or captopril.

In any aspect of the invention, the fibrosis may be age-induced, injury-induced, stress-induced or diet-induced (such as high salt diet) or hypertension-induced. Preferably, the fibrosis is selected from the group consisting of cardiac fibrosis, liver fibrosis, kidney fibrosis, vascular fibrosis, lung fibrosis and dermal fibrosis.

In any method of the invention, the method further comprises the step of identifying an individual having fibrosis.

The invention also provides a method of alleviating or ameliorating a symptom of fibrosis in a subject in need thereof, the method comprising administering to the subject in need thereof a therapeutically effective amount of a compound, preferably a peptide, that has greater than about 100-fold selectivity for the AT2R than the AT1R as described herein, thereby alleviating or ameliorating a symptom of fibrosis in the subject. Preferably, the fibrosis is age-induced, as a result of underlying tissue injury or related to hypertension or other cardiovascular disease.

The invention also provides use of a compound, preferably a peptide, that has greater than about 100-fold selectivity for the AT2R than the AT1R as described herein in the manufacture of a medicament for the treatment or prevention of fibrosis in a subject in need thereof.

The present invention provides a method for the treatment of fibrosis in a subject comprising the steps of identifying a subject having fibrosis; and administering to the subject in need thereof a therapeutically effective amount of a compound, preferably a peptide, that has greater than about 100-fold selectivity for the AT2R than the AT1R as described herein, thereby treating fibrosis in the subject.

The invention has particular application to a subject having any one or more of the following detectable symptoms including organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP), decreased levels of C-terminal telepeptide of Type I collagen (CTP or CITP), increased collagen deposition and impaired cardiac function measured by various non-invasive imagining techniques, and impaired renal function as measured by increased proteinurea and albuminurea, decreased glomerular filtration rate or doubling of creatinine levels or altered liver enzymes alanine transaminase (ALT) or aspartate transaminase (AST).

The present invention provides a method for the treatment of age-induced fibrosis, organ fibrosis related to tissue injury, or hypertension-induced fibrosis, the method comprising the steps of identifying a subject having age-induced fibrosis, organ fibrosis related to tissue injury, or hypertension-induced fibrosis; and administering to the subject in need thereof a therapeutically effective amount of a peptide that has greater than about 100-fold selectivity for the AT2R than the AT1R as described herein, thereby treating age-induced fibrosis, organ fibrosis related to tissue injury or hypertension-induced fibrosis.

In any aspect or embodiment of the invention, age-induced fibrosis or hypertension-induced may be reference to age-induced fibrosis of the heart (cardiac), kidney (renal), blood vessels (vascular), liver (hepatic), pancreas and lung (pulmonary).

The present invention also provides a method for treating steatosis in an individual comprising administering a peptide that has greater than about 100-fold selectivity for the AT2R than the AT1R, thereby treating steatosis. Preferably, the steatosis is liver steatosis.

The present invention provides a method for the treatment or prevention of fibrosis, the method comprising the step of administering a composition to the subject for treatment or prevention, wherein the composition comprises, consists essentially of or consists of a peptide that has greater than about 100-fold selectivity for the AT2R than the AT1R and a pharmaceutically acceptable diluent, excipient or carrier.

In any method or use of the invention described herein, a peptide that has greater than about 100-fold selectivity for the AT2R than the AT1R may be administered systemically or directly to the site of disease. The peptide may be formulated for oral administration.

The present invention also provides a peptide that exhibits greater than about 100-fold selectivity for the AT2R than the AT1R. Preferably, the peptide is an AT2R agonist. Preferably the peptide comprises, consists essentially of or consists of any one of the following amino acid sequences:

Asp-Arg-Val-Tyr-Ile-His-Pro-Xaa$_8$ (SEQ ID NO: 2), i.e., wherein Xaa$_1$ is Asp, Xaa$_2$ is Arg and Xaa$_6$ is His, according to the formula described above, and wherein Xaa$_8$ is Ile, Trp or Ala;

Arg-Val-Tyr-Ile-His-Pro-Xaa$_8$ (SEQ ID NO: 3), i.e., wherein Xaa$_1$ is absent, Xaa$_2$ is Arg and Xaa$_6$ is His, according to the formula described above, and wherein Xaa$_8$ is Ile, Trp or Ala; and Val-Tyr-Ile-His-Pro-Xaa$_8$ (SEQ ID NO: 4), i.e., wherein Xaa$_1$ and Xaa$_2$ are both absent and Xaa$_6$ is His, according to the formula described above, and wherein Xaa$_8$ is Ile, Trp or Ala.

The amino acid of one or more residues may be in beta (for example, $\beta^2$ or $\beta^3$) form, for example βArg, βVal, βTyr, β-Ile, βHis, βPro, βAla, βTrp, or βPhe. More preferably, where the amino acid is Proline, it is βhomoPro.

The present invention also provides a peptide that exhibits greater than about 100-fold selectivity for the AT2R than the AT1R. Preferably, the peptide is an AT2R agonist. Preferably, the peptide comprises, consists essentially of or consists of any one of the following amino acid sequences:

Asp-Arg-Val-Tyr-Ile-His-Pro-Xaa$_8$ (SEQ ID NO: 2), i.e., wherein Xaa$_1$ is Asp, Xaa$_2$ is Arg and Xaa$_6$ is His, according to the formula described above, and wherein Xaa$_8$ is Phe, Ile, Trp or Ala;

Arg-Val-Tyr-Ile-His-Pro-Xaa$_8$ (SEQ ID NO: 3), i.e., wherein Xaa$_1$ is absent, Xaa$_2$ is Arg and Xaa$_6$ is His, according to the formula described above, and wherein Xaa$_8$ is Phe, Ile, Trp or Ala; and Val-Tyr-Ile-His-Pro-Xaa$_8$ (SEQ ID NO: 4), i.e., wherein Xaa$_1$ and Xaa$_2$ are both absent and Xaa$_6$ is His, according to the formula described above, and wherein Xaa$_8$ is Phe, Ile, Trp or Ala. Preferably the amino acid of one or more residues is in beta (for example, $\beta^2$ or $\beta^3$) form, for example βAsp, βArg, βVal, βTyr, βIle, βHis, βPro, βAla, βTrp, or βPhe, the N-terminal amino acid is a D-amino acid (for example, D-Asp or D-Arg), and/or the peptide is modified at the N-terminus. Preferably, the modification reduces or inhibits degradation by aminopeptidases. More preferably the modification is selected from, acetylation, N-terminal pyroglutamate, a non-natural amino acid substitution, PEGylation, lipidation, glycosylation, N-methylation. The modification may be an addition to the N-terminus of the peptide, including conjugation to vitamins or bile acids (including Nicotinamide conjugation), capping with imidazole carboxylate or tetrazole carboxylate or where the N-acyl cap (designated herein as N—Ac—) can be selected from; —C$_{1-6}$ alkyl, optionally substituted —C$_{1-6}$ haloalkyl, optionally substituted —C$_{2-6}$ alkenyl, optionally substituted —C$_{3-6}$ cycloalkyl, optionally substituted phenyl, optionally substituted —C$_{1-3}$ alkyl, —C$_{3-6}$ cycloalkyl and optionally substituted —C$_{1-3}$ alkylphenyl and any other N-terminal modification as described herein.

Further, the present invention also provides a peptide that exhibits greater than about 100-fold selectivity for the AT2R than the AT1R. Preferably the peptide is an AT2R agonist. Preferably the peptide comprises, consists essentially of, or consists of the following amino acid sequences:

Xaa$_1$-Xaa$_2$-Val-Tyr-Ile-His-Pro-Xaa$_8$ (SEQ ID NO:20), i.e., wherein Xaa$_1$ is Gly or is absent, Xaa$_2$ is Arg or Gly or is absent, and Xaa$_6$ is His, according to the formula described above, and wherein Xaa$_8$ is Gly, Phe, Ile, Trp or Ala. The amino acid of one or more residues may be in beta (for example, $\beta^2$ or $\beta^3$) form for example βArg, βVal, βTyr, βIle, βHis, βPro, βAla, βTrp, or βPhe, The N-terminal amino acid may be a D-amino acid (for example, D-Asp or D-Arg). Further, the peptide may be modified at the N-terminus. Preferably, the modification is acetylation, N-terminal pyroglutamate, a non-natural amino acid substitution, PEGylation, lipidation, glycosylation, N-methylation. The modification may be an addition to the N-terminus of the peptide, including conjugation to vitamins or bile acids (including Nicotinamide conjugation), capping with imidazole carboxylate or tetrazole carboxylate or where the N-acyl cap (designated herein as N—Ac—) can be selected from; —C$_{1-6}$ alkyl, optionally substituted —C$_{1-6}$ haloalkyl, optionally substituted —C$_{2-6}$ alkenyl, optionally substituted —C$_{3-6}$ cycloalkyl, optionally substituted phenyl, optionally substituted —C$_{1-3}$ alkyl, —C$_{3-6}$ cycloalkyl and optionally substituted —C$_{1-3}$ alkylphenyl and any other N-terminal modification as described herein.

The present invention also provides a peptide that exhibits greater than about 100-fold selectivity for the AT2R than the AT1R, wherein the peptide comprises, consists essentially of or consists of any one of the following amino acid sequences:

(SEQ ID NO: 7)
Val-Tyr-Ile-His-βPro-Phe;

Asp-Arg-Val-Tyr-βIle-His-Pro-Ile; (SEQ ID NO: 5)

Asp-Arg-Val-Tyr-Ile-His-Pro-βIle; (SEQ ID NO: 5)

Arg-Val-Tyr-βIle-His-Pro-Ile; (SEQ ID NO: 6)

Arg-Val-Tyr-Ile-His-βPro-Ile; (SEQ ID NO: 6)

Arg-Val-Tyr-Ile-His-Pro-βIle; (SEQ ID NO: 6)

D-Asp-Arg-Val-Tyr-βIle-His-Pro-Phe;

D-Arg-Val-Tyr-Ile-His-Pro-Phe; (SEQ ID NO: 5)

D-Arg-Val-Tyr-βIle-His-Pro-Phe; (SEQ ID NO: 6)

D-Arg-Val-Tyr-Ile-His-βPro-Phe; (SEQ ID NO: 6)

D-Arg-Val-Tyr-Ile-His-βPro-Trp; (SEQ ID NO: 10)

N-Ac-Arg-Val-Tyr-Ile-His-βPro-Phe; (SEQ ID NO: 6)

N-Ac-Arg-Val-Tyr-Ile-His-βPro-Trp; (SEQ ID NO: 10)

Asp-βArg-Val-Tyr-Ile-His-Pro-Ala; (SEQ ID NO: 11)

Asp-Arg-βVal-Tyr-Ile-His-Pro-Ala; (SEQ ID NO: 11)

Asp-Arg-Val-βTyr-Ile-His-Pro-Ala; (SEQ ID NO: 11)

Asp-Arg-Val-Tyr-βIle-His-Pro-Ala; (SEQ ID NO: 11)

Asp-Arg-Val-Tyr-Ile-His-βPro-Ala; (SEQ ID NO: 11)

βArg-Val-Tyr-Ile-His-Pro-Ala; (SEQ ID NO: 12)

Arg-βVal-Tyr-Ile-His-Pro-Ala; (SEQ ID NO: 12)

Arg-Val-βTyr-Ile-His-Pro-Ala; (SEQ ID NO: 12)

Arg-Val-Tyr-βIle-His-Pro-Ala; (SEQ ID NO: 12)

Arg-Val-Tyr-Ile-His-βPro-Ala; (SEQ ID NO: 12)

βArg-Val-Tyr-Ile-His-Pro-Trp; (SEQ ID NO: 10)

Arg-βVal-Tyr-Ile-His-Pro-Trp; (SEQ ID NO: 10)

Arg-Val-βTyr-Ile-His-Pro-Trp; (SEQ ID NO: 10)

Arg-Val-Tyr-βIle-His-Pro-Trp; (SEQ ID NO: 10)

Arg-Val-Tyr-Ile-His-βPro-Trp; (SEQ ID NO: 10)

Arg-Val-Tyr-Ile-His-Pro-βTrp; (SEQ ID NO: 10)

Val-Tyr-Ile-Tyr-βPro-Trp; (SEQ ID NO: 13)

Val-Tyr-Ile-His-βPro-Trp; (SEQ ID NO: 14)

Arg-Val-Tyr-Ile-Tyr-βPro-Trp; (SEQ ID NO: 15)

Arg-Val-Tyr-Ile-βTyr-Pro-Trp; (SEQ ID NO: 15)

Asp-Arg-Val-Tyr-Ile-Tyr-βPro-Trp; (SEQ ID NO: 16)

Asp-Arg-Val-Tyr-Ile-βTyr-Pro-Trp; (SEQ ID NO: 16)

Val-Tyr-Ile-Tyr-βPro-Phe; (SEQ ID NO: 17)

Arg-Val-Tyr-Ile-Tyr-βPro-Phe; (SEQ ID NO: 18)

Arg-Val-Tyr-Ile-βTyr-Pro-Phe; (SEQ ID NO: 18)

Asp-Arg-Val-Tyr-Ile-Tyr-βPro-Phe; (SEQ ID NO: 19)

Asp-Arg-Val-Tyr-Ile-βTyr-Pro-Phe; (SEQ ID NO: 19)

Tetrazole-CONH-Arg-Val-Tyr-Ile-Tyr-βPro-Trp; (SEQ ID NO: 15)

Tetrazole-CONH-Arg-Val-Tyr-Ile-Tyr-βPro-Phe; (SEQ ID NO: 18)

Nicotinamido- Arg-Val-Tyr-Ile-Tyr-βPro-Phe; (SEQ ID NO: 18)

Nicotinamido- Arg-Val-Tyr-Ile-Tyr-βPro-Trp; (SEQ ID NO: 15)

Cholate-Arg-Val-Tyr-Ile-Tyr-βPro-Trp; (SEQ ID NO: 15)

Cholate-Arg-Val-Tyr-Ile-Tyr-βPro-Phe; (SEQ ID NO: 18)

Deoxycholate-Arg-Val-Tyr-Ile-Tyr-βPro-Trp; (SEQ ID NO: 15)

Deoxycholate-Arg-Val-Tyr-Ile-Tyr-βPro-Phe; (SEQ ID NO: 18)

Ursodeoxycholate-Arg-Val-Tyr-Ile-Tyr-βPro-Trp; (SEQ ID NO: 15)

Ursodeoxycholate-Arg-Val-Tyr-Ile-Tyr-βPro-Phe; (SEQ ID NO: 18)

(SEQ ID NO: 15)
Obeticholate-Arg-Val-Tyr-Ile-Tyr-βPro-Trp;
or (SEQ ID NO: 18)
Obeticholate-Arg-Val-Tyr-Ile-Tyr-βPro-Phe.

In a preferred embodiment, the present invention provides a peptide comprising or consisting of the sequence Arg-Val-Tyr-Ile-His-Pro-Trp (SEQ ID NO: 10).

Preferably, one or more amino acid residues of the Arg-Val-Tyr-Ile-His-Pro-Trp (SEQ ID NO: 10) peptide are in β form (including $\beta^2$ or $\beta^3$ forms), more preferably, wherein the Proline residue at position $Xaa_7$ is βPro, even more preferably, βhomoPro.

The N-terminal amino acid residue of the Arg-Val-Tyr-Ile-His-Pro-Trp (SEQ ID NO: 10) peptide may also be modified. Any N-terminal modification as described herein may be used, including acetylation, N-terminal pyroglutamate, a non-natural amino acid substitution, PEGylation, lipidation, glycosylation and N-methylation. In one example, the N-terminal modification is acetylation (i.e., an N—Ac cap). Alternatively, the N-terminal amino acid residue may be a D-amino acid.

In one embodiment, the peptide comprises or consists of the sequence D-Arg-Val-Tyr-Ile-His-βPro-Trp (SEQ ID NO: 10). In an alternative embodiment, the peptide comprises or consists of the sequence N—Ac-Arg-Val-Tyr-Ile-His-βPro-Trp (SEQ ID NO: 10).

The invention provides a pharmaceutical composition for treating or preventing fibrosis comprising a peptide that exhibits greater than about 100-fold selectivity for the AT2R than the AT1R as described herein and a pharmaceutically acceptable diluent, excipient or carrier. In one embodiment, the only active ingredient present in the composition is a peptide that exhibits greater than about 100-fold selectivity for the AT2R than the AT1R.

The invention provides a pharmaceutical composition for treating or preventing fibrosis comprising as an active ingredient a peptide that exhibits greater than about 100-fold selectivity for the AT2R than the AT1R as described herein and a pharmaceutically acceptable diluent, excipient or carrier. In one embodiment, the only active ingredient present in the composition is a peptide that exhibits greater than about 100-fold selectivity for the AT2R than the AT1R.

The invention provides a pharmaceutical composition for treating or preventing fibrosis comprising as a main ingredient a peptide that exhibits greater than about 100-fold selectivity for the AT2R than the AT1R as described herein and a pharmaceutically acceptable diluent, excipient or carrier. In one embodiment, the only active ingredient present in the composition is a peptide that exhibits greater than about 100-fold selectivity for the AT2R than the AT1R.

The invention also provides a peptide that exhibits greater than about 100-fold selectivity for the AT2R than the AT1R for use in the treatment of fibrosis.

The invention also provides a pharmaceutical composition comprising a peptide that exhibits greater than about 100-fold selectivity for the AT2R than the AT1R and a pharmaceutically acceptable diluent, excipient or carrier for use in the treatment of fibrosis.

In any aspect or embodiment of the invention, the peptide has a half-life greater than 5 minutes in vivo. In a preferred embodiment, the peptide has a half-life greater than 30 minutes, 50 minutes, 1 hour, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours in vivo. Preferably, the stability of the peptide is determined using a method as described herein, for example in the Examples. In a preferred embodiment, the peptide has been modified at the N terminus to increase the half-life of the agonist. In a preferred embodiment, this modification is a modification to a D-amino acid or N-acetylation.

Any aspects of the methods or uses described herein also apply to purpose limited descriptions of any product described herein (such as for example, in a purpose limited product claim).

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

Right-hand panel: Representative images are shown of transverse kidney sections stained for glomerular fibrosis determined by picrosirius red, under bright field microscopy, taken from male FVB/N mice that were untreated (normal salt, NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet. Corresponding mean data are shown below for glomerular fibrosis, taken from male FVB/N mice that were untreated (normal salt; NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=6-10). All three AT2R agonists reversed the glomerular fibrosis caused by high salt in the kidney. Data expressed as mean±s.e.m of percentage positive glomerular area stained for picrosirius red. ** P<0.01 versus normal salt (NS); #P<0.05 versus high salt (one way ANOVA with Tukey's correction for multiple comparisons).

Figure 40:
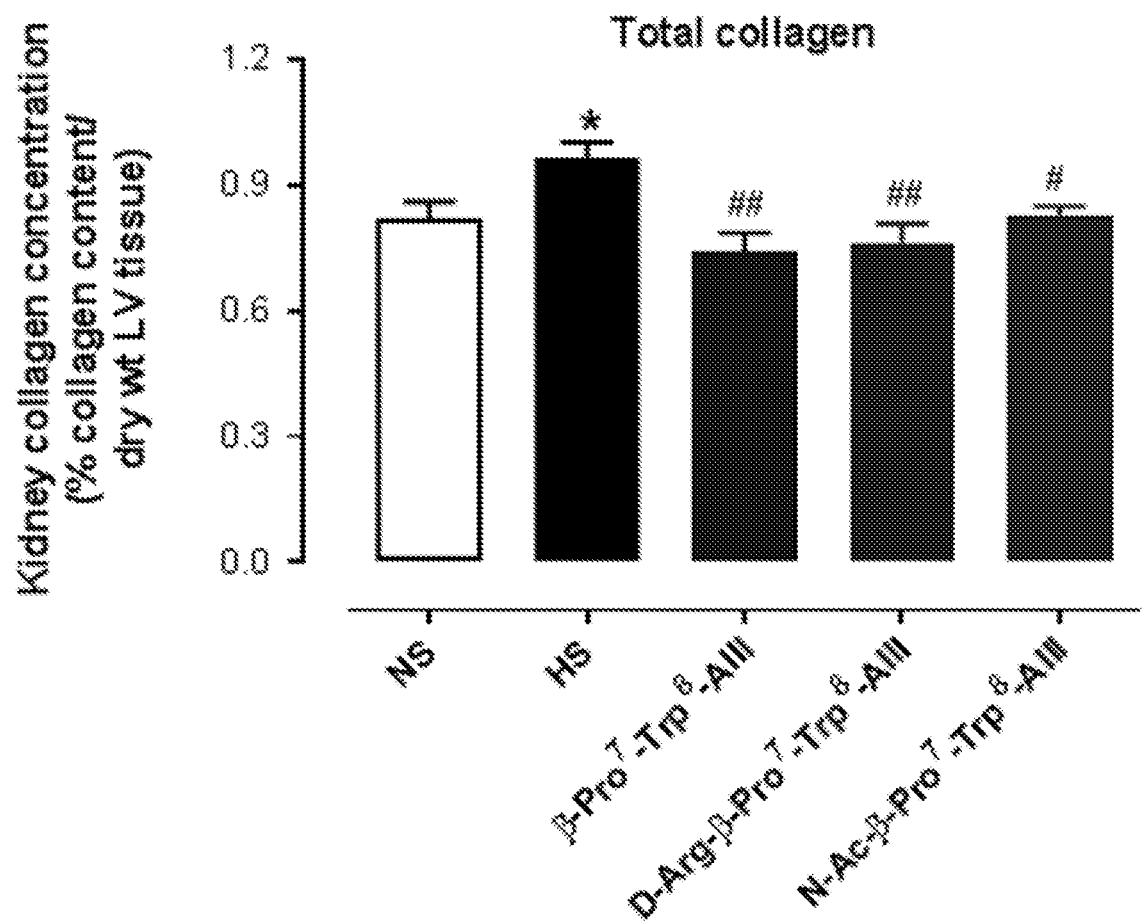

FIG. 40: AT2R stimulation by β-Pro$^7$-Trp$^8$-Ang III, D-Arg$^2$-β-Pro$^7$-Trp$^8$-Ang III or N—Ac—β-Pro$^7$-Trp$^8$-Ang III attenuates high salt (5%)-mediated fibrosis in mouse kidney. Mean data for renal fibrosis determined by hydroxyproline (HP) analysis, taken from male FVB/N mice that were untreated (normal salt; NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=7-8). All three AT2R agonists reversed the pro-fibrotic effects of high salt in the kidney. Data expressed as mean±s.e.m of kidney % collagen content normalised to kidney weight. *P<0.05 versus NS; #P<0.05, ##P<0.01 versus HS (one way ANOVA with Tukey's correction for multiple comparisons).

Figure 41:
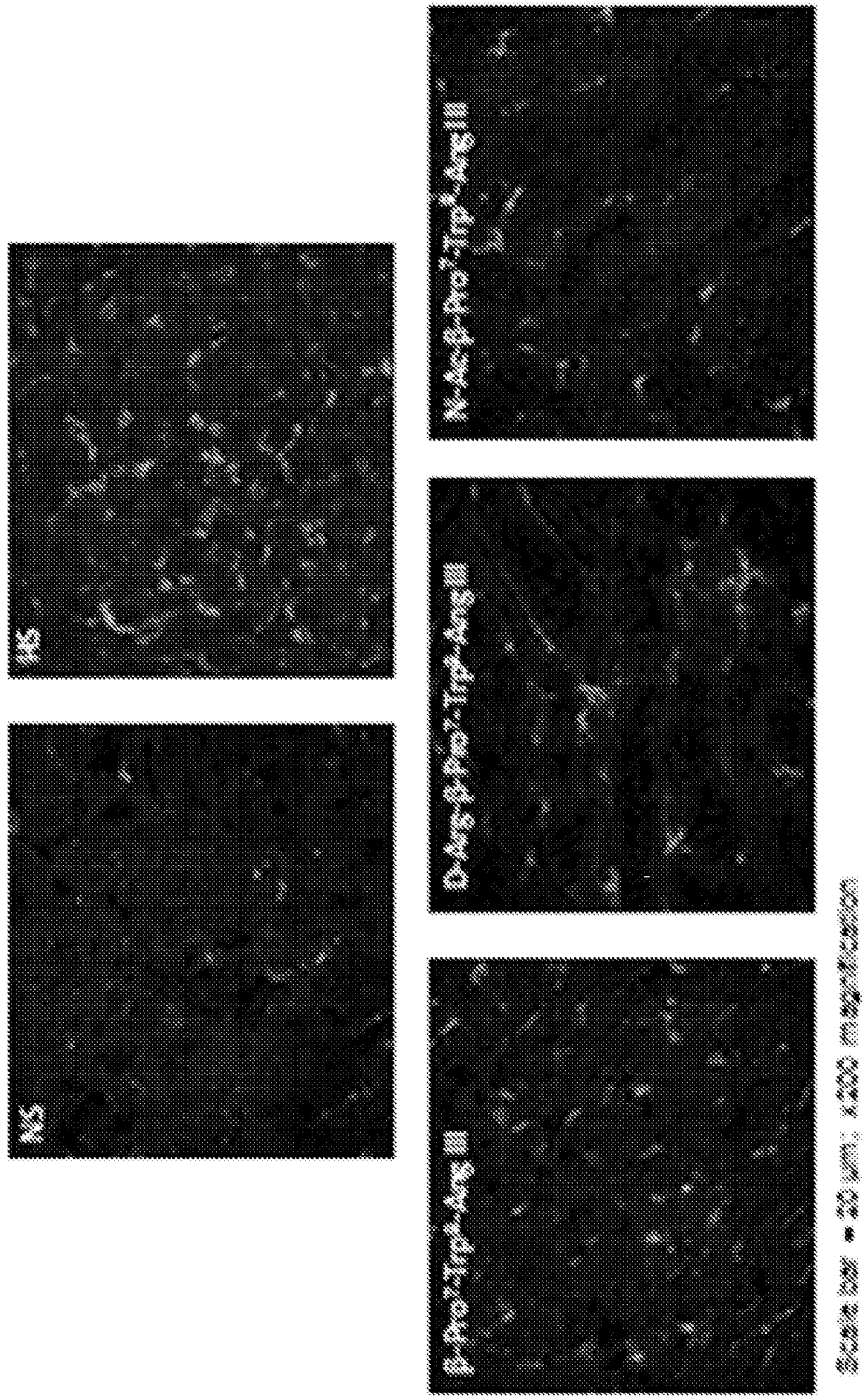
Figure 41:
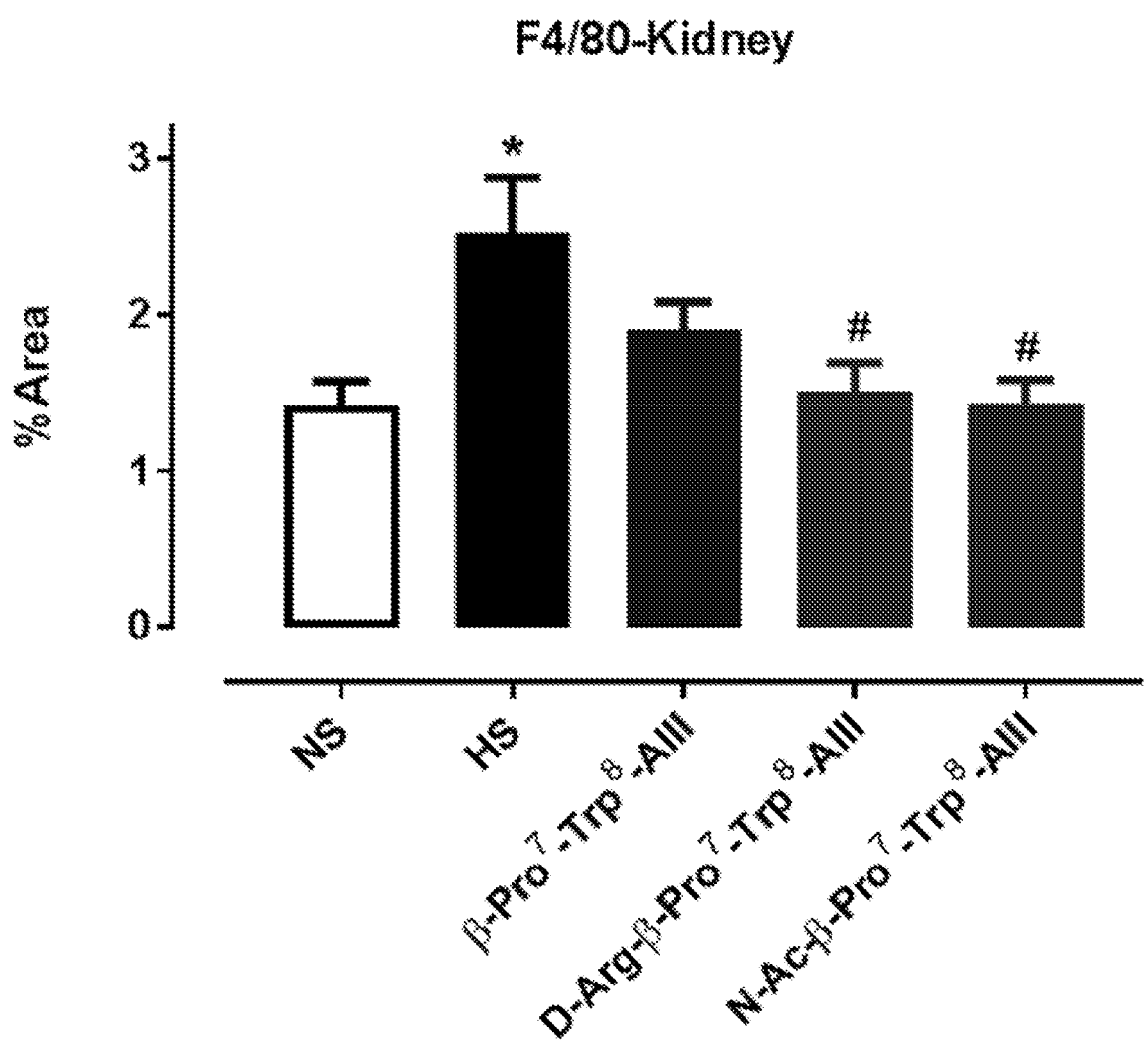

FIG. 41: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated macrophage infiltration in mouse kidney. Left-hand panel: Representative images are shown of transverse kidney sections of macrophage infiltration/expression (using F4/80 immunofluorescence; green), taken from male FVB/N mice that were untreated (normal salt, NS); fed a high salt diet for 8 weeks (HS) or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet. Right-hand panel: Mean data for macrophage infiltration, taken from male FVB/N mice that were untreated (normal salt; NS); fed a high salt diet for 8 weeks (HS) or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=7-10). All three AT2R agonists reversed high salt-induced macrophage infiltration in the kidney. Data expressed as mean±s.e.m of percentage positive stained area for F4/80. *P<0.05 versus normal salt (NS); #P<0.05 versus high salt (one way ANOVA with Tukey's correction for multiple comparisons).

Figure 42:
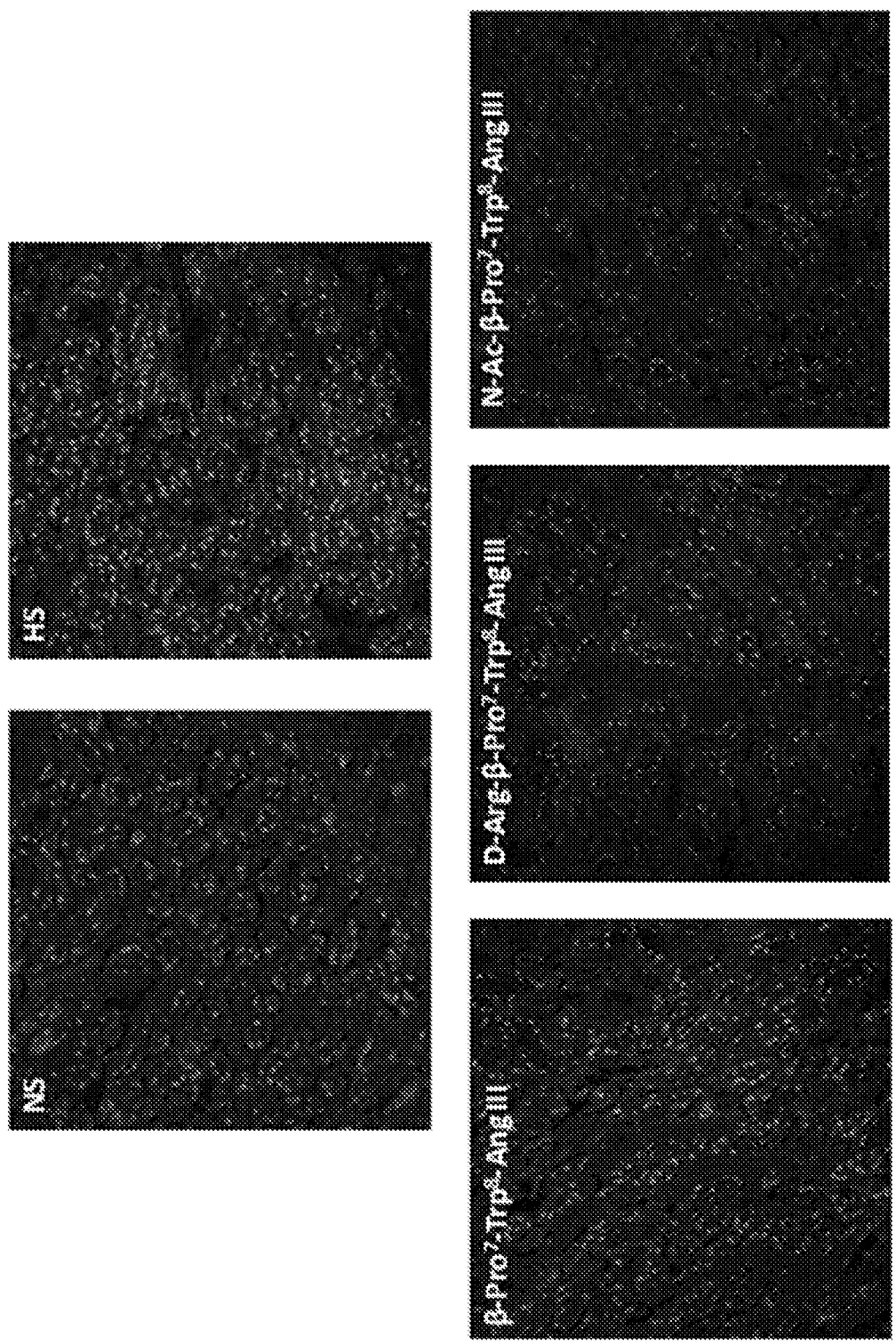
Figure 42:
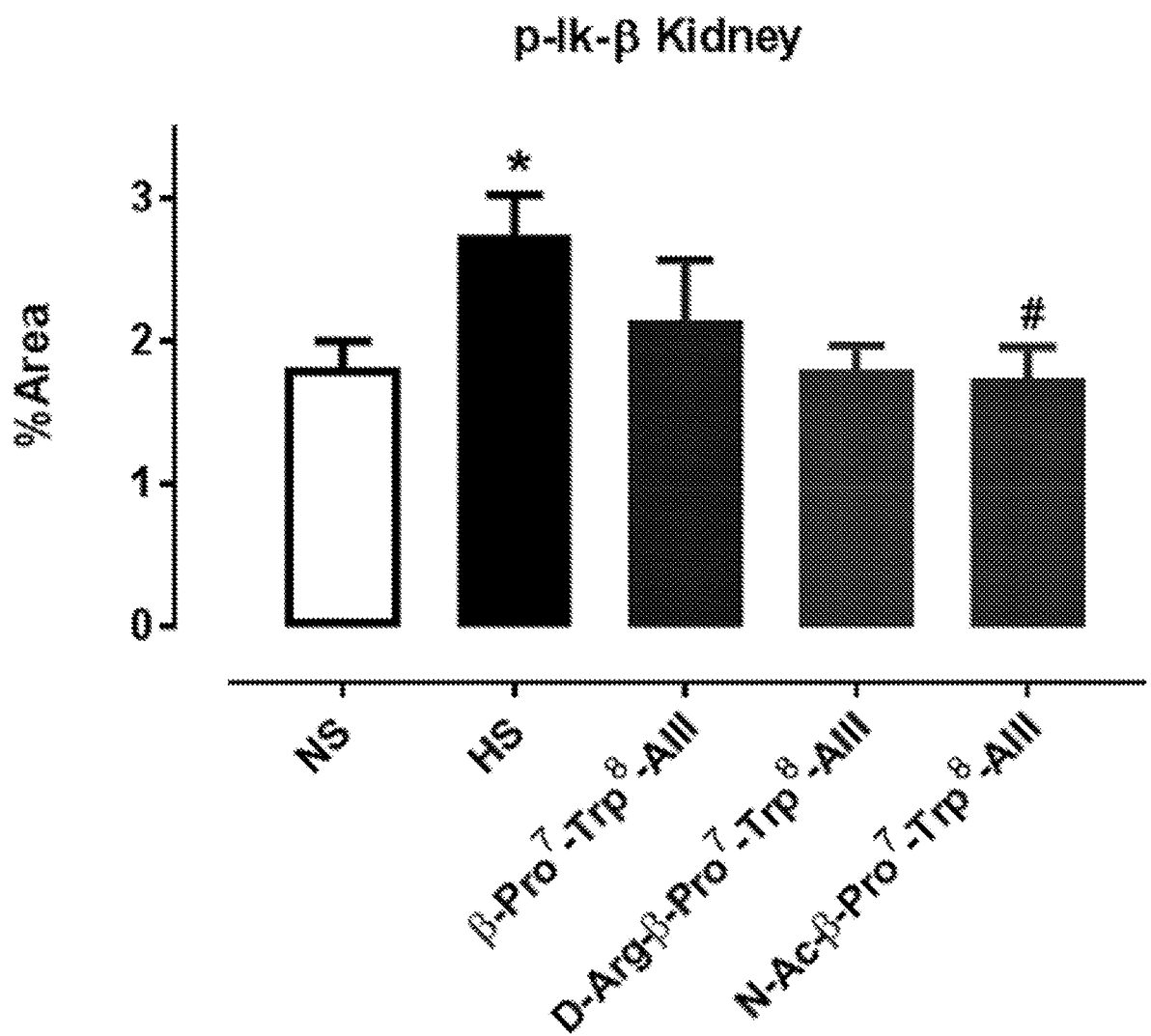

FIG. 42: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated inflammation in mouse kidney. Left-hand panel: Representative images are shown of transverse kidney sections of the pro-inflammatory marker NFκB (measured via phospho-IκBα expression using immunofluorescence staining; green), taken from male FVB/N mice that were untreated (normal salt, NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet. Right-hand panel: Mean data for phospho-IκBα expression, taken from male FVB/N mice that were untreated (normal salt; NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=6-9). All three AT2R agonists reversed high salt-induced renal inflammation in the kidney. Data expressed as mean±s.e.m of percentage positive stained area for phospho-IκBα. *P<0.05 versus normal salt (NS); #P<0.05 versus high salt (one way ANOVA with Tukey's correction for multiple comparisons).

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The inventors have identified a number of highly selective AT2R agonists as a novel compounds to combat fibrosis. The inventors hypothesized that stimulation of AT2R activity compared to AT1R would protect against cardiac fibrosis and inflammation, or other cardiovascular disease-related, tissue injury related organ fibrosis or hypertension-related fibrosis to improve cardiac and vascular function. The inventors tested this hypothesis in an intervention model in which a high salt (5%) diet was fed to FVB/N mice to induce fibrosis and inflammation in multiple organs, and then administer various peptides to mice with established cardiovascular pathologies, in order to reverse CVD. The inventors found that pharmacological stimulation of AT2Rs protected against and, more importantly, reversed injury-induced organ fibrosis (e.g. in heart; kidneys; liver) often to the level exhibited in untreated mice, in part by inhibiting synthesis and enhancing degradation of collagen. In addition, AT2R stimulation reduced inflammatory markers in the same organs.

An advantage of the invention is the surprising finding that treatment with an AT2R agonist at the time of established fibrotic disease leads to a reversal of organ fibrosis, and often caused a greater anti-fibrotic effect than an AT1R antagonist (herein referred to as an ARB). Pharmacological stimulation of AT2Rs therefore not only has the effect of halting progression of fibrosis but reversing the existing symptoms, such as collagen deposition. The invention therefore finds particular application to subjects that are diagnosed with fibrosis or for cardiovascular diseases that are often associated with organ fibrosis. Further, reversing the hallmarks of age-induced fibrosis indicates that the invention can be applied to subjects with advanced fibrosis.

As used herein, an 'AT2R agonist' is any compound that stimulates the activity of the Angiotensin II Receptor type 2 (herein, "AT2R"). The AT2R agonist stimulates AT2R-mediated signalling pathways. Typically, the AT2R agonist directly binds to the active site of the AT2R or a related allosteric site that leads to stimulation of the AT2R. Stimulation of the AT2R can lead to increases in various phosphatases including but not limited to mitogen-activated protein kinase phosphatase (MKP-1), tyrosine phosphatases and serine/threonine phosphatases and inhibition of ERK activity. This results in the reduction of mitogen-activated protein kinase (MAPK) activity and kinase-related activity. The AT2R is also involved in the regulation of nitric oxide (NO), guanosine cyclic 3'5'-monophosphate (cGMP) and bradykinin production, both circulating and in tissues. The AT2R has also been shown to regulate inflammatory mediators including NF-κB, TNF-α, IL-6 and TGF-β.

AT2R stimulation is associated with decreases in inflammation, fibrosis, apoptosis and cellular growth and improvements in endothelial function, renal blood flow and vasodilation.

Binding of an AT2R agonist can be measured using known approaches in the art. These include radioligand binding studies or autoradiographic studies using nonselective iodinated compounds (such as $^{125}$I-AngII or $^{125}$I-Sar$^1$-Ile$^8$-AngII) (Servant et al (1993) Mol Pharmacol) or selective iodinated compounds such as $^{125}$I-CGP42112 (Whitebread et al 1991; BBRC), or proximity assays using fluorescent ligands and luciferase-tagged receptors to perform fluorescence resonance energy transfer (FRET) and bioluminescence resonance energy transfer (BRET) experiments (Stoddart et al 2015 Nature Methods 12: 661-663).

In any aspect or embodiment of the invention, reference to an AT2R agonist that has greater than about 100-fold selectivity for the AT2R than the AT1R includes reference to any peptide described herein, for example those peptides described in Table 3.

A "compound" as used herein, may be a proteinaceous agent including a peptide, or a compound derived from a protein or peptide, including modified proteins, modified peptides, variants, derivatives or analogs of the same. In alternative embodiments, the compound is not peptidyl or not proteinaceous, and may include small molecule (chemical) compounds, interfering RNA molecules or other nucleic acid derived compounds which agonise AT2R.

A "peptide" as used herein refers to a polymer of amino acid residues and to variants and synthetic analogues of the same. Thus, this term applies to amino acid polymers in which one or more amino acid residues is a synthetic non-naturally-occurring amino acid, such as a chemical analogue of a corresponding naturally-occurring amino acid, as well as to naturally-occurring amino acid polymers. This term do not exclude modifications, such as those described herein, to either the side chain of an amino acid or the N- or C-terminus of the peptide.

The AT2R peptides described herein may have conservative substitutions of at least one amino acid residue. Preferably, this conservative substitution does not alter the overall conformation or function of the peptide. Preferably the conservative substitution comprises a replacement of an amino acid with another having one or more similar properties. Table 1 outlines the properties of each of the amino acids.

Amino acids with similar properties are well known in the art. For example, polar/hydrophilic amino acids which may be interchangeable include asparagine, glutamine, serine, threonine, lysine, arginine, histidine, aspartate and glutamate; nonpolar/hydrophobic amino acids which may be interchangeable include glycine, alanine, valine, leucine, isoleucine, proline, tyrosine, phenylalanine, tryptophan and methionine; acidic amino acids which may be interchangeable include aspartate and glutamate and basic amino acids which may be interchangeable include histidine, lysine and arginine.

TABLE 1

| Amino acid | 3-letter code | Properties |
|---|---|---|
| Alanine | Ala | aliphatic hydrophobic neutral |
| Arginine | Arg | polar hydrophilic charged (+) |
| Asparagine | Asn | polar hydrophilic neutral |
| Aspartate | Asp | polar hydrophilic charged (−) |
| Cysteine | Cys | polar hydrophobic neutral |
| Glutamine | Gln | polar hydrophilic neutral |
| Glutamate | Glu | polar hydrophilic charged (−) |
| Glycine | Gly | aliphatic neutral |
| Histidine | His | aromatic polar hydrophilic charged (+) |
| Isoleucine | Ile | aliphatic hydrophobic neutral |
| Leucine | Leu | aliphatic hydrophobic neutral |
| Lysine | Lys | polar hydrophilic charged (+) |
| Methionine | Met | hydrophobic neutral |
| Phenylalanine | Phe | aromatic hydrophobic neutral |
| Proline | Pro | hydrophobic neutral |
| Serine | Ser | polar hydrophilic neutral |
| Threonine | Thr | polar hydrophilic neutral |
| Tryptophan | Trp | aromatic hydrophobic neutral |
| Tyrosine | Tyr | aromatic polar hydrophobic |
| Valine | Val | aliphatic hydrophobic neutral |

The AT2R peptides described herein may have non-, or unnatural amino acids incorporated. Unless otherwise specified, any amino acid may be natural or non-natural/unconventional. Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural/non-conventional amino acids contemplated herein is shown in Table 2.

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |

TABLE 2-continued

| Non-conventional amino acid | Code | Non-conventional amino acid | Code |
|---|---|---|---|
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyl-α-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) | Nnbhe |
| 1-carboxy-1-(2,2-diphenyl-ethylamino)cyclopropane | Nmbc | | |
| p-amino phenylalanine, | | | |
| p-carboxy phenylalanine, | | | |
| 2,6-dinitro phenylalanine | | | |
| 7-azatryptophan | | | |
| Benzimidazole-5(6)-alanine | | | |

Preferred unnatural/non-conventional amino acids for use in the AT2R peptides described herein include: D-N-methyltryptophan, p-amino phenylalanine, p-carboxy phenylalanine, 2,6-dinitro phenylalanine, 7-azatryptophan, Benzimidazole-5(6)-alanine, N-(p-hydroxyphenyl)glycine and N-methyl-α-napthylalanine. It will be understood that these preferred non-conventional amino acids can be used in place of the corresponding conventional amino acid residue in a peptide described herein. (For example, D-N-methyltryptophan or 7-azatryptophan could be used in place of tryptophan at position $Xaa_8$; p-amino phenylalanine, p-carboxy phenylalanine or 2,6-dinitro phenylalanine could be used in place of phenylalanine at position $Xaa_8$ etc).

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

As used herein, reference to an AT2R agonist also includes a pharmaceutically acceptable salt, solvate, polymorph or prodrug thereof.

The peptides as described herein may also have N-terminal modifications. Preferably, the modification reduces or inhibits degradation by aminopeptidases. Preferably, the modification increases the plasma half-life of the peptide compared to a peptide that does not contain the modification. Plasma half-life can be determined by methods known in the art including described herein in the Examples. Typical N-terminal modifications include acetylation, N-terminal pyroglutamate, PEGylation lipidation, glycosylation, N-methylation. The modification may be an addition to the N-terminus of the peptide, including conjugation to vitamins (including Nicotinamide conjugation) or bile acids, capping with imidazole carboxylate or tetrazole carboxylate or where the N-acyl cap can be selected from; —$C_{1-6}$ alkyl, optionally substituted —$C_{1-6}$ haloalkyl, optionally substituted —$C_{2-6}$ alkenyl, optionally substituted —$C_{3-6}$ cycloalkyl, optionally substituted phenyl, optionally substituted —$C_{1-3}$ alkyl, —$C_{3-6}$ cycloalkyl and optionally substituted —$C_{1-3}$ alkylphenyl, a non-natural amino acid substitution and any other N-terminal modification as described herein.

Proteolytic stability may be tested in a plasma stability assay used to assess the susceptibility of a peptide described herein to plasma proteases. Plasma stability may be tested using methods described herein. For example, a sample of rat plasma may be incubated with peptide of interest (final concentration was 1 mg/mL; plasma diluted by 10% with peptide dissolved in saline). Protease activity is then quenched in samples by the addition of acetonitrile, at selected time intervals. The amount of parent compound remaining at each time point can then be assayed on an Agilent 1100 MSD SL ion trap mass spectrometer. The peaks observed in the resulting chromatograms are integrated, compared to a standard curve, and cross-checked by mass and retention time (Jones et al 2011 Hypertension. 57: 570-576). Preferably, an agonist described herein has a half-life greater than 5 minutes as determined by a plasma stability assay, for example the assay described herein. In a preferred embodiment, an agonist has a half-life greater than 30 minutes, 50 minutes, 1 hour, 2, 3, 4, 5, 6, 7, 8, 9, 10, 11, 12, 13, 14, 15, 16, 17, 18, 19, 20, 21, 22, 23, 24, 25, 26, 27, 28, 29 or 30 hours as determined by a plasma stability assay, for example the assay described herein.

The term 'pharmaceutically-acceptable salts' refers to those salts which, within the scope of sound medical judgement, are suitable for use in contact with the tissues of humans and animals without undue toxicity, irritation, allergic response and the like, and are commensurate with a reasonable benefit/risk ratio.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians. For example, prevention of age-induced cardiac fibrosis, or cardiac or renal fibrosis associated with hypertensive heart disease, hypertensive cardiomyopathy or heart failure, or nephropathy with or without associated diabetes, may be characterised by an absence of interstitial collagen deposition, or an absence of an increase in interstitial collagen deposition if collagen deposition is already detectable in a subject.

The terms "treatment" or "treating" of a subject includes the application or administration of a compound of the invention to a subject (or application or administration of a compound of the invention to a cell or tissue from a subject) with the purpose of delaying, slowing, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being.

The existence of, improvement in, treatment of or prevention of a fibrotic disease may be by any clinically or biochemically relevant method of the subject or a biopsy therefrom. For example, a parameter measured may be the presence of fibrosis, the content of collagen, fibronectin, or another extracellular matrix protein, the phosphatidic acid level or choline level, the proliferation rate of the cells or any extracellular matrix components in the cells or transdifferentiation of the cells to myofibroblasts. For example, inhibition of kidney fibrosis can be detected by preventing a further loss of kidney function as measured by albuminurea or proteinurea, increased serum creatinine, a reduction in active fibrosis as measured by reduced levels of collagen fragments in urine samples, and by a reduction in the presence of myofibroblasts on kidney biopsy tissue. Further, for example, in lung fibrosis, a positive response to therapy would be to prevent a further decline in lung function as measured by spirometry, body plethysmography, and lung diffusion capacity. In addition, blood levels of collagen fragments would also be reduced.

Reversing fibrosis as described herein includes inhibiting synthesis and/or enhancing degradation of collagen. A clinically or biochemically observable consequence of a reversal of fibrosis is a reduction in fibrotic tissue formed as a response to ageing or tissue injury. Reversing fibrosis also may include a clinically or biochemically observable reduction in any characteristic or symptom of fibrosis as described herein at a time after treatment has commenced compared to a time prior to treatment commencing.

The phrase 'therapeutically effective amount' generally refers to an amount of one or more AT2R agonists, a pharmaceutically acceptable salt, polymorph or prodrug thereof of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

"Fibrosis", "Fibrotic disease" or "Fibro proliferative disease" means the formation of excess fibrous connective tissue in a reparative process upon injury. Scarring is a result of continuous fibrosis that obliterates the affected organs or tissues architecture. As a result of abnormal reparative processes, which do not clear the formed scar tissue, fibrosis progresses further. Fibrosis can be found in various tissues, including the heart, the lungs, the liver, the skin, blood vessels and the kidneys. Examples of fibrosis are described herein and include pulmonary fibrosis, liver cirrhosis, systemic sclerosis, progressive kidney disease and cardiac fibrosis associated with various cardiovascular diseases.

An individual may be identified as having fibrosis by determining if a subject has organ dysfunction, scarring, alteration of normal extracellular matrix balance, increase in collagen deposition, increased collagen volume fraction, differentiation of fibroblasts to myofibroblasts, reduction in the level of matrix metalloproteinases and increase in the level of tissue Inhibitors of matrix metalloproteinases, increased levels of either N-terminal or C-terminal propeptide of type I procollagen (PINP or PICP) and decreased levels of C-terminal telopeptide of Type I Collagen (CTP or CITP), increased collagen deposition and impaired cardiac function measured by various noninvasive imaging techniques, impaired renal function measured by increased proteinurea and albuminurea, decreased glomerular filtration rate, doubling of plasma creatinine levels or altered liver enzymes alanine transaminase (ALT) or aspartate transaminase (AST).

Preferably the fibrotic disease is associated with the presence of, or upregulation of, AT2R expression and/or activity. AT2R expression or activity can be measured by any assay described herein. Approaches to measure AT2R activation include the measurement of G-protein subunit activation of $G_{\alpha i}$ through measurement of radioactive guanosine 5'-3-O-(thio)triphosphate (GTPγS) binding (Hansen et al (2000) Circ Research, 87:753-759), or by measuring NO-CGMP production (Hannan et al (2003) Brit J Pharmacol, 140: 809-24), or by measuring phosphatase activity (Tsuzuki et al (1996) Hypertension 28: 916-8), or by measuring the reduction in TNF-α-mediated IL-6 release from fibroblasts (Rompe et al. (2010) Hypertension 55:924-31), or by measuring vasorelaxation of pre-contracted isolated vascular preparations (Widdop et al (2002) Hypertension 40: 516-20), or by measuring in vivo depressor effects in rodents during AT1 receptor blockade (Barber et al (1999) Hypertension 34: 1112-6).

Organ fibrosis related to tissue injury includes fibrosis associated with cardiovascular disease and fibrosis that has occurred following an organ transplant, such as a kidney or liver transplant.

According to a preferred embodiment of the invention, the pulmonary fibrosis is idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapours, drug-induced interstitial lung disease, or pulmonary hypertension.

According to a preferred embodiment of the invention, the liver fibrosis is resulting from a chronic liver disease, hepatitis B virus infection, hepatitis C virus infection, hepatitis D virus infection, schistosomiasis, alcoholic liver disease or non-alcoholic steatohepatitis, obesity, diabetes, protein malnutrition, coronary artery disease, auto-immune hepatitis, cystic fibrosis, alpha-1-antitrypsin deficiency, primary biliary cirrhosis, drug reaction and exposure to toxins.

According to a preferred embodiment of the invention, the skin fibrosis is scarring, hypertrophic scarring, keloid scarring, dermal fibrotic disorder, psoriasis or scleroderma. Said scarring may derived from a burn, a trauma, a surgical injury, a radiation or an ulcer. Said ulcer can be a diabetic foot ulcer, a venous leg ulcer or a pressure ulcer.

The term "pulmonary fibrosis" or "lung fibrosis" means the formation or development of excess fibrous connective tissue (fibrosis) in the lung thereby resulting in the development of scarred (fibrotic) tissue. More precisely, pulmonary fibrosis is a chronic disease that causes swelling and scarring of the alveoli and interstitial tissues of the lungs. The scar tissue replaces healthy tissue and causes inflammation. This chronic inflammation is, in turn, the prelude to fibrosis. This damage to the lung tissue causes stiffness of the lungs which subsequently makes breathing more and more difficult.

The term "liver fibrosis" means the formation or development of excess fibrous connective tissue (fibrosis) in the liver thereby resulting in the development of scarred (fibrotic) tissue. The scarred tissue replaces healthy tissue by the process of fibrosis and leads to subsequent cirrhosis of the liver.

The term "skin fibrosis" or "dermal fibrosis" means the excessive proliferation of epithelial cells or fibrous connective tissue (fibrosis) thereby resulting in the development of scarred (fibrotic) tissue. The scarred tissue replaces healthy tissue by the process of fibrosis and may be the prelude of systemic scleroderma. Skin fibrosis is intended to cover the fibrosis of any skin tissue and epithelial cells including, without limitation, blood vessels and veins, internal cavity of an organ or a gland such as ducts of submandibular, gallbladder, thyroid follicles, sweat gland ducts, ovaries, kidney; epithelial cells of gingival, tongue, palate, nose, larynx, oesophagus, stomach, intestine, rectum, anus and vagina; derma, scar, skin and scalp. The compounds of the present invention may be active for promoting healing of wound and one or more of the following activities:

improving collagen organization and/or reducing wound cellularity in said wound;

reducing collagen overproduction by fibroblast and epithelial cells in said wound;

reducing epithelial mesenchymal transition in said wound;

reducing fibroblast migration and activation in said wound;

reducing and/or inhibiting dermal thickening in said wound;

reducing and/or inhibiting recruitment of inflammatory cells to said wound.

The term "cardiac fibrosis" or "heart fibrosis" means an abnormal thickening of the heart valves due to inappropriate proliferation of cardiac fibroblasts but more commonly refers to the proliferation of fibroblasts in the cardiac muscle. Fibrocyte cells normally secrete collagen, and function to provide structural support for the heart. When over-activated this process causes thickening and fibrosis of the valves and heart muscle itself, with white tissue building up primarily on the tricuspid or mitral valve, but also occurring on the pulmonary or aortic valve. The thickening and loss of flexibility eventually may lead to valvular dysfunction and right-sided or left-sided heart failure. In general, prophylactic and therapeutic uses comprise the administration of a compound as described herein to a subject, preferably a human patient in need thereof.

"Idiopathic pulmonary fibrosis (IPF)" is a specific manifestation of idiopathic interstitial pneumonia (IIP), a type of interstitial lung disease. Interstitial lung disease, also known as diffuse parenchymal lung disease (DPLD), refers to a group of lung diseases affecting the interstitium. Microscopically, lung tissue from IPF patients shows a characteristic set of histological features known as usual interstitial pneumonia (UIP). UIP is therefore the pathologic presentation of IPF.

Exemplary forms of fibrosis include, but are not limited to, cardiac fibrosis, liver fibrosis, kidney fibrosis, lung fibrosis, vascular fibrosis, dermal scarring and keloids, and Alzheimer's disease. In still further embodiments, cardiac fibrosis is associated with hypertension, hypertensive heart disease (HHD), hypertensive cardiomyopathy (HCM), myocardial infarction (MI), and restenosis or as a result of impaired renal function resulting from renal fibrosis.

Preferably, the fibrosis is kidney fibrosis. The kidney fibrosis may include, but not be limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN. The liver fibrosis may include, but not be limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis). Lung fibrosis may include idiopathic pulmonary fibrosis (IPF) or cryptogenic fibrosing alveolitis, chronic fibrosing interstitial pneumonia, interstitial lung disease (ILD), and diffuse parenchymal lung disease (DPLD)). Cardiac fibrosis, congestive heart failure, cardiomyopathy, post-myocardial infarction defects in heart function; peripheral vascular disease; rheumatoid arthritis; glaucoma; age-related macular degeneration (wet AMD and dry AMD); emphysema, chronic obstructive pulmonary disease (COPD); multiple sclerosis; and chronic asthma may also be prevented, treated, or ameliorated with compositions, methods or uses as described herein.

In a preferred form, the fibrotic disease is cardiac, renal or interstitial fibrosis.

Scleroderma (systemic sclerosis), a chronic systemic autoimmune disease characterised by hardening (sclero) of the skin (derma) and internal organs (in severe cases). Clinically, patient stratification and drug efficacy can be measured through biopsy/visualization of reduced skin lesions and other objective measures assessed over 24 and 48 weeks. As such, diabetic nephropathy, IgA nephropathy or scleroderma are also fibrotic conditions for treatment and/or prevention.

In the cardiovascular system a progressive age-related deposition of collagen in the vascular wall and in the cardiac interstitial and perivascular space, or collagen deposition related to cardiovascular or renal disease, leads to reduction of myocardial and arterial compliance.

The frequency of administration of a peptide or composition as described herein may be once daily, or 2 or 3 time daily. The treatment period may be for the duration of the detectable disease.

Typically, a therapeutically effective dosage is formulated to contain a concentration (by weight) of at least about 0.1% up to about 50% or more, and all combinations and sub-combinations of ranges therein. The compositions can be formulated to contain one or more compounds according to Formula I, or a pharmaceutically acceptable salt, polymorph or prodrug thereof in a concentration of from about 0.1 to less than about 50%, for example, about 49, 48, 47, 46, 45, 44, 43, 42, 41 or 40%, with concentrations of from greater than about 0.1%, for example, about 0.2, 0.3, 0.4 or 0.5%, to less than about 40%, for example, about 39, 38, 37, 36, 35, 34, 33, 32, 31 or 30%. Exemplary compositions may contain from about 0.5% to less than about 30%, for example, about 29, 28, 27, 26, 25, 25, 24, 23, 22, 21 or 20%, with concentrations of from greater than about 0.5%, for example, about 0.6, 0.7, 0.8, 0.9 or 1%, to less than about 20%, for example, about 19, 18, 17, 16, 15, 14, 13, 12, 11 or 10%. The compositions can contain from greater than about 1% for example, about 2%, to less than about 10%, for example about 9 or 8%, including concentrations of greater than about 2%, for example, about 3 or 4%, to less than about 8%, for example, about 7 or 6%. The active agent can, for example, be present in a concentration of about 5%. In all cases, amounts may be adjusted to compensate for differences in amounts of active ingredients actually delivered to the treated cells or tissue.

Although the invention finds application in humans, the invention is also useful for therapeutic veterinary purposes. The invention is useful for domestic or farm animals such as cattle, sheep, horses and poultry; for companion animals such as cats and dogs; and for zoo animals.

Pharmaceutical compositions may be formulated for any appropriate route of administration including, for example, topical (for example, transdermal or ocular), oral, buccal, nasal, vaginal, rectal or parenteral administration. The term parenteral as used herein includes subcutaneous, intradermal, intravascular (for example, intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. Within yet other embodiments, compositions provided herein may be formulated as a lyophilizate.

The various dosage units are each preferably provided as a discrete dosage tablet, capsules, lozenge, dragee, gum, or other type of solid formulation. Capsules may encapsulate a powder, liquid, or gel. The solid formulation may be swallowed, or may be of a suckable or chewable type (either frangible or gum-like). The present invention contemplates dosage unit retaining devices other than blister packs; for example, packages such as bottles, tubes, canisters, packets. The dosage units may further include conventional excipients well-known in pharmaceutical formulation practice, such as binding agents, gellants, fillers, tableting lubricants, disintegrants, surfactants, and colorants; and for suckable or chewable formulations.

Compositions intended for oral use may further comprise one or more components such as sweetening agents, flavouring agents, colouring agents and/or preserving agents in order to provide appealing and palatable preparations. Tablets contain the active ingredient in admixture with physiologically acceptable excipients that are suitable for the manufacture of tablets. Such excipients include, for example, inert diluents such as calcium carbonate, sodium carbonate, lactose, calcium phosphate or sodium phosphate, granulating and disintegrating agents such as corn starch or alginic acid, binding agents such as starch, gelatine or acacia, and lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent such as calcium carbonate, calcium phosphate or kaolin, or as soft gelatine capsules wherein the active ingredient is mixed with water or an oil medium such as peanut oil, liquid paraffin or olive oil.

Aqueous suspensions contain the active ingredient(s) in admixture with excipients suitable for the manufacture of aqueous suspensions. Such excipients include suspending agents such as sodium carboxymethylcellulose, methylcellulose, hydropropylmethylcellulose, sodium alginate, polyvinylpyrrolidone, gum tragacanth and gum acacia, and dispersing or wetting agents such as naturally-occurring phosphatides (for example, lecithin), condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol mono-oleate, or condensation products of ethylene oxide with partial esters derived from fatty acids and hexitol anhydrides such as polyethylene sorbitan monooleate. Aqueous suspensions may also comprise one or more preservatives, for example ethyl, or n-propyl p-hydroxybenzoate, one or more colouring agents, one or more flavouring agents, and one or more sweetening agents, such as sucrose or saccharin.

Oily suspensions may be formulated by suspending the active ingredients in a vegetable oil such as *arachis* oil, olive oil, sesame oil or coconut oil, or in a mineral oil such as liquid paraffin. The oily suspensions may contain a thickening agent such as beeswax, hard paraffin or cetyl alcohol. Sweetening agents such as those set forth above, and/or flavouring agents may be added to provide palatable oral preparations. Such suspensions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavouring and colouring agents, may also be present.

Pharmaceutical compositions may also be in the form of oil-in-water emulsions. The oily phase may be a vegetable oil such as olive oil or *arachis* oil, a mineral oil such as liquid paraffin, or a mixture thereof. Suitable emulsifying agents include naturally-occurring gums such as gum acacia or gum tragacanth, naturally-occurring phosphatides such as soy bean lecithin, and esters or partial esters derived from fatty acids and hexitol, anhydrides such as sorbitan monooleate, and condensation products of partial esters derived from fatty acids and hexitol with ethylene oxide such as polyoxyethylene sorbitan monooleate. An emulsion may also comprise one or more sweetening and/or flavouring agents.

Syrups and elixirs may be formulated with sweetening agents, such as glycerol, propylene glycol, sorbitol or sucrose. Such formulations may also comprise one or more demulcents, preservatives, flavouring agents and/or colouring agents.

Compounds may be formulated for local or topical administration, such as for topical application to the skin. Formulations for topical administration typically comprise a topical vehicle combined with active agent(s), with or without additional optional components.

For any of the fibrotic diseases described herein, when the compound of the present invention is topically administered to a human, the therapeutically effective amount of a compound corresponds to preferably between about 0.01 to about 10% (w/w), or between about 0.1 to 10% (w/w), or between about 1.0 to about 10% (w/w), between about 0.1 to about 5% (w/w), or between about 1.0 to about 5% (w/w). In any of fibrotic diseases described herein, when the compound of the present invention is orally administered to a subject, the therapeutically effective amount of a compound corresponds preferably between about 1 to about 50 mg/kg, or between about 1 to 25 mg/kg, or between about 1 to about 10 mg/kg, between about 5 to about 25 mg/kg, or between about 10 to about 20 mg/kg.

Suitable topical vehicles and additional components are well known in the art, and it will be apparent that the choice of a vehicle will depend on the particular physical form and mode of delivery. Topical vehicles include organic solvents such as alcohols (for example, ethanol, iso-propyl alcohol or glycerine), glycols such as butylene, isoprene or propylene glycol, aliphatic alcohols such as lanolin, mixtures of water and organic solvents and mixtures of organic solvents such as alcohol and glycerine, lipid-based materials such as fatty acids, acylglycerols including oils such as mineral oil, and fats of natural or synthetic origin, phosphoglycerides, sphingolipids and waxes, protein-based materials such as collagen and gelatine, silicone-based materials (both nonvolatile and volatile), and hydrocarbon-based materials such as microsponges and polymer matrices.

A composition may further include one or more components adapted to improve the stability or effectiveness of the applied formulation, such as stabilizing agents, suspending agents, emulsifying agents, viscosity adjusters, gelling agents, preservatives, antioxidants, skin penetration enhancers, moisturizers and sustained release materials. Examples of such components are described in Martindale—The Extra Pharmacopoeia (Pharmaceutical Press, London 1993) and Martin (ed.), Remington's Pharmaceutical Sciences. Formulations may comprise microcapsules, such as hydroxymethylcellulose or gelatine-microcapsules, liposomes, albumin microspheres, microemulsions, nanoparticles or nanocapsules.

A topical formulation may be prepared in a variety of physical forms including, for example, solids, pastes, creams, foams, lotions, gels, powders, aqueous liquids, emulsions, sprays and skin patches. The physical appearance and viscosity of such forms can be governed by the presence and amount of emulsifier(s) and viscosity adjuster(s) present in the formulation. Solids are generally firm and non-pourable and commonly are formulated as bars or sticks, or in particulate form. Solids can be opaque or transparent, and optionally can contain solvents, emulsifiers, moisturizers, emollients, fragrances, dyes/colorants, preservatives and other active ingredients that increase or enhance the efficacy of the final product. Creams and lotions are often similar to one another, differing mainly in their viscosity. Both lotions and creams may be opaque, translucent or clear and often contain emulsifiers, solvents, and viscosity adjusting agents, as well as moisturizers, emollients, fragrances, dyes/colorants, preservatives and other active ingredients that increase or enhance the efficacy of the final product. Gels can be prepared with a range of viscosities, from thick or high viscosity to thin or low viscosity. These formulations, like those of lotions and creams, may also contain solvents, emulsifiers, moisturizers, emollients, fragrances, dyes/colorants, preservatives and other active ingredients that increase or enhance the efficacy of the final product. Liquids are thinner than creams, lotions, or gels, and often do not contain emulsifiers. Liquid topical products often contain solvents, emulsifiers, moisturizers, emollients, fragrances, dyes/colorants, preservatives and other active ingredients that increase or enhance the efficacy of the final product.

Emulsifiers for use in topical formulations include, but are not limited to, ionic emulsifiers, cetearyl alcohol, non-ionic emulsifiers like polyoxyethylene oleyl ether, PEG-40 stearate, ceteareth-12, ceteareth-20, ceteareth-30, ceteareth alcohol, PEG-100 stearate and glyceryl stearate. Suitable viscosity adjusting agents include, but are not limited to, protective colloids or nonionic gums such as hydroxyethylcellulose, xanthan gum, magnesium aluminium silicate, silica, microcrystalline wax, beeswax, paraffin, and cetyl palmitate. A gel composition may be formed by the addition of a gelling agent such as chitosan, methyl cellulose, ethyl cellulose, polyvinyl alcohol, polyquaterniums, hydroxyethylceiluiose, hydroxypropylcellulose, hydroxypropylmethylcellulose, carbomer or ammoniated glycyrrhizinate. Suitable surfactants include, but are not limited to, nonionic, amphoteric, ionic and anionic surfactants. For example, one or more of dimethicone copolyol, polysorbate 20, polysorbate 40, polysorbate 60, polysorbate 80, lauramide DEA, cocamide DEA, and cocamide MEA, oleyl betaine, cocamidopropyl phosphatidyl PG-dimonium chloride, and ammonium laureth sulfate may be used within topical formulations.

Preservatives include, but are not limited to, antimicrobials such as methylparaben, propylparaben, sorbic acid, benzoic acid, and formaldehyde, as well as physical stabilizers and antioxidants such as vitamin E, sodium ascorbate/ascorbic acid and propyl gallate. Suitable moisturizers include, but are not limited to, lactic acid and other hydroxy acids and their salts, glycerine, propylene glycol, and butylene glycol. Suitable emollients include lanolin alcohol, lanolin, lanolin derivatives, cholesterol, petrolatum, isostearyl neopentanoate and mineral oils. Suitable fragrances and colours include, but are not limited to, FD&C Red No. 40 and FD&C Yellow No. 5. Other suitable additional ingredients that may be included in a topical formulation include, but are not limited to, abrasives, absorbents, anticaking agents, antifoaming agents, antistatic agents, astringents (such as witch hazel), alcohol and herbal extracts such as chamomile extract, binders/excipients, buffering agents, chelating agents, film forming agents, conditioning agents, propellants, opacifying agents, pH adjusters and protectants.

Typical modes of delivery for topical compositions include application using the fingers, application using a physical applicator such as a cloth, tissue, swab, stick or brush, spraying including mist, aerosol or foam spraying, dropper application, sprinkling, soaking, and rinsing. Controlled release vehicles can also be used, and compositions may be formulated for transdermal administration (for example, as a transdermal patch).

A pharmaceutical composition may be formulated as inhaled formulations, including sprays, mists, or aerosols. This may be particularly preferred for treatment of pulmonary fibrosis. For inhalation formulations, the composition or combination provided herein may be delivered via any inhalation methods known to a person skilled in the art. Such inhalation methods and devices include, but are not limited to, metered dose inhalers with propellants such as CFC or HFA or propellants that are physiologically and environmentally acceptable. Other suitable devices are breath operated inhalers, multidose dry powder inhalers and aerosol nebulizers. Aerosol formulations for use in the subject method typically include propellants, surfactants and co-solvents and may be filled into conventional aerosol containers that are closed by a suitable metering valve.

Inhalant compositions may comprise liquid or powdered compositions containing the active ingredient that are suitable for nebulization and intrabronchial use, or aerosol compositions administered via an aerosol unit dispensing metered doses. Suitable liquid compositions comprise the active ingredient in an aqueous, pharmaceutically acceptable inhalant solvent such as isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs. Suitable formulations, wherein the carrier is a liquid, for administration, as for example, a nasal spray or as nasal drops, include aqueous or oily solutions of the active ingredient.

Pharmaceutical compositions may also be prepared in the form of suppositories such as for rectal administration. Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

Pharmaceutical compositions may be formulated as sustained release formulations such as a capsule that creates a slow release of modulator following administration. Such formulations may generally be prepared using well-known technology and administered by, for example, oral, rectal or subcutaneous implantation, or by implantation at the desired target site. Carriers for use within such formulations are biocompatible, and may also be biodegradable. Preferably, the formulation provides a relatively constant level of modulator release. The amount of modulator contained within a sustained release formulation depends upon, for example, the site of implantation, the rate and expected duration of release and the nature of the condition to be treated or prevented.

In another embodiment there is provided a kit or article of manufacture including one or more AT2R agonists as described herein, or a pharmaceutically acceptable salt, polymorph or prodrug thereof and/or pharmaceutical composition as described above.

In other embodiments there is provided a kit for use in a therapeutic or prophylactic application mentioned above, the kit including:
    a container holding a therapeutic composition in the form of one or more AT2R agonists as described herein, or a pharmaceutically acceptable salt, polymorph or prodrug thereof or pharmaceutical composition;
    a label or package insert with instructions for use.

In certain embodiments the kit may contain one or more further active principles or ingredients for treatment of a fibrotic disease.

The kit or "article of manufacture" may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic or prophylactic composition can be used to treat a fibrotic disease described herein.

The kit may comprise (a) a therapeutic or prophylactic composition; and (b) a second container with a second active principle or ingredient contained therein. The kit in this embodiment of the invention may further comprise a package insert indicating the composition and other active principle can be used to treat a disorder or prevent a complication stemming from a fibrotic disease described herein. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain embodiments the therapeutic composition may be provided in the form of a device, disposable or reusable, including a receptacle for holding the therapeutic, prophylactic or pharmaceutical composition. In one embodiment, the device is a syringe. The device may hold 1-2 mL of the therapeutic composition. The therapeutic or prophylactic composition may be provided in the device in a state that is ready for use or in a state requiring mixing or addition of further components.

It will be understood, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient), and the severity of the particular disorder undergoing therapy.

TABLE 3

Summary Table listing profiles of key peptides. Data includes relative AT2R selectivity, binding potency ($IC_{50}$ values) and plasma stability.

| Agonist | Sequence | Fold AT2R selectivity | Binding AT1R IC50 (nM) | Binding AT2R IC50 (nM) | Plasma stability (t1/2 mins) |
|---|---|---|---|---|---|
| βArg-Ang II | Asp-β-Arg-Val-Tyr-Ile-His-Pro-Phe (SEQ ID NO: 5) | 123 | 275 | 2.24 | |
| βTyr-Ang II | Asp-Arg-Val-β-Tyr-Ile-His-Pro-Phe (SEQ ID NO: 5) | 3135 | >10,000 | 3.19 | |
| βIle-Ang II | Asp-Arg-Val-Tyr-β-Ile-His-Pro-Phe (SEQ ID NO: 5) | 943 | >10,000 | 10.6 | |
| βPro-Ang II | Asp-Arg-Val-Tyr-Ile-His-β-Pro-Phe (SEQ ID NO: 5) | 406 | 1000 | 2.46 | |
| βTyr-Ang III | Arg-Val-β-Tyr-Ile-His-Pro-Phe (SEQ ID NO: 6) | 5494 | >10,000 | 1.82 | |
| βPro-Ang III | Arg-Val-Tyr-Ile-His-β-Pro-Phe (SEQ ID NO: 6) | 21377 | >10,000 | 0.468 | 46 |
| βPhe-Ang III | Arg-Val-Tyr-Ile-His-Pro-β-Phe (SEQ ID NO: 6) | 492 | >10,000 | 20.3 | |
| βPro-Ang IV | Val-Tyr-Ile-His-β-Pro-Phe (SEQ ID NO: 7) | 738 | >10,000 | 13.5 | |
| βIle-8-Ang II | Asp-Arg-Val-Tyr-Ile-His-Pro-β-Ile (SEQ ID NO: 8) | 1300 | >10,000 | 7.7 | |
| βIle-8-Ang III | Arg-Val-Tyr-Ile-His-Pro-β-Ile (SEQ ID NO: 9) | 1040 | >10,000 | 9.6 | |
| D-Asp-β-Ile-Ang II | D-Asp-Arg-Val-Tyr-β-Ile-His-Pro-Phe (SEQ ID NO: 5) | 1590 | >10,000 | 6.3 | |

TABLE 3-continued

Summary Table listing profiles of key peptides. Data includes relative AT2R selectivity, binding potency (IC$_{50}$ values) and plasma stability.

| Agonist | Sequence | Fold AT2R selectivity | Binding AT1R IC50 (nM) | Binding AT2R IC50 (nM) | Plasma stability (t1/2 mins) |
|---|---|---|---|---|---|
| D-Arg-Ang III | D-Arg-Val-Tyr-Ile-His-Pro-Phe (SEQ ID NO: 6) | 400 | >10,000 | 25 | |
| D-Arg β-Pro-Ang III | D-Arg-Val-Tyr-Ile-His-β-Pro-Phe (SEQ ID NO: 6) | >300,000 | >100,000 | 0.324 | 1440 |
| βArg-Ala-8-Ang II | Asp-β-Arg-Val-Tyr-Ile-His-Pro-Ala (SEQ ID NO: 11) | 800 | >10000 | 12.5 | |
| βTyr-Ala-8-Ang II | Asp-Arg-Val-β-Tyr-Ile-His-Pro-Ala (SEQ ID NO: 11) | 330 | >10000 | 30.3 | |
| βPro-Ala-8-Ang II | Asp-Arg-Val-Tyr-Ile-His-β-Pro-Ala (SEQ ID NO: 11) | 434 | >10000 | 23.0 | |
| βArg-Ala-8-Ang III | β-Arg-Val-Tyr-Ile-His-Pro-Ala (SEQ ID NO: 12) | 1540 | >10000 | 6.5 | |
| βVal-Ala-8-Ang III | Arg-β-Val-Tyr-Ile-His-Pro-Ala (SEQ ID NO: 12) | 1234 | >10000 | 8.1 | |
| βPro-Ala-8-Ang III | Arg-Val-Tyr-Ile-His-β-Pro-Ala (SEQ ID NO: 12) | 200 | >10000 | 49.1 | |
| βArg-Trp-8-Ang III | β-Arg-Val-Tyr-Ile-His-Pro-Trp (SEQ ID NO: 10) | 1854 | 2503 | 1.348 | |
| βVal-Trp-8-Ang III | Arg-β-Val-Tyr-Ile-His-Pro-Trp (SEQ ID NO: 10) | 5037 | 1209 | 0.236 | |
| βTyr-Trp-8-Ang III | Arg-Val-β-Tyr-Ile-His-Pro-Trp (SEQ ID NO: 10) | >250,000 | >100000 | 0.384 | |
| βILe-Trp-8-Ang III | Arg-Val-Tyr-β-Ile-His-Pro-Trp (SEQ ID NO: 10) | >2500 | >100000 | 39.15 | |
| βPro-Trβ-8-Ang III | Arg-Val-Tyr-Ile-His-β-Pro-Trp (SEQ ID NO: 10) | >400,000 | >100000 | 0.236 | 167 |
| Pro-βTrp-8-Ang III | Arg-Val-Tyr-Ile-His-Pro-β-Trp (SEQ ID NO: 10) | 615 | 1933 | 3.136 | |
| Nic-βPro-Trp-8-Ang III | Nicotinamido-Arg-Val-Tyr-Ile-His-β-Pro-Trp (SEQ ID NO: 10) | >15,000 | 2945 | 0.19 | |
| Nic-βPro-Ang III | Nicotinamido-Arg-Val-Tyr-Ile-His-β-Pro-Phe (SEQ ID NO: 6) | >400,000 | >50,000 | 0.12 | |
| Tet-βPro-Trp-8-Ang III | Tetrazole-CONH-Arg-Val-Tyr-Ile-His-β-Pro-Trp (SEQ ID NO: 10) | >275,000 | >50,000 | 0.18 | |
| Tet-βPro-Ang III | Tetrazole-CONH-Arg-Val-Tyr-Ile-His-β-Pro-Phe (SEQ ID NO: 6) | >60,000 | >50,000 | 0.78 | |
| D-Arg-βPro-Trp-8-Ang III | D-Arg-Val-Tyr-Ile-His-β-Pro-Trp (SEQ ID NO: 10) | >18,000 | >50,000 | 2.82 | 1850 |
| NAc-βPro-Trp-8-Ang III | NAc--Arg-Val-Tyr-Ile-His-β-Pro-Trp (SEQ ID NO: 10) | >147,000 | >50,000 | 0.34 | 1550 |

TABLE 3-continued

Summary Table listing profiles of key peptides. Data includes relative AT2R selectivity, binding potency (IC$_{50}$ values) and plasma stability.

| Agonist | Sequence | Fold AT2R selectivity | Binding AT1R IC50 (nM) | Binding AT2R IC50 (nM) | Plasma stability (t1/2 mins) |
|---|---|---|---|---|---|
| Cholic Acid-βPro-Ang III | Cholate- Arg-Val-Tyr-Ile-His-β-Pro-Phe (SEQ ID NO: 6) | >200,000 | >50,000 | | 0.05 |

As shown above and herein, peptides may be referred to by the modifications and/or locations of those modifications relative to an Ang peptide, e.g. Arg-Val-Tyr-Ile-His-β-Pro-Trp (SEQ ID NO: 10) may be referred to as βPro7-Trp8-Ang III or ββPro-Trp-8-Ang III.

It will be understood that the invention disclosed and defined in this specification extends to all alternative combinations of two or more of the individual features mentioned or evident from the text or drawings. All of these different combinations constitute various alternative aspects of the invention.

It will be understood that these examples are intended to demonstrate these and other aspects of the invention and although the examples describe certain embodiments of the invention, it will be understood that the examples do not limit these embodiments to these things. Various changes can be made and equivalents can be substituted and modifications made without departing from the aspects and/or principles of the invention mentioned above. All such changes, equivalents and modifications are intended to be within the scope of the claims set forth herein.

EXAMPLES

There are 4 main sets of experiments described below and the results of which are shown here in the Examples and the Figures:

A) Radioligand binding studies are performed using non-selective iodinated compounds (such as $^{125}$I-AngII or $^{125}$I-Sar$^1$-Ile$^8$-AngII) that are able to bind to both AT1 and AT2Rs using HEK-293 cells transfected with either human AT1 or human AT2Rs. Typically, the ability of compounds of interest to displace the Ang II radioligand from both AT1 and AT2Rs will be determined. This will lead to the generation of IC50 values that determine the relative ability of test compounds to interact with both Angiotensin receptors.

B) Proteolytic stability was tested in a plasma stability assay used to assess the susceptibility of Ang II peptides to plasma proteases. A sample of rat plasma was incubated with peptide of interest (final concentration was 1 mg/mL; plasma diluted by 10% with peptide dissolved in saline). Protease activity was quenched in samples by the addition of acetonitrile, at selected time intervals. The amount of parent compound remaining at each time point was then assayed on an Agilent 1100 MSD SL ion trap mass spectrometer. The peaks observed in the resulting chromatograms were integrated, compared to a standard curve, and cross-checked by mass and retention time (Jones et al 2011 Hypertension. 57: 570-576).

C) In the intervention (or reversal) model, male FVB/N mice were treated with selective AT2Rs agonists after the establishment of cardiovascular disease using a high salt diet, in order to reverse cardiovascular pathologies. In some experiments, the ACE inhibitor captopril (dose) or the ARB candesartan cilexetil (dose) were given for 4 weeks in drinking water. Organs examined included heart, kidney and liver and these were compared to either untreated mice or high salt-fed mice that were treated with saline.

D) Human cardiac fibroblasts (HCFs) were treated with TGFβ1 to induce a pro-fibrotic phenotype state in cell culture, exemplified by increased collagen-1 production, measured by Western blot. HCFs were treated with TGFβ1 alone, or in the presence of an AT2R agonist for 3 days, and the ability of AT2R agonists to inhibit TGFβ1-induced collagen-1 production was measured.

Example 1

Animals, Drug Treatments and Surgical Procedures

Male FVB/N mice aged approximately 10-12 weeks were obtained from Monash Animal Research Laboratory. Animals were housed in the Animal House in the Department of Pharmacology, Monash University, in standard cages where they were initially maintained on a normal diet. The housing was maintained at roughly 21° C.±5° C. with mice exposed to a 12 hour light/dark cycle, and access to food and water ad libitum. Experimental procedures undertaken were approved and certified by the School of Biomedical Sciences (SOBS) Animal Ethics Committee of Monash University MARP/2013/118.

EXPERIMENTAL MODEL

A high-salt diet (5% salt) model is a clinically relevant and disease-reversal model which can replicate the high salt intake by humans which is currently a growing problem in the developed countries. High salt intake induces changes in the cardiovascular system and induces remodelling and fibrosis in the heart, kidney and liver.

Mice were placed on either a normal rodent diet (0.35% NaCl) which acted as control or a high salt diet (5% sodium in food chow) for 8 weeks. After 4 weeks, mice were also treated subcutaneously (via osmotic mini-pump) with either saline or an AT2R agonist (75 pmol/kg/min subcutaneously) for 4 weeks. Mice continued to be fed a high salt diet whilst receiving these treatments.

All mice which underwent surgery were anaesthetized with Isoflurane (Isorrane) (5% induction and 2.5% maintenance) and an incision made in the midscapular region through which osmotic minipumps (Alzet model 2004, Alza Corp) were inserted for subcutaneous drug administration. The incision area was sutured with 6/0 DY silk (Dynek Pty Ltd) and antibiotic powder applied (Cicatrin, Pfizer) followed by intramuscular injection of the analgesic Cartrophen (0.1 ml of a 1.5 mg/ml stock solution; Biopharm Australia). Systolic blood pressure (SBP) was measured using non-invasive tail-cuff plethysmography apparatus (MC4000 Blood Pressure Analysis System, Hatteras Instrument Inc) before drug treatment (week 0), and then fortnightly. At the end of the 8 week treatment period mice were weighed before being killed by overdose of isoflurane inhalation and cervical dislocation.

Organs (heart, kidneys, liver, aorta) were collected, with heart and aorta being dissected appropriately as described below. All organs were then snap frozen in liquid nitrogen, and stored at −80° C., unless otherwise stated.

The following procedures were conducted on organs harvested from the above experimental groups:

Cardiac Fibrosis Analysis

To measure collagen deposition, frozen sections of heart, kidney or aorta (all 5 μm thickness) were air dried for 10 minutes and were brought through 3 times xylene (2 minutes each), and 3 times absolute alcohol washes before being rinsed in tap $H_2O$ for 30 seconds. Staining with an optimal concentration of picrosirius red (in this instance 0.05% picrosirius red diluted in saturated picric acid) was performed and left for an hour. Sections were then rinsed in water and differentiated in 0.01M HCl for 2 minutes, followed by dehydration via 3 times absolute alcohol washes. Then, slides were brought through 3 times xylene washes before being cover slipped according to standard histological techniques using DPX as the mounting medium. Images were taken under ×20 magnification, using bright field (Olympus, BX51) and circularized polarized light microscopy (DM IRB, Leica) while percentage of positive interstitial collagen staining per total field of view was quantified using ImageJ 1.46 software (Java, NIH), and averaged out from a total of eight views as the final percentage collagen content in a particular animal.

Kidney Fibrosis Analysis

Kidney sections used either picrosirius red staining as described above or using Mason's Trichrome staining as described below.

Formalin fixed, paraffin embedded kidneys were sectioned at thickness of 4 μm and were stained with Masson's trichrome according to standard procedures for analysis of kidney fibrosis. Initially sections were deparaffinised and rehydrated through 100% alcohol, 95% alcohol and 75% alcohol washes then washed in distilled water. Sections were re-fixed in Bouin's solution for 1 hour at 56° C. to improve staining quality then rinsed in running tap water for 5-10 minutes to remove yellow colour. Following this, sections were stained in Weigert's iron hematoxylin working solution for 10 minutes. Rinsed in running warm tap water for 10 minutes. Washed in distilled water. Stained in Biebrich scarlet-acid fuchsin solution for 10-15 minutes. Washed in distilled water. Differentiated in phosphomolybdic-phosphotungstic acid solution for 10-15 minutes or until collagen was no longer red. Sections were transferred directly (without rinse) to aniline blue solution and stained for 5-10 minutes. Rinsed briefly in distilled water and differentiated in 1% acetic acid solution for 2-5 minutes. Washed in distilled water. Dehydrated very quickly through 95% ethyl alcohol, absolute ethyl alcohol and clear in xylene. Mounted with DPX mounting medium.

Quantification of kidney fibrosis was performed using images captured with the Aperio scanner (Monash Histology Platform, Monash University), with ×5 magnification. Each kidney section had 5 different fields of view photographed at this magnification. Percentage of tubulointerstitial collagen was analysed and quantified using ImageJ 1.48 software (Java, NIH), and the percentage from 5 random fields of view were averaged for final percentage of collagen for that particular animal. All analysis of collagen expression was conducted in a blinded fashion.

Liver Fibrosis Analysis

Liver sections used either picrosirius red staining or Masson's trichome staining as described above. Higher concentrations of picrosirius red were often used under polarized light microscopy. The liver was removed and sectioned with half of the liver placed in 10% formalin and the rest frozen in liquid nitrogen before being stored in ~80° C. freezer for future use. Formalin fixed, paraffin embedded livers were sectioned at thickness of 4 μm and were stained with Masson's trichrome according to standard procedures for analysis of liver fibrosis. Initially sections were deparaffinised and rehydrated through 100% alcohol, 95% alcohol and 75% alcohol washes then washed in distilled water. Sections were re-fixed in Bouin's solution for 1 hour at 56° C. to improve staining quality then rinsed in running tap water for 5-10 minutes to remove yellow colour. Following this, sections were stained in Weigert's iron hematoxylin working solution for 10 minutes. Rinsed in running warm tap water for 10 minutes. Washed in distilled water. Stained in Biebrich scarlet-acid fuchsin solution for 10-15 minutes. Washed in distilled water. Differentiated in phosphomolybdic-phosphotungstic acid solution for 10-15 minutes or until collagen was no longer red. Sections were transferred directly (without rinse) to aniline blue solution and stained for 5-10 minutes. Rinsed briefly in distilled water and differentiated in 1% acetic acid solution for 2-5 minutes. Washed in distilled water. Dehydrated very quickly through 95% ethyl alcohol, absolute ethyl alcohol and clear in xylene. Mounted with DPX mounting medium. Quantification of liver fibrosis was performed using images captured with the Aperio scanner (Monash Histology Platform, Monash University), with ×5 magnification. Each liver section had 5 different fields of view photographed at this magnification. Percentage of interstitial and perivascular collagen was analysed and quantified using ImageJ 1.48 software (Java, NIH), and the percentage from 5 random fields of view were averaged for final percentage of collagen for that particular animal. All analysis of collagen expression was conducted in a blinded fashion.

Immunohistochemical Localization of Fibrotic and Inflammatory Markers

Immunostaining was performed on 5 μm thick transverse frozen heart sections. These sections were air dried and fixed in ice-cold acetone for approximately 15 minutes before washing with 0.01M PBS buffer (3×10 minutes). Sections were then incubated with 10% goat serum in 0.01M PBS for 30 minutes to reduce non-specific binding. If the primary antibody is raised in goat, this pre-blocked medium is substituted with 5% BSA in PBS and Triton-X. Next, blocking buffers were removed and the primary antibody to respective markers were applied overnight at room temperature based on the following dilution and origin of the antibodies: α-SMA (1:500, Abcam), Vimentin (1:500, Santa Cruz), P-IκBα (1:200, Cell Signalling), F4/80 macrophage (1:100, Serotec). After 4 series of washes in ice-cold PBS on second day, appropriate secondary antibodies were incubated with mainly Alexa 488 (Invitrogen or Abcam), Alexa 594 (Invitrogen) and Fluorescein FI-5000 (Vector) being used. With primary antibodies raised in mouse, another immunofluorescence technique was performed using the mouse on mouse (M.O.M) kit (Vector) on heart sections based on the following dilution and origin of the antibodies: TGF-β (1:50, Santa Cruz), ICAM-1 (1:100, Santa Cruz). All immunofluorescent sections were viewed under ×20 magnification on an Olympus, BX51 microscope and images analyzed using Image J.

Determination of Tissue Protein Expression by Western Blot Analysis

Total proteins from homogenized ventricles were extracted using 1.5× Laemmli buffer containing 25% Glycerol, 7.5% SDS, 250 mM Tris-HCl at pH 6.8, and 0.001 g bromophenol blue. Homogenized samples were sonicated followed by heating at 37° C. for 20 minutes and centrifuged at 13,000 rpm for 30 minutes at 4° C. RCDC assay was performed and the protein content was quantified using ProteinQuant-Lowry software (SoftMax Pro) at 750 nm. Finally, samples were stored at −20° C. Western blot was performed firstly with samples (10 or 25 μg/μl/sample) being electrophoresed, transferred, and probed with primary antibody such as TGF-β (25 kDA, 1:2000, Santa Cruz), collagen-1, MMP-13 (54 kDA, 1:100, Abcam), ICAM-1 (85-110 kDA, 1:200, Santa Cruz), GAPDH (36 kDA, 1:20000, Abcam). The secondary antibodies were HRP-conjugated goat anti-mouse IgG (1:10000, Jackson ImmunoResearch) or anti-rabbit IgG (1:10000, DAKO), followed by development with ECL reagent. Membranes were exposed to CLx-Posure film (Pierce, Rockford, Ill.). Immunoreactive bands were then quantified using chemiDoc XRS imager and Quantity One software (BioRad). Individual bands were quantified using bands intensity per area and were then normalized to the intensity per area of the housekeeping gene GAPDH.

Human Cardiac Fibroblast Cell Culture Studies

Commercially available human cardiac fibroblasts (HCF, Catalog #6300, Sciencell, Calif., USA) were grown in T75 flask maintained in an incubator at 37° C., 5% $CO_2$. Complete media composition: M199 media (#11150-059, life technologies)+10% FBS (#10437-028, life technologies)+1% Fibroblast Growth Supplement-2 (#2382, ScienCell)+1% penicillin/streptomycin 10,000 U/ml antibiotics (#15140-122, Life Technologies). Fresh complete media was replenished every alternate day until culture reached 70% confluence in which media is replenished daily until it reached approximately 90% confluence in order to passage/subculture. To subculture, media was discarded and culture was rinsed with warm PBS. After which, culture was detached using warm 0.05% Trypsin+EDTA with gentle swirling of flask to make sure cells were not adherent to surface of flask. Trypsin was then neutralized with complete media and suspension was then transferred into a new falcon tube and centrifuged at 1000 rpm for 5 minutes. Supernatant was discarded and pellet of cells were resuspended with 5 ml of complete media, followed by cell counting. For subculturing/passaging, 1 million HCFs are placed into a T75 flask. For Picrosirius Red (PSR) staining or immunofluorescence experiments, 100 k cells were loaded per well in a 24 well plate lined with round coverslips. For western blot analysis experiments, 100 k cells were loaded per well in a 12 well plate. Passage 3-6 cells had been used for experiments with the pro-fibrotic agents added in complete media at the time when cells were being passaged and plated. All duration of treatment was approximately 72 hours. Once treatment is done, media was collected and cells were treated differently depending on the type of experiments as follow:

Picrosirius Red (PSR) Staining

Cells were initially grown on coverslips, washed with warm PBS once and fixed in ice-cold methanol overnight at −20° C. The next day, methanol was discarded and cells were washed once with cold PBS and incubated with 0.1% PSR solution for 1 hour at room temperature. After this, the dye was removed and cells were washed 3 times with 0.1% acetic acid, followed by dehydration with 3 changes of 100% ethanol (5 minutes each) and 3 times with xylene (10 minutes each). Coverslips were removed and mounted on slides using DPX mounting medium.

Immunofluorescence

Cells were grown on coverslips, washed with warm PBS once and fixed in ice-cold acetone for 5 minutes at −20° C. Once acetone was discarded, cells were rinsed in PBS, 3×10 minutes at room temperature. Cells were then blocked with 10% goat serum for 30 minutes at room temperature, followed by overnight incubation with primary antibody (1:500 dilution) at 4° C. The next day, primary antibody was removed and cells were rinsed with PBS 3×10 minutes at room temperature. Cells were then incubated with secondary antibody (1:500 dilution) for 2 hours at room temperature. Cells were then again rinsed with PBS 3×10 minutes at room temperature. Coverslips were removed from 24 well plate and mounted on slides using Vectashield mounting medium with DAPI, left to dry prior to imaging under confocal microscope.

Western Blot Analysis i. Protein Extraction:

Once treatment is complete, cells were washed with warm PBS and detached using Accutase (A6964, Sigma), with 5 minutes incubation at 37° C. Cells were then collected and centrifuged at 7000 rpm for 5 minutes at 4° C. During this time, 1×RIPA lysis buffer cocktail was prepared fresh. After centrifugation, supernatant was discarded. Cell pellet was then lysed in 20 ul of 1×RIPA lysis buffer cocktail and kept on ice for 30 minutes. After that, the cell lysate was centrifuged at 13200 rpm for 10 min at 4° C. to pellet nuclei and any insoluble cell debris. The supernatant (~20 ul) was transferred to a new tube and protein concentrations were measured using Biorad Lowry protein assay. Protein quantification of respective markers were performed via standard western blot analysis.

ii. Western Blotting:

10% gels (15 wells) were made up using TGX Stain-Free FastCast Acrylamide starter kit, 10% (#161-0183, Biorad). Samples were prepared by diluting 3 parts sample with 1 part of 4× sample buffer, ie. add 10 ul of extracted protein samples (half of total extracted proteins) into 3.3 ul of 4× Laemli sample buffer (#161-0747, Biorad). Keep samples on ice at all times up till this step. Boil samples at 95° C. for 5 minutes. Load all samples onto the 15 wells gel, along with a protein ladder. Make up 1× Running buffer from 10× buffer (#161-0732, Biorad). Top up tank and run samples at 200V for ~40 mins-1 hour. Terminate gel electrophoresis once the desired protein bands have been separated appropriately. Prepare sandwich stacks and membrane (pre-soak membrane in methanol for ~10 s), then soak them all in 1× Trans-Blot Turbo Transfer buffer (#170-4272). Lay a stack of wetted stack on bottom of cassette (bottom ion reservoir stack), followed by wetted membrane, then the gel and lastly with another wetted transfer stack at the top (top ion reservoir stack). Roll the assembled sandwich with blot roller to expel trapped air bubbles. Close and lock cassette lid and insert cassette in the Transfer-Blot Turbo transfer system and begin transfer. Once transfer is completed, wash membranes briefly in TBS-T (0.1% Tween-20 in 1×TBS). Block membranes in blocking buffer (TBS-T/5% skim milk; 5 g/100 ml) for at least 1 hour at room temperature on a mechanical shaker. Replace and incubate the membrane overnight with primary antibody at 4° C. Next day, wash membrane 3×15 minutes in TBS-T. Incubate secondary antibody in 5% skim milk for 1 hour at room temperature on shaker. Wash 3×15 minutes in TBS-T. Incubate membrane with ECL substrate for 5 minutes. Image the membrane with a digital imager ChemiDoc MP imaging system. Bands were analyzed using Image Lab software. Marker of interest such as α-smooth muscle actin (α-SMA) and collagen type I were quantified against housekeeping gene GAPDH. All protein expressions were assessed as a relative ratio to the control group.

Statistical Analysis

Results were expressed as mean±standard error of mean (SEM). All statistical plots and analysis were performed using the Prism program (GraphPad Software Inc. SanDiego, Calif., USA). All statistical comparisons (collagen deposition, all IHC quantifications and western blot analysis) between normal-salt and high-salt treatment alone or in the presence of drug treatment, was conducted using one-way analysis of variance (ANOVA) followed by post-hoc Tukey's corrections for multiple comparisons.

Example 2

Synthesis of Compounds
General Information

Fmoc-protected α-amino acids, β-amino acids, 2-(1H-7-Azabenzotriazol-1-yl)-1,1,3,3-tetramethyl uronium hexafluorophosphate (HATU), O-benzotriazole-N,N,N',N'-tetramethyl-uronium-hexafluoro-phosphate (HBTU), N-hydroxybenzotriazole (HoBt), and Wang resin were purchased from GL Biochem (Shanghai, China). Dimethylformamide (DMF, stored over 4 Å MS), N-methyl-2-pyrrolidone (NMP), dichloromethane ($CH_2Cl_2$, distilled from $P_2O_5$ and stored over 4 Å MS), and piperidine were purchased from Merck (Darmstadt, Germany). Trifluoroacetic acid (TFA) and diisopropylethylamine (DIPEA) were purchased from Auspep (Melbourne, Australia). All other reagents were purchased from Sigma-Aldrich.

Peptide Synthesis

All Angiotensin peptides were synthesized using standard Fmoc chemistry on Wang resin (0.9 mmol/g loading, GL Biochem, Shanghai, China). The resin was washed (3×30 s) with NMP and the Fmoc-protected amino acid (3.1 eq. to resin loading) was dissolved in NMP along with HBTU (3 eq. to resin loading), HoBt (3 eq. to resin loading) and DIPEA (4.5 eq. to resin loading). 4-Dimethylaminopyridine (0.1 eq. to resin loading) in NMP was added dropwise and the reaction proceeded overnight.

At this stage peptide synthesis of all peptides proceeded as normal. Thus, following the overnight coupling, the resin was washed with NMP (5×30 s) and $CH_2Cl_2$ (5×30 s) and peptide synthesis was continued. One cycle of peptide elongation consisted of the following steps. The loaded resin was first washed with NMP (3×30 sec) and the terminal Fmoc protecting group was removed with 20% piperidine/DMF (2×15 min). The deprotected resin was then washed with NMP (5×30 s) and treated for 60 min with a solution containing 3.1 eq. of the appropriate amino acid, 3 eq. HATU, and 4.5 eq. DIPEA. The resin was then washed three times with NMP (3×30 s), unreacted amino groups were acetylated upon treatment with 10% v/v acetic anhydride and 1% v/v DIPEA in NMP (2×20 min), and the capped resin washed with NMP (3×30 s). These steps were repeated until the peptide sequence was complete. Once the final Fmoc-protecting group had been removed, the resin was subsequently washed with NMP (5×30 s) and $CH_2Cl_2$ (5×30 s), dried for 20 min under vacuum, and then treated for 120 min with a cleavage solution containing 2.5% v/v water and 2.0% v/v triisopropylsilane and 0.5% v/v ethanedithiol in TFA. The cleaved resin was washed twice with the cleavage solution (2×30 s) and the cleaved peptide in TFA was collected. The TFA was evaporated under a stream of $N_2$ and the peptide was precipitated by the addition of diethyl ether. The precipitate was filtered and reconstituted in $H_2O$/acetonitrile (1:1) for lyophilization.

Peptide Purification and Analysis

Mass spectra were acquired with an Agilent 1100 MSD SL ion trap mass spectrometer. Reverse-phase HPLC was performed using an Agilent HP1200 system fitted with a Vydac™ analytical (C18, 300 Å, 5 μm, 4.6 mm×150 mm) or preparative (C18, 300 Å, 5 μm, 10 mm×250 mm) columns. Preparative HPLC columns were heated to 60° C. in a water bath. The eluents were 0.1% aqueous TFA and 0.1% TFA in acetonitrile.

The success of each synthesis was assessed first by HPLC and ESI-MS analysis of the crude reaction mixture. Peptides were then purified to homogeneity by reverse-phase HPLC. The identities and purities of purified peptides were assessed by analytical HPLC and mass spectrometry. HPLC retention times were observed following analytical HPLC with a solvent gradient of 0-50% 0.1% acetonitrile over 45 min.

Angiotensin AT1 and AT2R Radioligand Binding Assays

HEK-293 stably transfected with either AT1R or the AT2R (Jones et al 2011, supra) were used for binding studies, as described previously (Bosnyak S et al 2011; Clinical Science 121: 297-303; Del Borgo M et al 2015; Clinical Science 129: 505-513). Cells were grown to approximately 80% confluence before being re-plated into 48 well plates at 1×105 cells/well and grown for 48 hours at 37° C. for a whole cell competition binding assay. [125I]-Sar1Ile8Ang II at 50,000 cpm, incubated for 45 minutes at 37° C., in the absence or presence of unlabeled ligands, prepared in binding buffer (DMEM, 0.1% BSA), were used in the competition assays at concentrations ranging from 1 μM to 10 μM. For each experiment, each ligand concentration was tested in duplicate or triplicate, and each experiment was repeated at least 3 separate times. Non-specific binding (NSB) was defined in the presence of the unlabeled Ang II (10 μM). The ability of each ligand to inhibit specific binding of [125I]-Sar1Ile8Ang II was measured on a gamma counter with all counts corrected for NSB. Non-linear regression of the data using one-site fit model was performed and IC50 values, representing the concentration at which each ligand displaced 50% of [125I]-Sar1Ile8Ang II binding, were calculated as affinity estimates for each ligand at AT1R and AT2R, using GraphPad Prism 6 (GraphPad Software Inc., San Diego, Calif., USA).

Collectively, the studies in the Examples below show that AT2R stimulation has dramatic effects on organ fibrosis, particularly in the heart and kidney, and have also identified a novel inhibitory effect on liver steatosis.

Example 3

Figure 1:
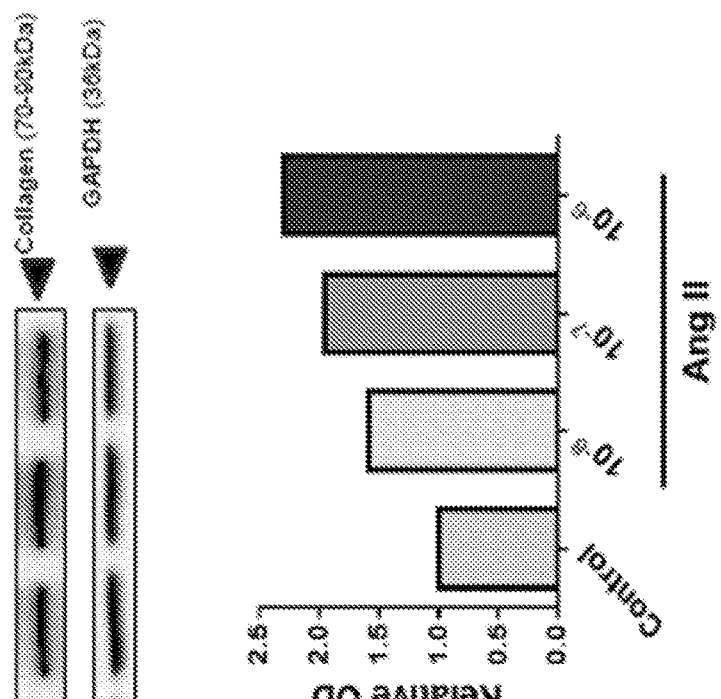
FIG. 1: Pro-fibrotic effect of the non-selective AT1/AT2R agonist Angiotensin II (Ang II) in human cardiac fibroblasts. Left panel: Representative images showing that Ang II caused myofibroblast differentiation, indicated by increased expression of α-SMA (red: α-SMA-marker for myofibroblasts; blue: DAPI-marker for nuclei). Right panel: Images and mean data from western blots confirming dose-dependent increases in protein expression of collagen when human cardiac fibroblasts (HCFs) were treated with Ang II with varying concentrations for 3 days.
Figure 1:
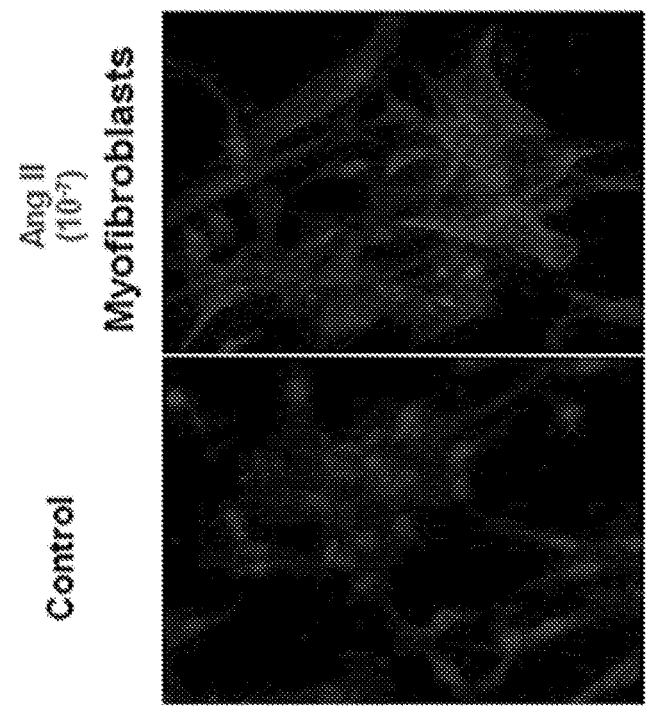

Studies were performed to examine the use of human cardiac fibroblasts (HCFs) as a potential in vitro model of fibrosis in order to test novel compounds prior to in vivo analysis. The endogenous octapeptide Ang II clearly exerts a predominant effect on AT1R as it caused a pro-fibrotic phenotype. FIG. 1 shows that Ang II caused myofibroblast differentiation, indicated by increased expression of α-SMA (red: α-SMA-marker for myofibroblasts; blue: DAPI-marker for nuclei). Such changes enable the HCFs to secrete more collagen, as noted by the concentration-dependent increase in collagen produced by HCFs in cell culture (measured by Western blot) in response to Ang II incubation for 72 hours.

AT1R and AT2R are Expressed on HCFs

Figure 2:
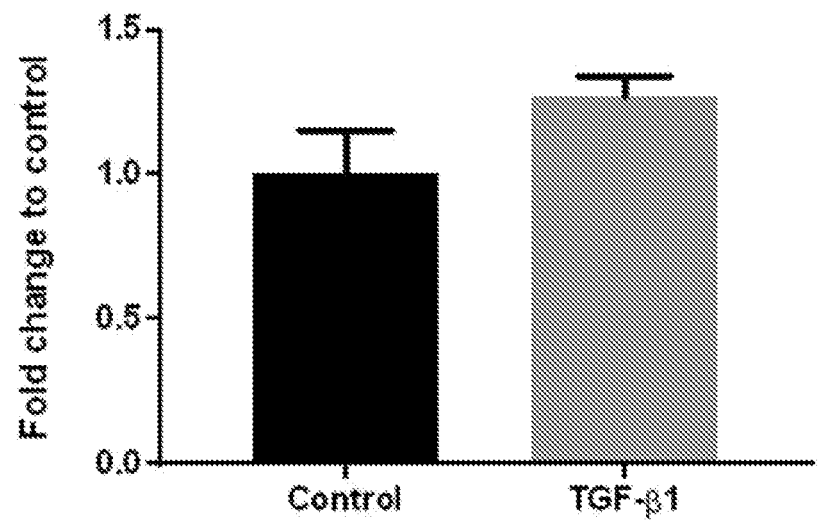
FIG. 2: TGF-β1 differentially affects the mRNA expression of $AT_1R$ and $AT_2R$ in human cardiac fibroblasts. Quantitative qPCR data showing that both $AT_1R$ and $AT_2R$ are expressed in human cardiac fibroblasts. TGF-β1 (5 ng/ml for 72 hours) increased AT2R mRNA expression but not $AT_1R$ mRNA expression. Quantitative values were obtained from the threshold cycle (Ct) number. Target gene expression level was normalized against beta-actin mRNA expression for each sample and data was expressed relative to the control. Data expressed as mean±sem relative to untreated HCFs; *$P<0.05$ versus untreated control (t-test).
Figure 2:
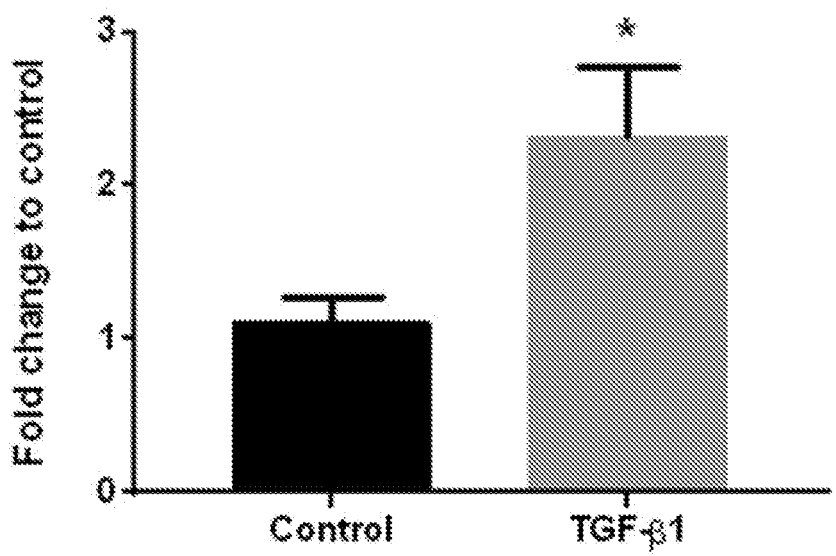

The mRNA of both Ang receptor subtypes was confirmed by quantitative PCR as shown in FIG. 2. Moreover, 72-hour incubation with the pro-fibrotic agent TGF-β1 resulted in an increase in AT2R mRNA expression but not AT1R expression, which is analogous to the upregulation of AT2R expression that is often reported following tissue injury, e.g. after myocardial infarction/heart failure.

AT2R Selectivity Determines Anti-Fibrotic Activity in HCFs

Figure 3:
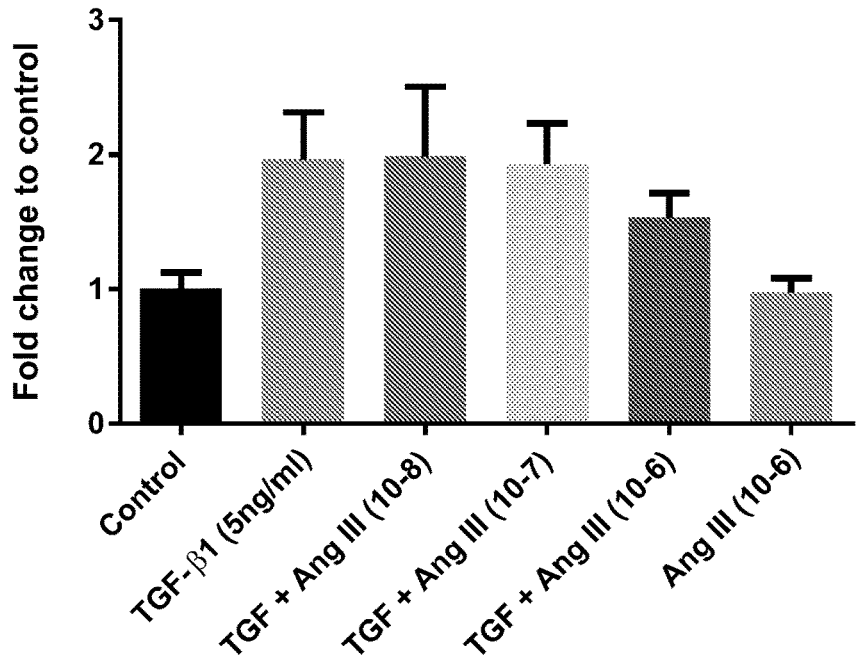
FIG. 3: Effects of relative selectivity of AT2R agonists on collagen production induced by TGFβ1 in human cardiac fibroblasts. Quantitative western blot data showing protein expression of collagen when HCFs were co-treated with TGF-β1 together with increasing concentrations of Ang III, β-Val$^3$-Ang II, or β-Arg$^2$-Ang II (n=3-4). Data expressed as mean±s.e.m; densitometric analysis of western blots expressed as relative ratio to mean of untreated HCFs; #$P<0.05$ versus control; *$P<0.05$ versus TGF-β1 (one way ANOVA with Tukey's correction for multiple comparisons). Ang III, β-Val$^3$-Ang II, and β-Arg$^2$-Ang II exhibit AT2/AT1R selectivity ratios of approx. 30, 48 and 123, respectively. Given that β-Arg$^2$-Ang II was the only compound to significantly reduce TGF-β1-evoked collagen production, it is estimated that an AT2R/AT1R selectivity ratio >100 is required for anti-fibrotic efficacy.
Figure 3:
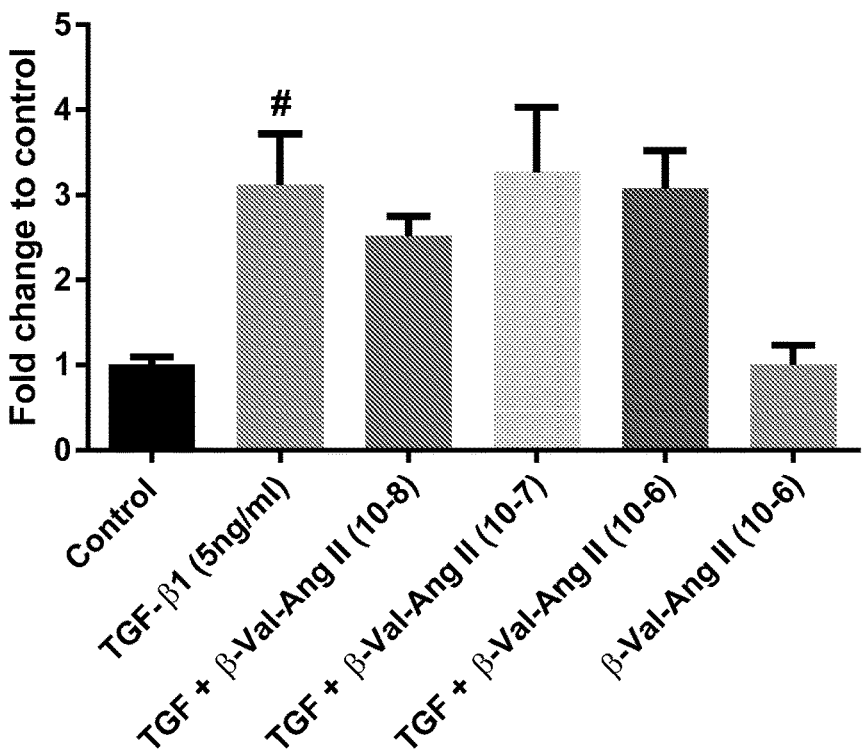
Figure 3:
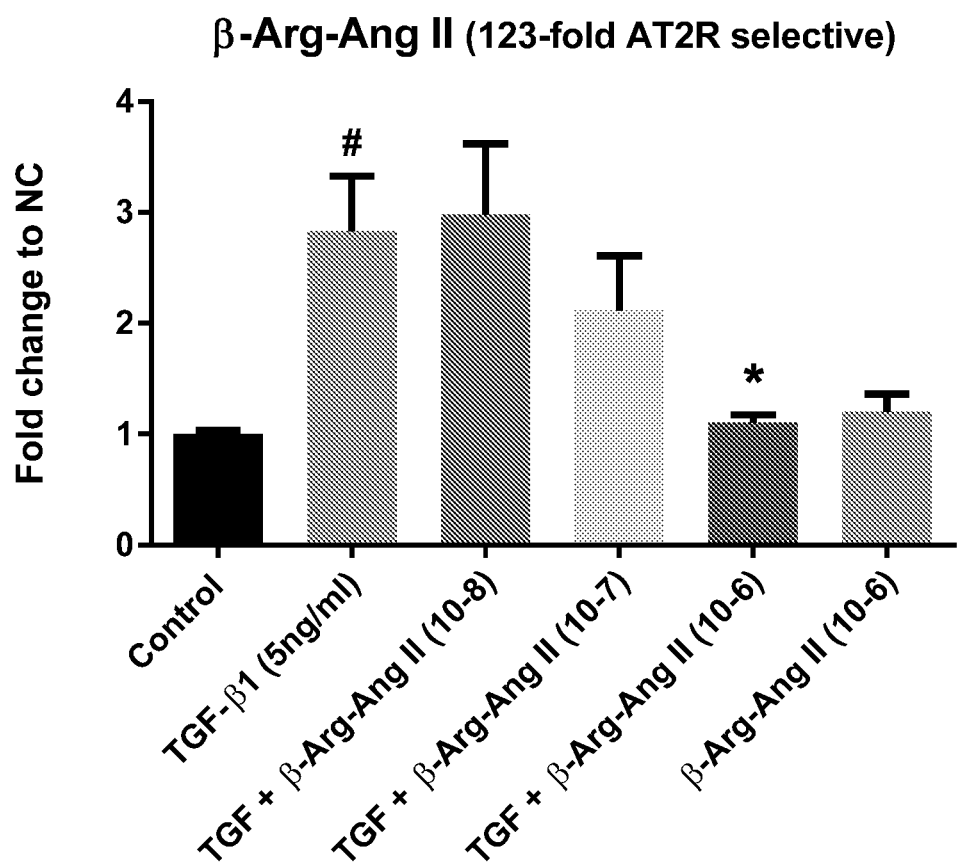
Figure 4:
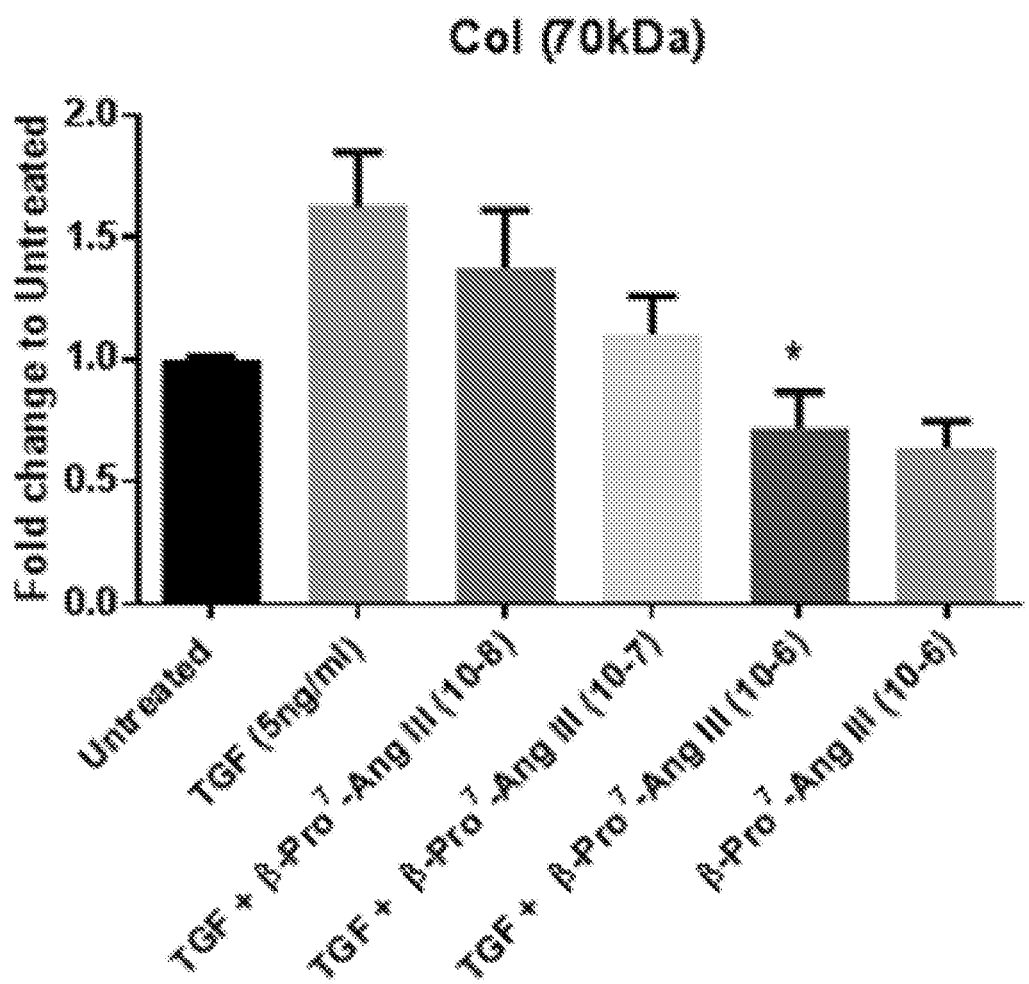
FIG. 4: Highly selective AT2R agonist, β-Pro$^7$-Ang III, decreased collagen production induced by TGFβ1 in human cardiac fibroblasts. Quantitative western blot data showing dose-dependent decreases in protein expression of collagen when HCFs were co-treated with TGFβ1+ increasing concentrations of β-Pro$^7$-Ang III (n=4-5). Data expressed as mean±s.e.m; densitometric analysis of western blots expressed as relative ratio to mean of untreated HCFs; *$P<0.05$ versus TGFβ1 (one way ANOVA with Tukey's correction for multiple comparisons). β-Pro$^7$-Ang III has an approx. AT2R/AT1R selectivity of approx. 20,000.

A number of novel Ang peptides have been examined in HCFs stimulated with TGF-β1 for 3 days, in order to determine the approximate AT2R selectivity required to evoke anti-fibrotic effects (see FIG. 3). For example, the endogenous heptapeptide Ang III which exhibits minimal selectivity for AT2R over AT1R (~15-30-fold) failed to inhibit TGF-β1-induced collagen 1 formation (quantified by Western blot) when tested up to 1 μM (FIG. 3). Similarly, β-Val$^3$-Ang II, which only has ~50-fold AT2R:AT1R selectivity also failed to inhibit the TGFβ1-mediated pro-fibrotic phenotype in HCFs (FIG. 3). However, another compound tested, β-Arg$^2$-Ang II, which has ~120-fold AT2R:AT1R selectivity inhibited the TGF-β1-mediated pro-fibrotic phenotype (FIG. 3). As expected, the approx. 20,000-fold selective AT2 receptor agonist, β-Pro$^7$-Ang III decreased collagen production induced by TGF-β1 in human cardiac fibroblasts (FIG. 4).

Thus, the inventors have tested a number of β-substituted Ang peptides for the first time for their ability to inhibit collagen production in HCFs. Collectively, this analysis has determined that (i) an AT2R:AT1R ratio of >100 is required for some concentration-dependent anti-fibrotic effects in HCFs and (ii) selective AT2R agonists do not cause pro-fibrotic effects even at up to 1 μM, unlike the effect of the endogenous peptide parent hormone Ang II (FIG. 1) that is also largely responsible for AT1R-mediated pro-fibrotic, pro-inflammatory, pro-oxidative stress effects in the body. AT1Rs are ubiquitously expressed in the cardiovascular and renal system, and provide the anatomical framework for excitatory cardiovascular effects of Ang II that increase the risk of a cardiovascular or renal event. Therefore, compounds with an AT2R:AT1R selectivity ratio of at least 100, may be required in vivo to avoid confounding effects of AT1R stimulation.

Example 4

Following on from the in vitro cell culture studies (Example 3) showing that AT2R stimulation could prevent TGF-β1-mediated collagen formation, this example provides in vivo proof-of-principle that chronic AT2R stimulation with novel peptidergic compounds reversed established organ fibrosis (e.g. heart, kidney, liver) in mice. To this end, modified Ang peptides of interest were dissolved in saline and delivered subcutaneously via an implanted osmotic minipump and systolic blood pressure (SBP) was measured fortnightly.

Chronic AT2R Stimulation Using β-Ile$^5$-Ang II Reverses Established Organ Fibrosis Induced by High Salt Diet.

For these studies, male FVB/N mice (~10-15 weeks old) were placed on a high salt (5% NaCl) chow diet for 8 weeks. This type of dietary intervention was used to mimic a general Western diet and leads to pro-inflammatory and pro-fibrotic changes in tissue causing extracellular matrix (ECM) remodelling resulting in collagen deposition in many organs, notable heart and kidney. In this model, there is minimal change in basal blood pressure. After 4 weeks of high salt diet, cardiac fibrosis has plateaued and is similar when measured after 8 weeks of high salt diet. Therefore, the inventors used an intervention protocol in which our drug treatments were commenced for the final 4 weeks of the protocol when cardiac fibrosis was already established.

Figure 5:
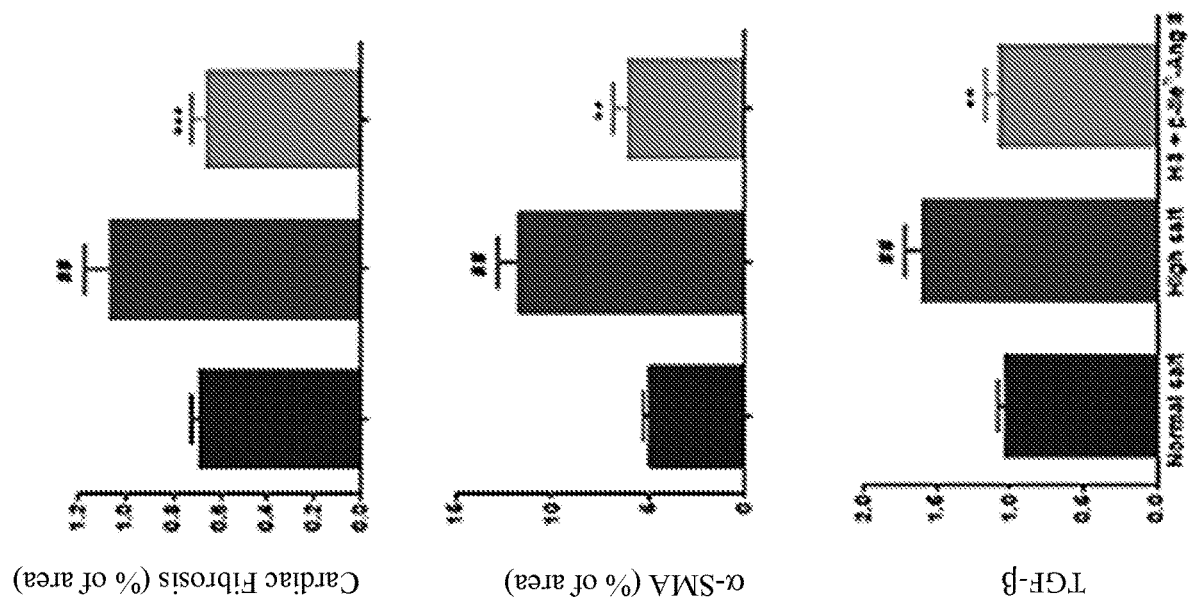
FIG. 5: AT2R stimulation by β-Ile$^5$-Ang II attenuates high salt (5%)-mediated fibrosis and myofibroblast differentiation in mouse heart. Left panel: Representative images are shown of transverse heart sections stained for collagen using picrosirius red (PSR) or an antibody against α-smooth muscle actin (α-SMA), taken from male FVB/N mice that were untreated (top); fed a high salt diet for 8 weeks (8W HS) or received β-Ile$^5$-AngII (75 pmol/kg/min subcutaneously via osmotic mini-pump) during weeks 5-8 while on a high salt diet (bottom). Right panel: Mean data for cardiac fibrosis determined by PSR (top); myofibroblast differentiation determined by α-SMA (marker for myofibroblast expression; middle), or western blot analysis of the pro-fibrotic cytokine marker, transforming growth factor-β1(TGF-β) (bottom); all of which shows that β-Ile$^5$-Ang II inhibits pro-fibrotic effects of high salt in the heart. Data expressed as mean±s.e.m of percentage positive stained area for fibrosis and α-SMA, while western blot protein data is expressed as a ratio relative to normal-salt group (n=5-8). ##P<0.01 versus normal salt; P<0.01; *P<0.001 versus high salt (one way ANOVA with Tukey's correction for multiple comparisons).
Figure 5:
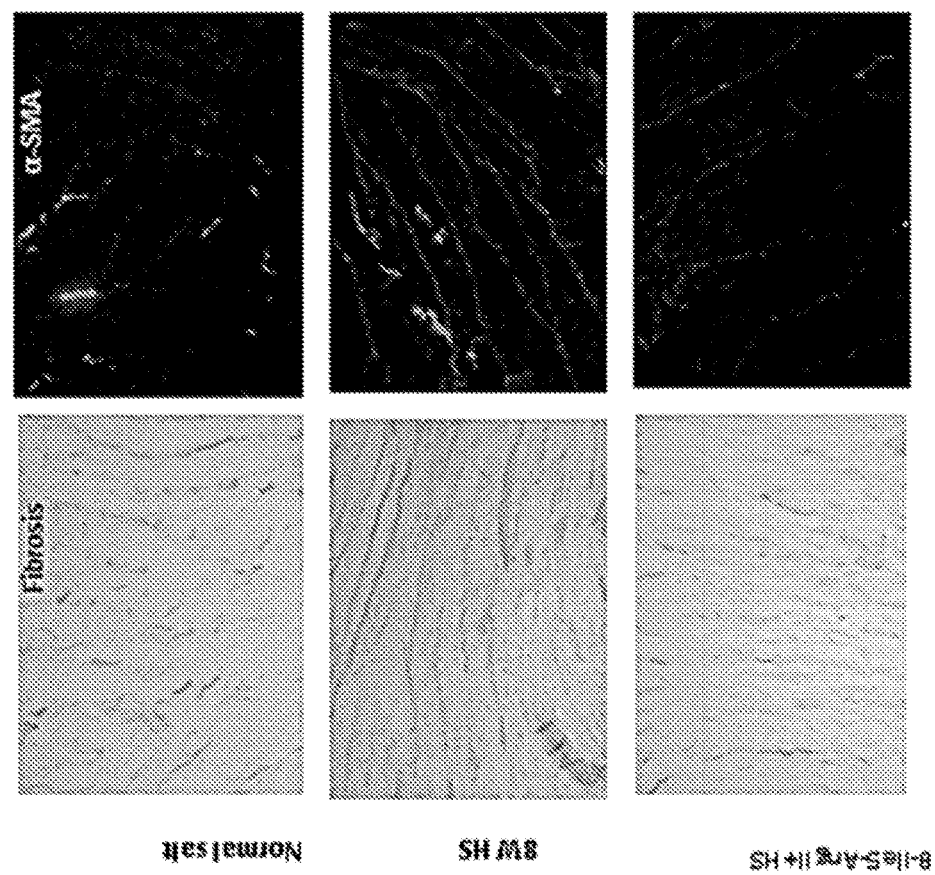
Figure 6:
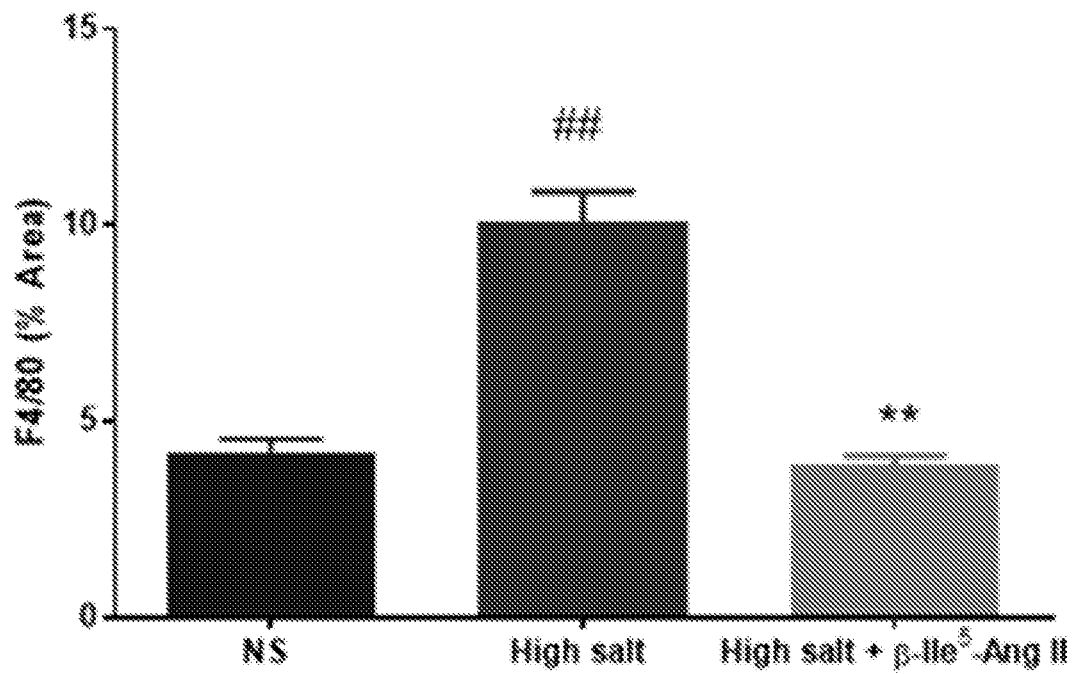
FIG. 6: AT$_2$R stimulation by β-Ile$^5$-Ang II attenuates high salt (5%)-mediated cardiac inflammation. Quantification of positive stained immunofluorescence in transverse heart sections by measuring the pro-inflammatory marker NFκB (measured via phospho-IκBα expression using immunofluorescence staining), and macrophage infiltration/expression (using F4/80 immunofluorescence). High salt-induced inflammatory cell infiltration and activation was reversed by β-Ile$^5$-Ang 11 (75 pmol/kg/min subcutaneously via osmotic mini-pump). Data expressed as mean±s.e.m of percentage positive stained areas (n=5-8). ##P<0.01 versus normal salt; **P<0.01 versus high salt (one way ANOVA with Tukey's correction for multiple comparisons).
Figure 6:
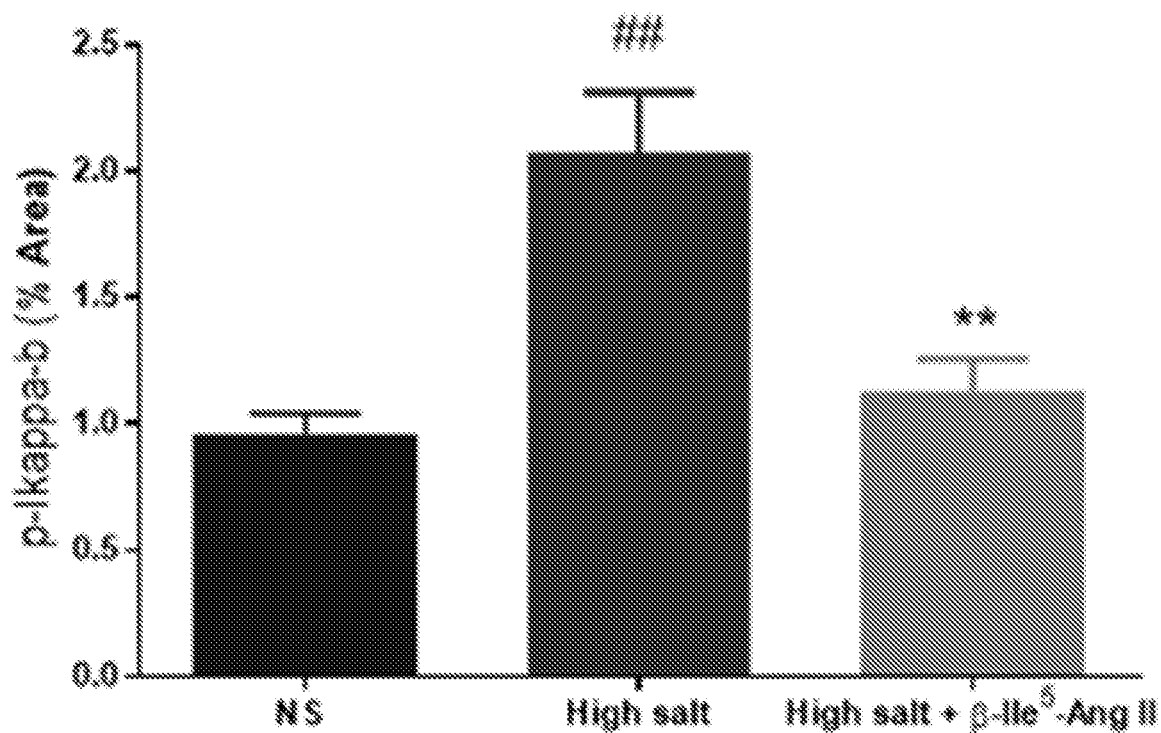

Here, the inventors show that β-Ile$^5$-Ang II reversed high salt-induced cardiac fibrosis in 5 μm thick transverse heart sections, assessed by collagen content using picrosirius red staining and quantified using both bright field and circularized polarized light microscopy. The fibrogenic cytokine TGF-β1 is well known to promote the differentiation of fibroblast to a more synthetic type of myofibroblast. In this context, these β-Ile$^5$-Ang II-treated mice exhibited significantly lower TGF-β1 protein in the heart (by Western blot) which was associated with reduced myofibroblast differentiation evidenced by reduced α-SMA immunohistochemistry (see FIG. 5). These cardiac anti-fibrotic effects of β-Ile$^5$-Ang II were also accompanied by reduced macrophage infiltration/expression (F4/80) and reduced expression of P-IκBα (marker for NFκB activation), which is suggestive of an anti-inflammatory action (FIG. 6).

Figure 7:
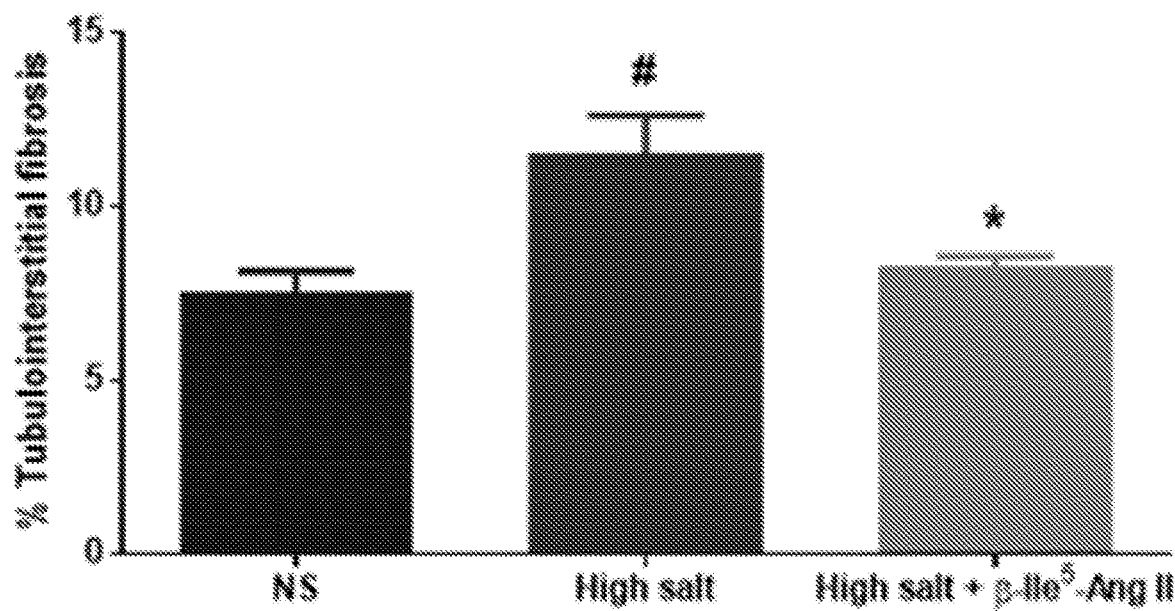
FIG. 7: AT2R stimulation by β-Ile$^5$-Ang II attenuates high salt (5%)-mediated fibrosis and macrophage infiltration/expression in mouse kidney. Male FVB/N mice were untreated; fed a high salt diet for 8 weeks or received β-Ile$^5$-Ang II (75 pmol/kg/min) during weeks 5-8 while on a high salt diet. Kidney tubulointerstitial fibrosis was determined by Mason's Trichrome staining; and macrophage infiltration/expression was determined using F4/80 immunofluorescence; all of which shows that β-Ile$^5$-Ang II (75 pmol/kg/min subcutaneously via osmotic mini-pump) inhibits pro-fibrotic and inflammatory effects of high salt in the kidney. Data expressed as mean±s.e.m of percentage positive stained areas (n=5-8). #P<0.05, ##P<0.01 versus normal salt; *P<0.05, **P<0.01 versus high salt (one way ANOVA with Tukey's correction for multiple comparisons).
Figure 7:
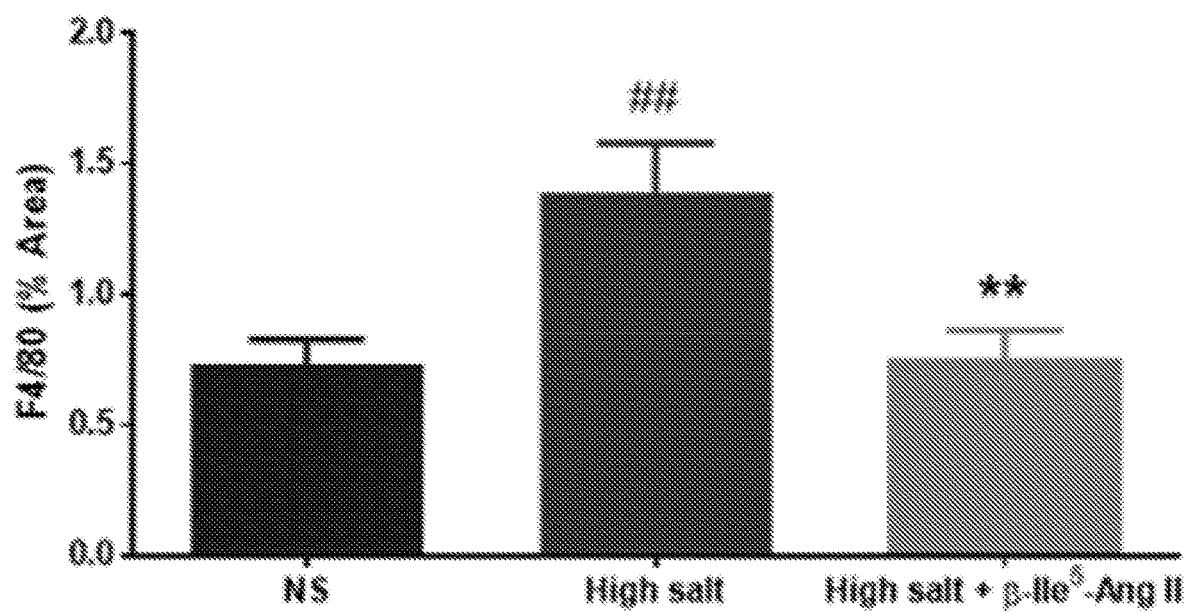

Similar analyses were conducted on kidneys in the same treated animals. β-Ile$^5$-Ang II reversed high salt-induced tubulointerstitial fibrosis and macrophage infiltration, indicating a similar anti-fibrotic and anti-inflammatory effect occurred in kidneys (FIG. 7).

Example 5

Figure 8:
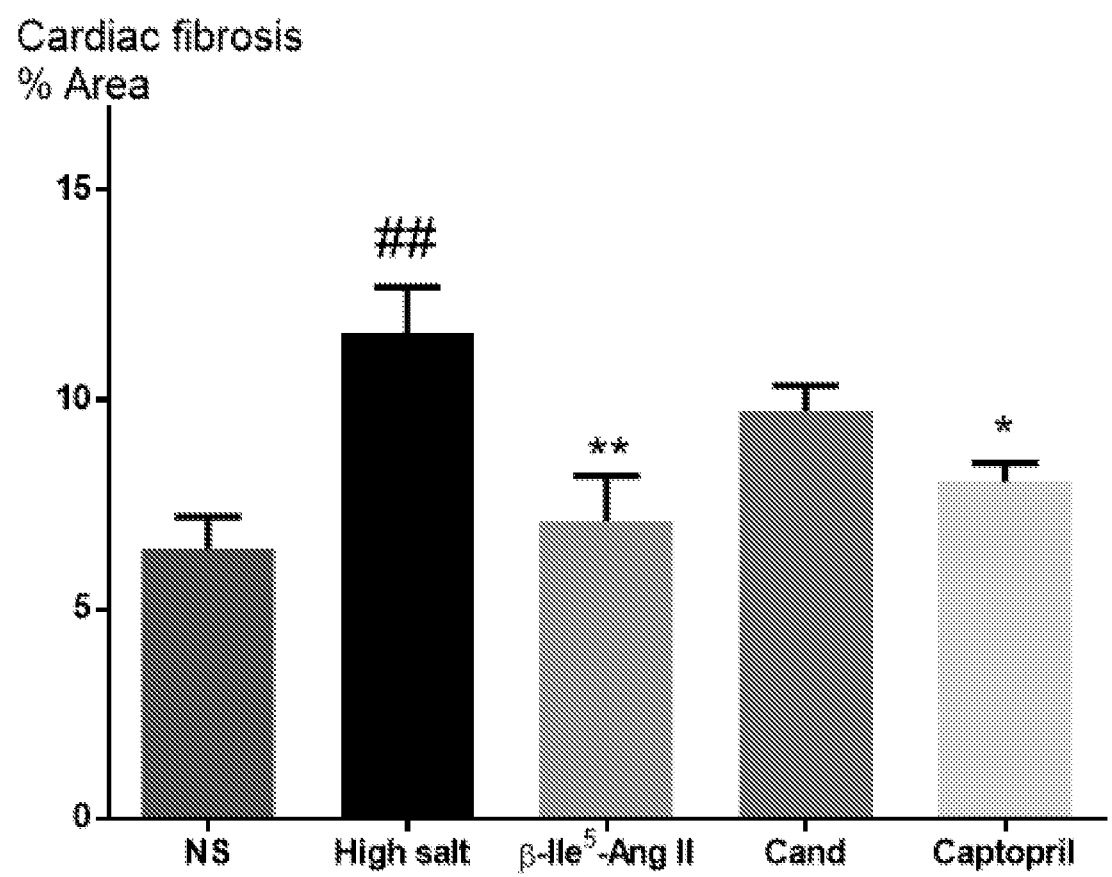
FIG. 8: Comparison of cardiac anti-fibrotic effect of β-Ile$^5$-Ang II (MU23) with the AT1R antagonist candesartan cilexetil (Cand) and the ACE inhibitor captopril in high salt-induced fibrosis in mouse heart. Male FVB/N mice were either untreated (fed normal salt; NS); fed a high salt (5%) diet for 8 weeks or received either β-Ile$^5$-Ang II (75 pmol/kg/min subcutaneously via osmotic mini-pump); Cand (2 mg/kg/day by drinking water) or captopril (3 mg/kg/day by drinking water) during weeks 5-8 while on a high salt diet. Data for cardiac fibrosis determined by picrosirius red staining (under bright field microscopy), showing that β-Ile$^5$-Ang II and captopril similarly inhibited the pro-fibrotic effects of high salt in the heart. Data expressed as mean±s.e.m of percentage positive stained area for fibrosis (n=5-8). ##P<0.01 versus normal salt (NS); *P<0.05; **P<0.01 versus high salt (one way ANOVA with Tukey's correction for multiple comparisons).

Cardioprotective and Hepatoprotective Effects of β-Ile$^5$-Ang II is Similar or Even Greater than Other RAS Inhibitors in a High Salt-Fed Mouse Model Given the striking anti-fibrotic effects of β-Ile$^5$-Ang II, the inventors were interested in comparing its effects in the same model with clinically used inhibitors of the Ang II-AT1R axis that is well known to promote fibrosis/inflammation. Therefore, the inventors compared β-Ile$^5$-Ang II with a large dose of either the ACE inhibitor captopril or the AT1R antagonist candesartan cilexetil (Cand). In analogous studies, β-Ile$^5$-Ang II reversed cardiac fibrosis. Captopril also reversed fibrosis while Cand did not significantly reduce fibrosis from high-salt levels (FIG. 8).

Figure 9:
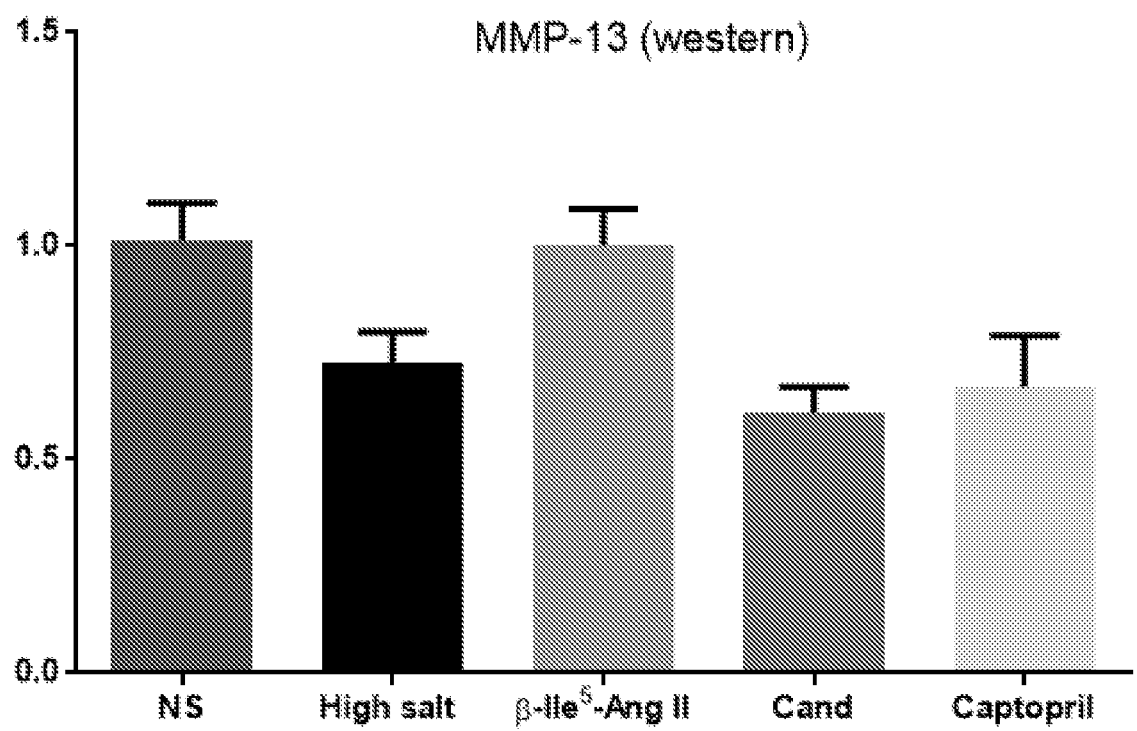
FIG. 9: Comparison of β-Ile$^5$-Ang II (MU23) with the AT1R antagonist candesartan cilexetil (Cand) and the ACE inhibitor captopril on matrix metalloproteinase (MMP)-13 expression in mouse heart. Male FVB/N mice were either untreated (fed normal salt; NS); fed a high salt (5%) diet for 8 weeks or received either β-Ile$^5$-Ang II (75 pmol/kg/min subcutaneously via osmotic mini-pump); Cand (2 mg/kg/day by drinking water) or captopril (3 mg/kg/day by drinking water) during weeks 5-8 while on a high salt diet; with β-Ile$^5$-Ang II tending to reverse the suppression of MMP-13 by high salt (this effect was significant by t-test, P=0.03, but not by 1-way ANOVA of all 5 groups). Western blots and densitometric quantification of protein expression of MMP-13 in cardiac tissue expressed as ratio relative to normal salt ±s.e.m (n=3-4).
Figure 10:
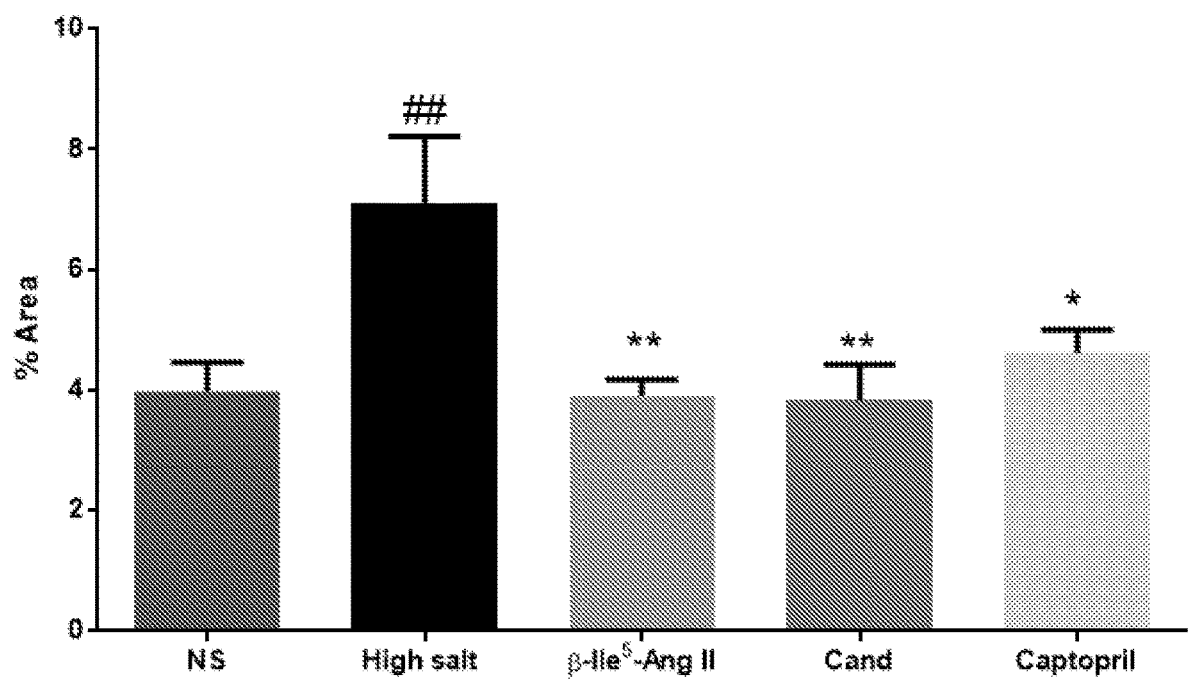
FIG. 10: Comparison of β-Ile$^5$-Ang II (MU23) with the AT1R antagonist candesartan cilexetil (Cand) and the ACE inhibitor captopril on macrophage infiltration in mouse heart. Male FVB/N mice were either untreated (fed normal salt; NS); fed a high salt (5%) diet for 8 weeks or received either β-Ile$^5$-Ang II (75 pmol/kg/min subcutaneously via osmotic mini-pump); Cand (2 mg/kg/day by drinking water) or captopril (3 mg/kg/day by drinking water) during weeks 5-8 while on a high salt diet. Quantification of positive stained immunofluorescence in transverse heart sections of macrophage infiltration/expression (using F4/80 immunofluorescence). High salt-induced inflammatory cell infiltration was reversed by all agents (n=4-8). ##P<0.01 versus normal salt (NS); *P<0.05; **P<0.01 versus high salt (one way ANOVA with Tukey's correction for multiple comparisons).
Figure 11:
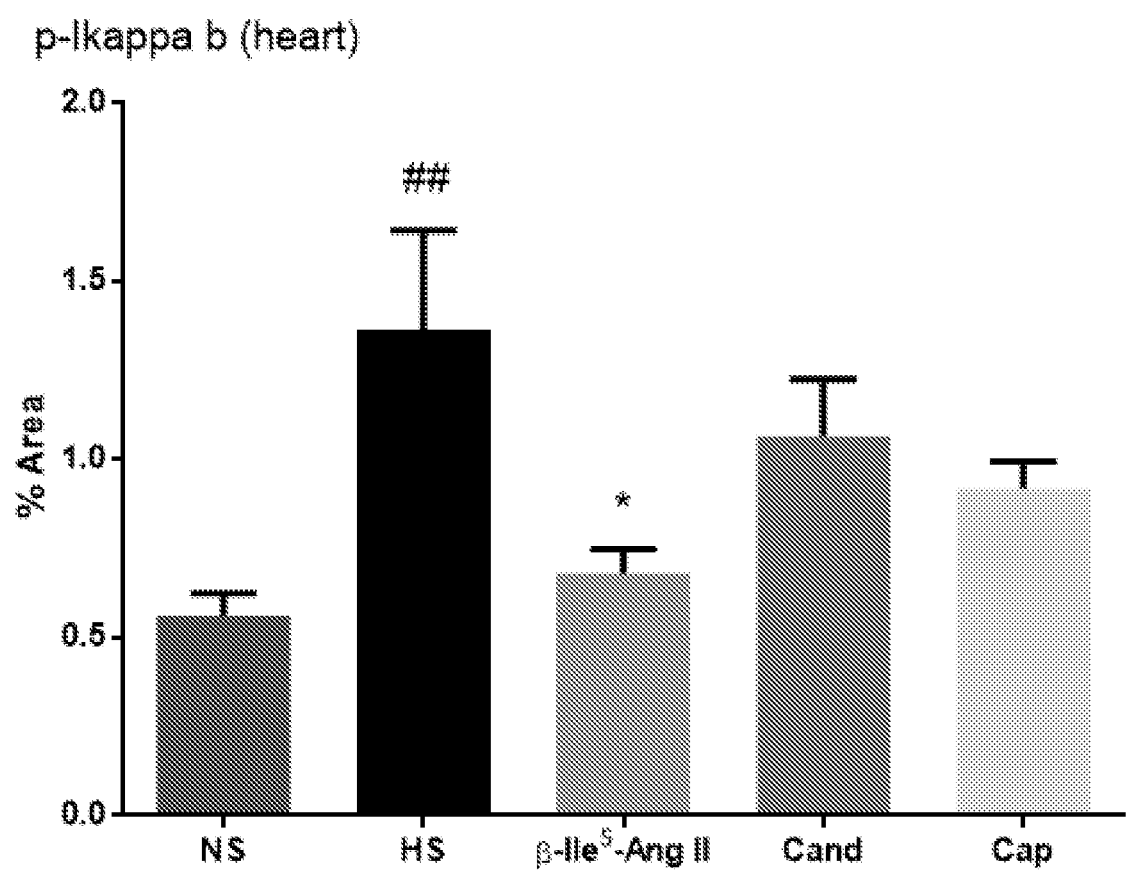
FIG. 11: Comparison of β-Ile$^5$-Ang II (MU23) with the AT1R antagonist candesartan cilexetil (Cand) and the ACE inhibitor captopril on cardiac inflammation in mouse heart. Male FVB/N mice were either untreated (fed normal salt; NS); fed a high salt (5%) diet for 8 weeks or received either β-Ile$^5$-Ang II (75 pmol/kg/min subcutaneously via osmotic mini-pump); Cand (2 mg/kg/day by drinking water) or captopril (3 mg/kg/day by drinking water) during weeks 5-8 while on a high salt diet. Quantification of positive stained immunofluorescence in transverse heart sections of NFκB activation (measured via phospho-IκBα expression using immunofluorescence staining). High salt-induced cardiac inflammation was reversed only by β-Ile$^5$-Ang II (n=5-7). ##P<0.01 versus normal salt (NS); ##P<0.01 versus normal salt (NS); *P<0.05 versus high salt (one way ANOVA with Tukey's correction for multiple comparisons).

Homeostasis of ECM is maintained by the balance between collagen synthesis and collagen degradation. MMP-13 is one of the main collagenase present in the heart and this was measured by Western blot (FIG. 9). Generally MMP-13 levels were decreased in the high salt-compared with normal salt-groups suggesting less collagen degradation contributed to the ECM phenotype of increased cardiac fibrosis in hearts obtained from high salt-fed mice. Neither captopril nor Cand altered MMP-13 levels from those of high salt group. By contrast, β-Ile$^5$-Ang II normalised MMP-13 to levels observed in the normal salt group and MMP-13 levels were significantly elevated compared with high salt group by t-test (P=0.03) although this effect failed to reach significance when analysis of the 5 groups together (by 1-way ANOVA) was performed. In any case, the increased protein expression suggests greater collagen degradation, therefore β-Ile$^5$-Ang II was protective against high salt-induced cardiac fibrosis by down-regulating collagen synthesis (FIGS. 5 & 8) and up-regulating collagen degradation (FIG. 9). Moreover, the ECM profile of β-Ile$^5$-Ang II differed from both ACE inhibition and AT1R blockade. In addition β-Ile$^5$-Ang II did not alter SBP while both RAS inhibitors tended to lower SBP, although the effects are small in this model when basal SBP is not markedly elevated (data not shown). All three treatment reduced macrophage infiltration/expression in the heart (FIG. 10), while only β-Ile$^5$-Ang II significantly reduced expression of P-IκBα (marker for NFκB activation) in the heart (FIG. 11). Indeed, reduced NFκB activation confirms the ability of β-Ile$^5$-Ang II to dampen a key pro-inflammatory regulator that affects transcription of other ECM and inflammatory genes.

Figure 12:
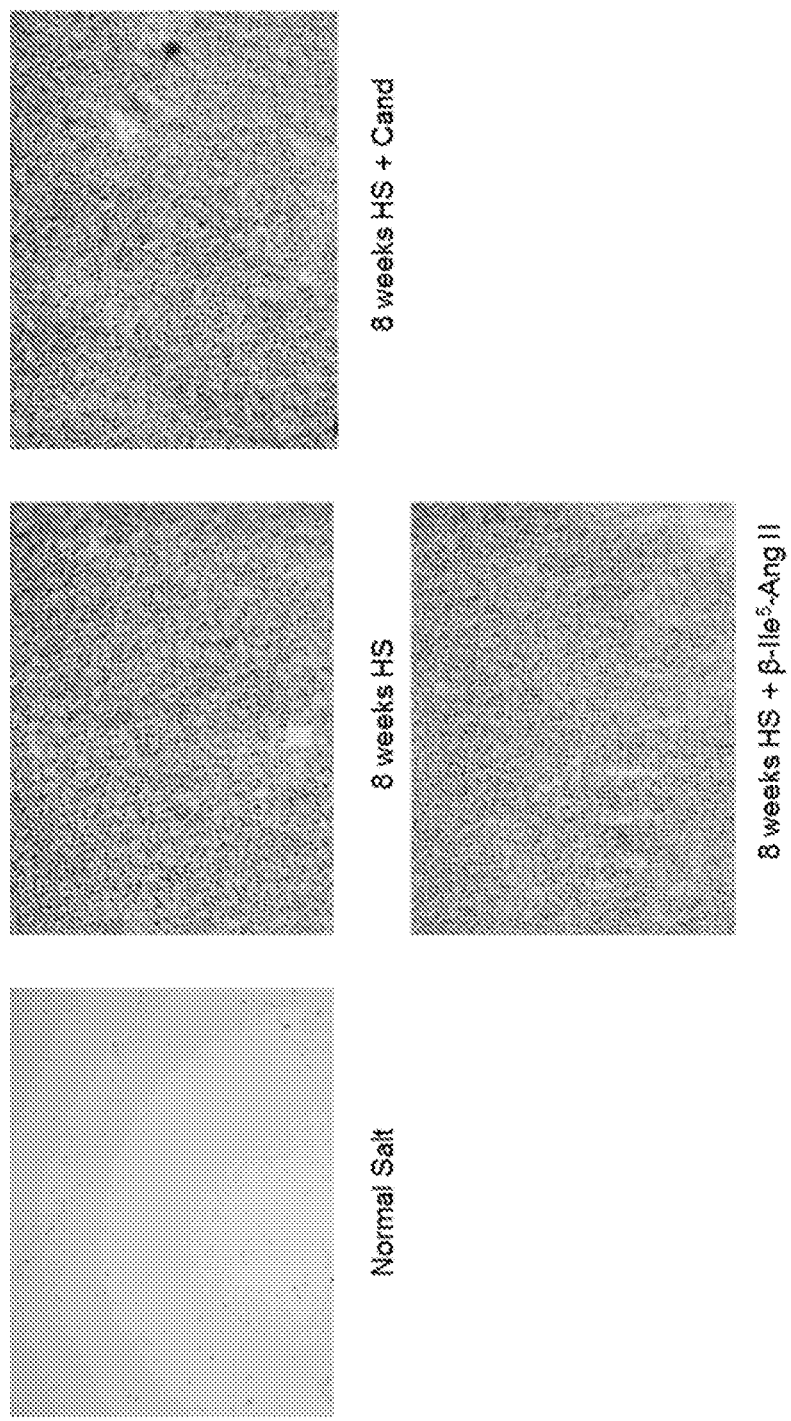
FIG. 12: Representative images of liver sections from male FVB/N mice that were either untreated (fed normal salt; NS); fed a high salt (5%) diet for 8 weeks or received either β-Ile$^5$-Ang II (75 pmol/kg/min subcutaneously via osmotic mini-pump) or Cand (2 mg/kg/day by drinking water) during weeks 5-8 while on a high salt diet. Transverse sections were stained with Oil Red 0 to indicate steatosis (fatty deposits).
Figure 14:
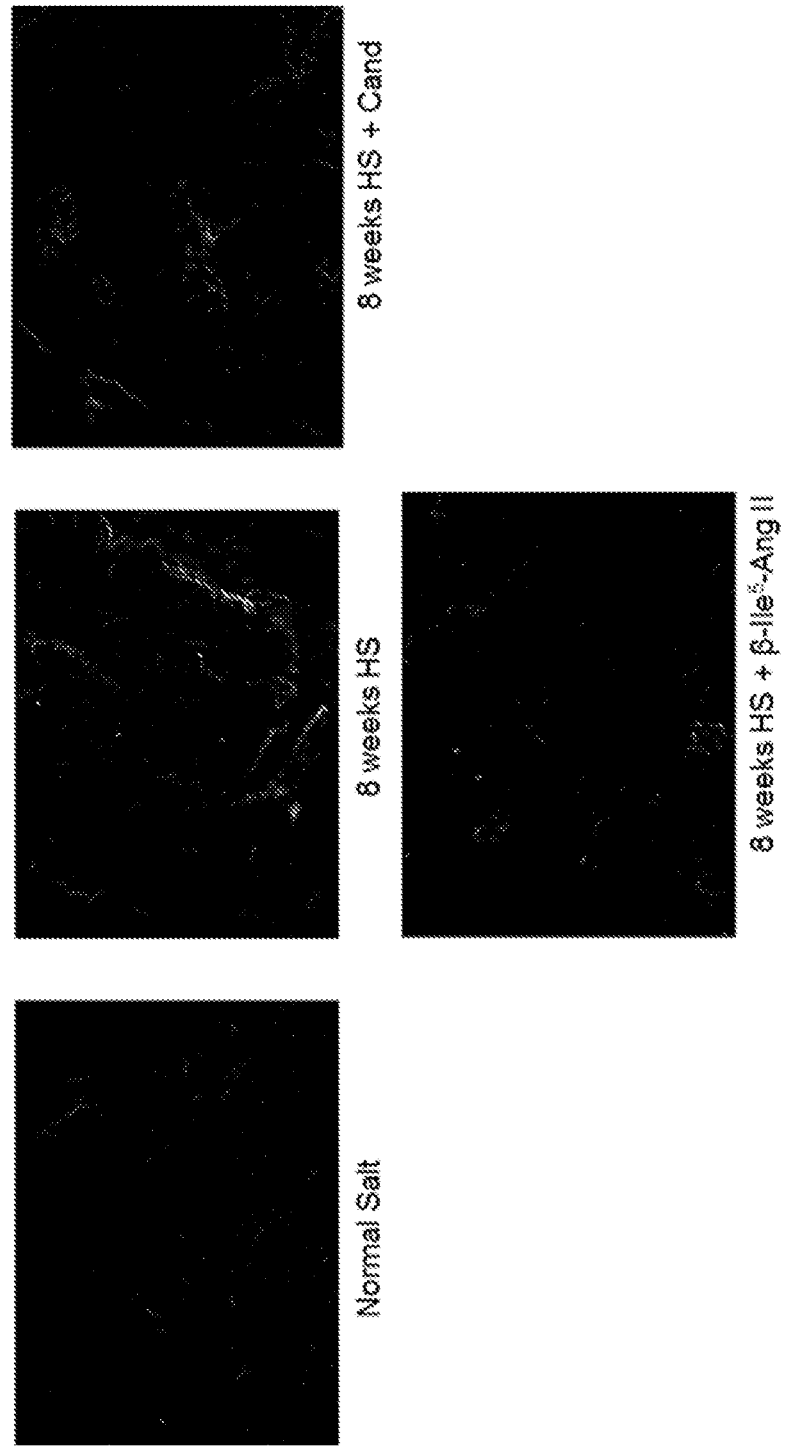
FIG. 14: Representative images of liver sections from male FVB/N mice that were either untreated (fed normal salt; NS); fed a high salt (5%) diet for 8 weeks or received either β-Ile$^5$-Ang II (75 pmol/kg/min subcutaneously via osmotic mini-pump) or Cand (2 mg/kg/day by drinking water) during weeks 5-8 while on a high salt diet. Transverse sections were stained with picrosirius red, under polarized light microscopy, to indicate collagen deposition.

Salt is well known to be an accelerating factor for the progression of metabolic syndrome and is implicated in development of cardiovascular diseases, most likely due to its pro-oxidant properties. Recent evidence indicates that a high salt diet (HSD) can exacerbate fat and fibrosis accumulation in the liver of HFD-fed lectin like oxidized low-density lipoprotein receptor-1 (LOX-1) transgenic (Tg) and apoE knockout (KO) (TgKO) mice, a model used in studies investigating metabolic syndrome (Uetake et al, Lipids in Health and Disease (2015) 14:6). The inventors were therefore interested in whether a high salt diet alone induces changes in liver morphology in FVB/N mice given a high salt diet for 8 weeks. Indeed, high salt caused a profound increase in steatosis in FVB/N mice (fatty deposits identified by Oil Red 0 staining; FIG. 12) suggestive of non-alcoholic fatty liver disease (NAFLD). Additionally, there was also a small increase in fibrosis (collagen determined by picrosirius red staining under polarized light microscopy; FIG. 14) suggestive of early stage non-alcoholic steatohepatitis (NASH).

Figure 13:
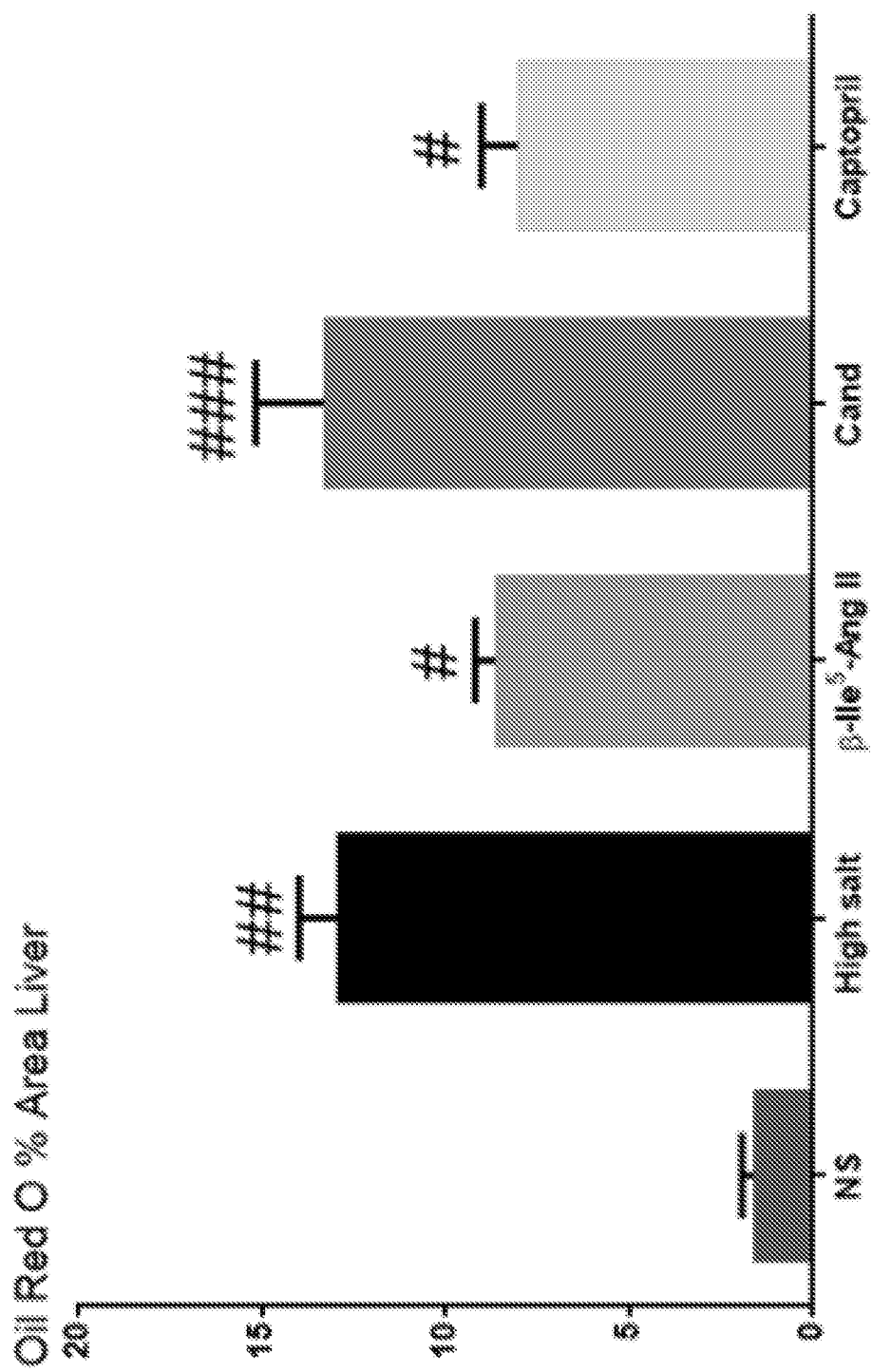
FIG. 13: Comparison of β-Ile$^5$-Ang II (MU23) with the AT1R antagonist candesartan cilexetil (Cand) and the ACE inhibitor captopril on steatosis in mouse liver. Male FVB/N mice were either untreated (fed normal salt; NS); fed a high salt (5%) diet for 8 weeks or received either β-Ile$^5$-Ang II (75 pmol/kg/min subcutaneously via osmotic mini-pump); Cand (2 mg/kg/day by drinking water) or captopril (3 mg/kg/day by drinking water) during weeks 5-8 while on a high salt diet. Data expressed as mean±s.e.m of percentage positive stained area for Oil Red 0 indicating steatosis (n=4-9). High salt-induced liver steatosis was partially reversed by β-Ile$^5$-Ang II and captopril. #P<0.05, ###P<0.001 versus normal salt (one way ANOVA with Tukey's correction for multiple comparisons).
Figure 15:
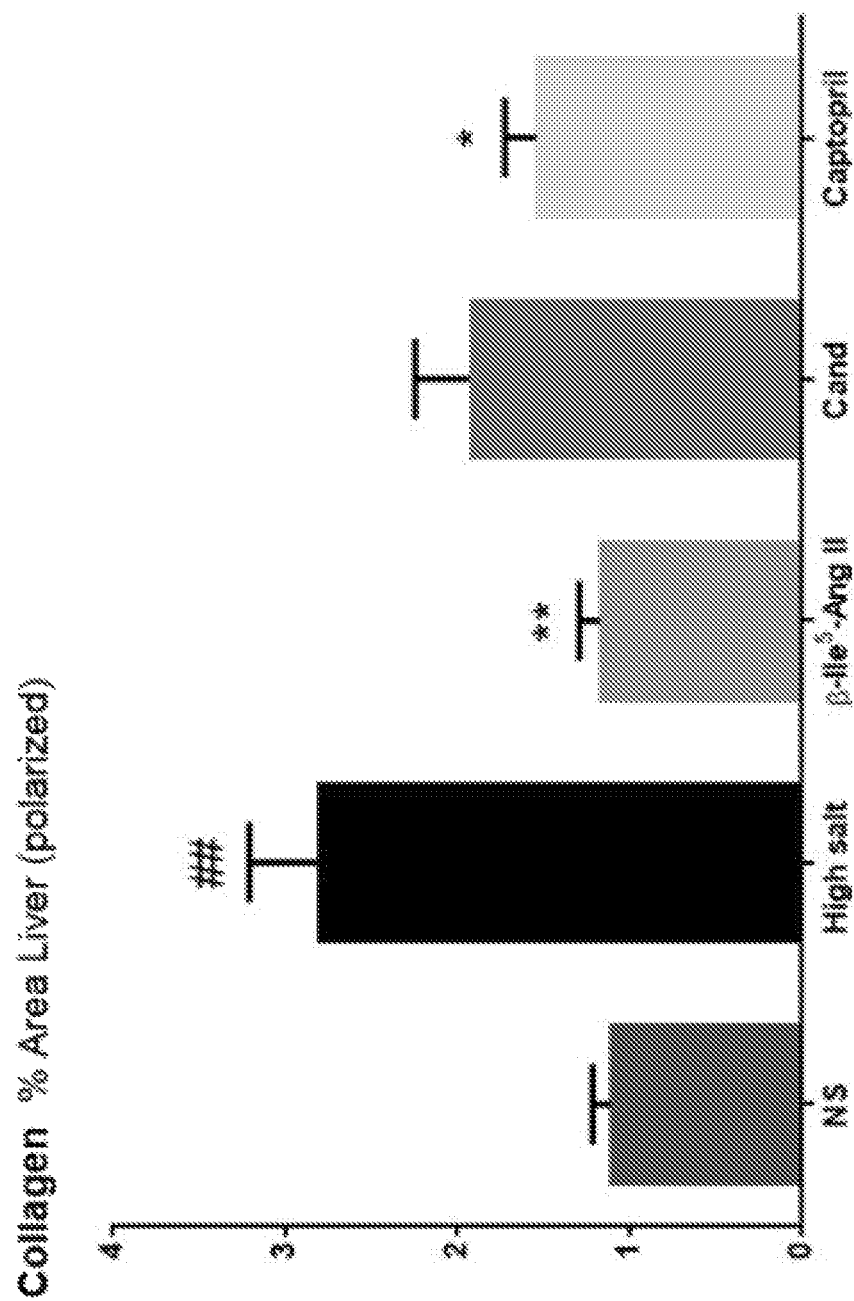
FIG. 15: Comparison of β-Ile$^5$-Ang II (MU23) with the AT1R antagonist candesartan cilexetil (Cand) and the ACE inhibitor captopril on fibrosis in mouse liver. Male FVB/N mice were either untreated (fed normal salt; NS); fed a high salt (5%) diet for 8 weeks or received either β-Ile$^5$-Ang II (75 pmol/kg/min subcutaneously via osmotic mini-pump); Cand (2 mg/kg/day by drinking water) or captopril (3 mg/kg/day by drinking water) during weeks 5-8 while on a high salt diet. Data for liver fibrosis determined by picrosirius red staining (under polarized light microscopy), showing that β-Ile$^5$-Ang II and captopril similarly inhibited the pro-fibrotic effects of high salt in the liver. Data expressed as mean±s.e.m of percentage positive stained area for fibrosis (n=4-9). ##$P<0.01$ versus normal salt (NS); *$P<0.05$, **$P<0.01$ versus high salt (one way ANOVA with Tukey's correction for multiple comparisons).

Under these conditions, β-Ile$^5$-Ang II and captopril, but not Cand, significantly reduced excess lipid accumulation (FIG. 13). Although liver fibrosis was relatively modest, 8-Ile$^5$-Ang II reversed collagen accumulation to levels seen in normal salt group while the two RAS inhibitors were less effective (FIG. 15). These protective effects of β-Ile$^5$-Ang II in the liver show a clear ability for the AT2R agonist β-Ile$^5$-Ang II to exert cardioprotective effects in the same animals.

Example 6

Cardioprotective and Hepatoprotective Effects of β-Pro$^7$-Ang III, and the Novel, Unpublished Derivative D-Arg$^2$-β-Pro$^7$-Ang III, in a High Salt-Fed Mouse Model Here, the inventors show that β-Pro$^7$-Ang III, and novel unpublished derivatives of this peptide, reversed high salt-induced cardiac fibrosis (assessed in an identical manner as in previous Examples 4 and 5).

A number a highly AT2R selective Ang peptides have been synthesised and characterised on the basis of radioligand binding experiments using $^{125}$I-Sar$^1$-Ile$^8$-AngII as a nonselective ligand that is able to bind to HEK-293 cells transfected with either human AT1R or human AT2Rs. The ability of novel compounds of interest to displace the Ang II-radioligand from both AT1R and AT2Rs leads to the generation of IC$_{50}$ values that determine the relative ability of test compounds to interact with both ATR subtypes.

Figure 16:
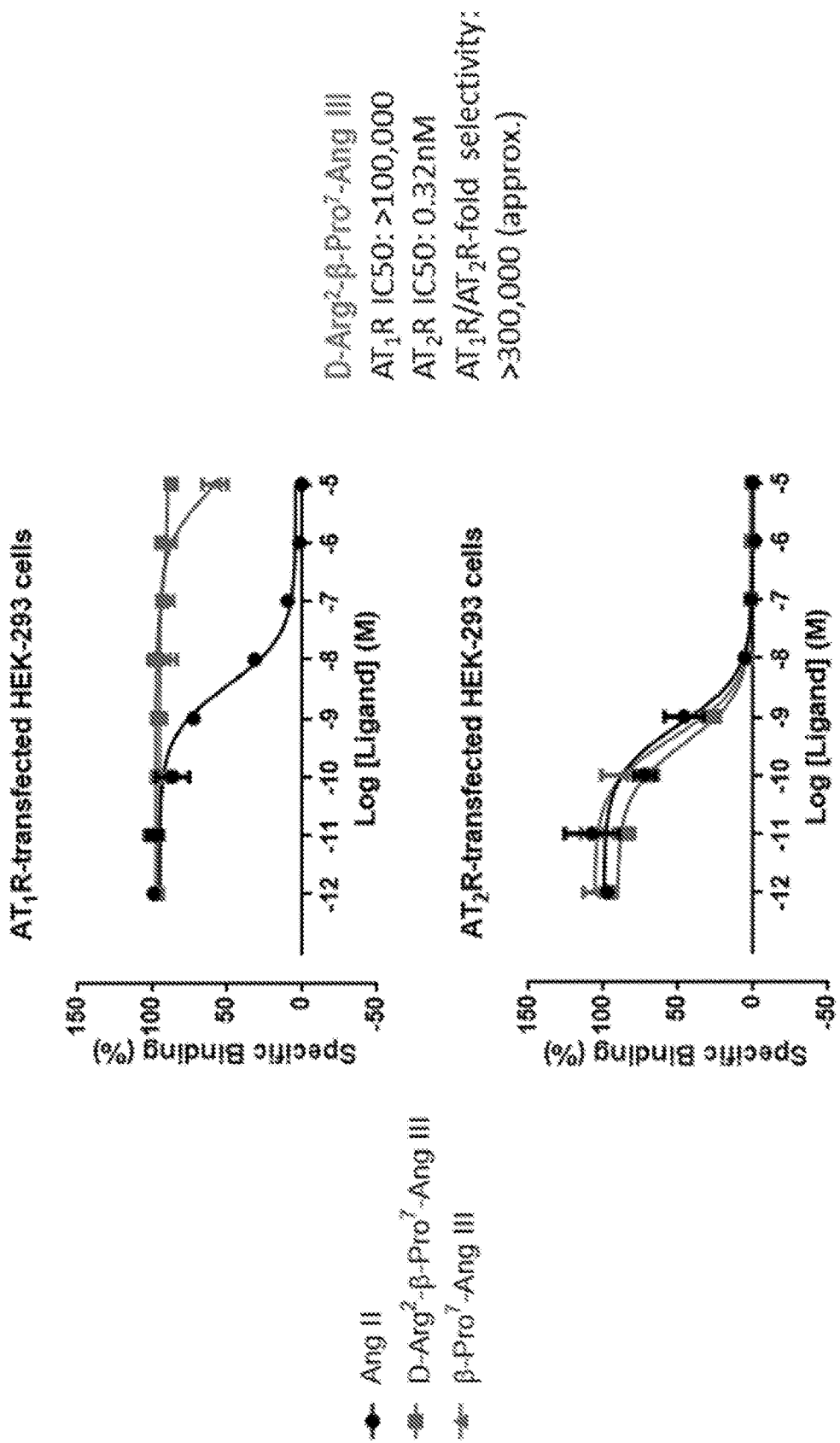
FIG. 16: Competition radioligand binding assays to determine the ability of β-Pro$^7$-Ang III, D-Arg$^2$-β-Pro$^7$-Ang III and Ang II to displace the nonselective iodinated ligand $^{125}$I-Sar$^1$-Ile$^8$-AngII from either AT1R (top panel) or AT2R (bottom panel) in transfected HEK-293 cells. Typically, the ability of compounds of interest to displace the Ang II radioligand from both AT1R and AT2R will lead to the generation of IC50 values that determine the relative ability of test compounds to interact with both receptors. In this instance, Ang II readily binds to both AT1R and AT2R, whereas both β-Pro$^7$-Ang III and D-Arg$^2$-β-Pro$^7$-Ang III bind poorly at AT1R, but with high affinity at AT2R. This results in a relative selectivity of D-Arg$^2$-β-Pro$^7$-Ang III for AT2Rs over AT1R that is conservatively estimated at >300,000-fold (see Table 3).
Figure 17:
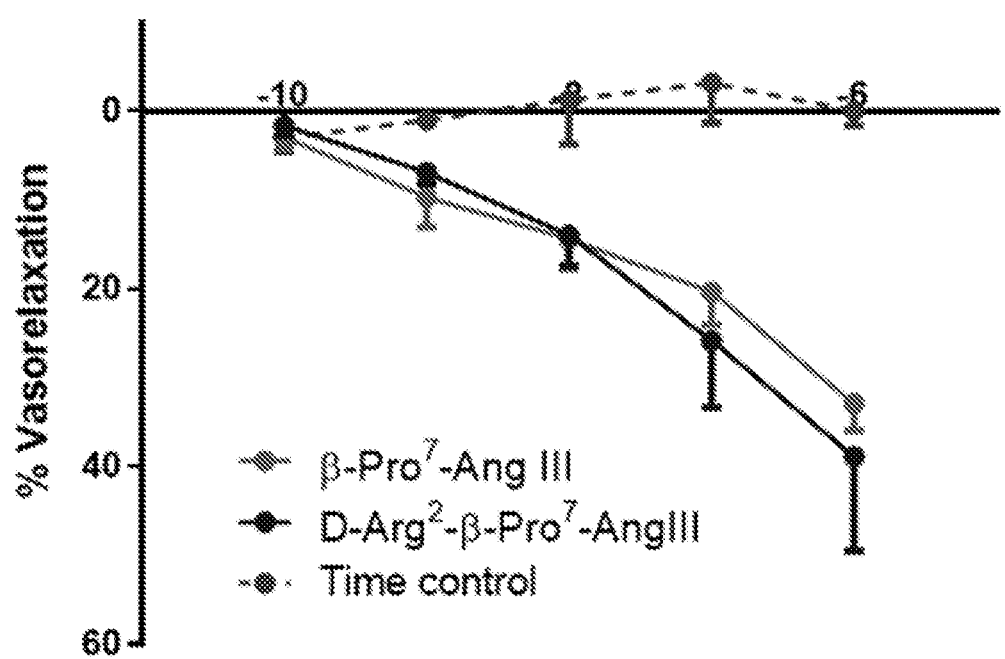
FIG. 17: The selective AT2R ligands, β-Pro$^7$-Ang III and D-Arg$^2$-β-Pro$^7$-Ang III, are functional agonists in vasculature. Both peptides (0.1-1000 nM) evoked concentration-dependent vasorelaxation of pre-contracted mouse aortae, while time-control tissues were exposed to the contractile agent U46619 and failed to relax over the same period when there was no further drug additions (n=5-6).
Figure 18:
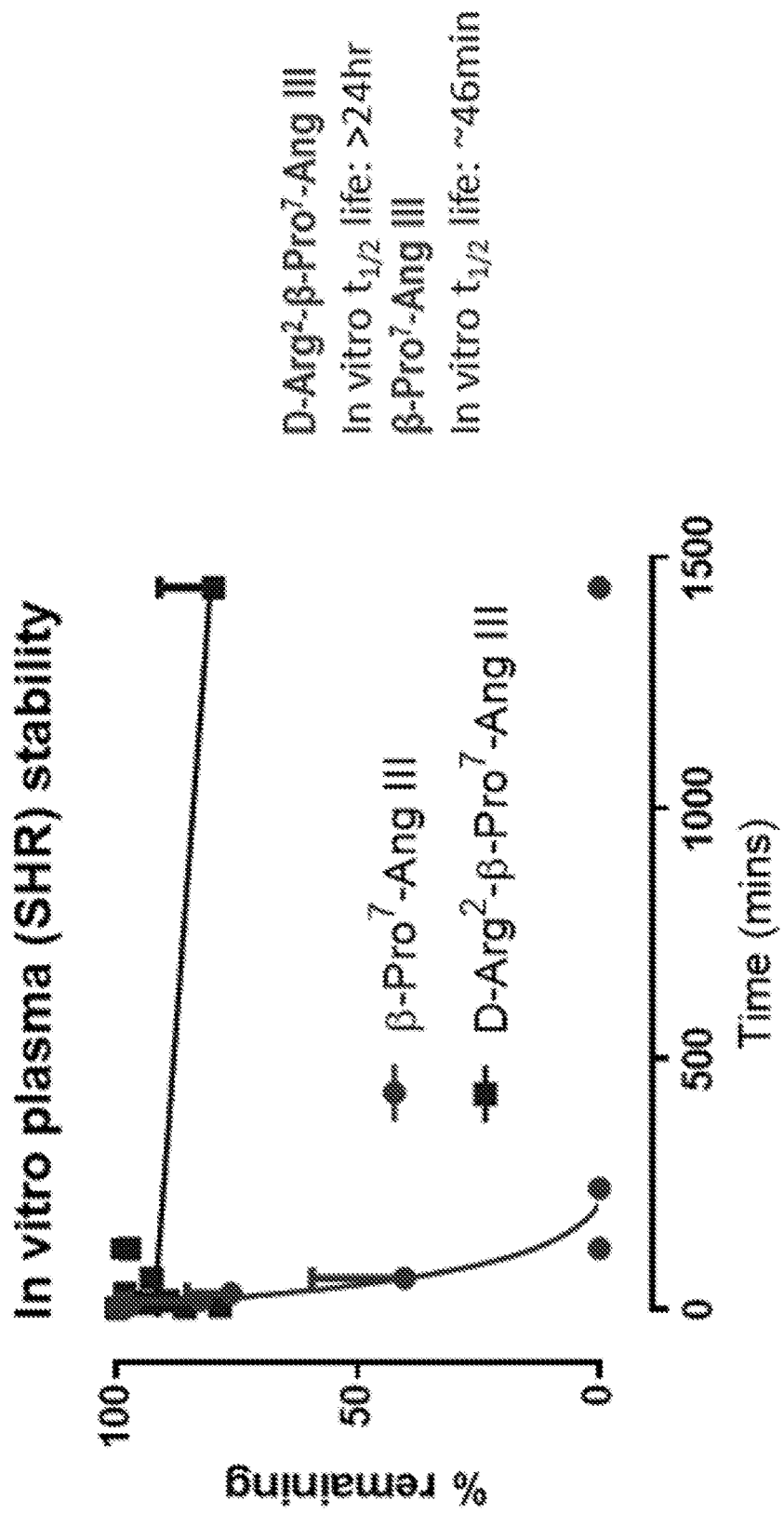
FIG. 18: In vitro plasma stability of β-Pro$^7$-Ang III and D-Arg$^2$-β-Pro$^7$-Ang III. The peptides were incubated for various times in plasma obtained from male spontaneously hypertensive rats (SHR). Approximately 80% of D-Arg$^2$-β-Pro$^7$-Ang III remained in plasma after 24 hour incubation, while β-Pro$^7$-Ang III was degraded within 2 hours (see Table 3 for $t_{1/2}$ values).

The binding profiles for D-Arg$^2$-β-Pro$^7$-Ang III and β-Pro$^7$-Ang III were performed in the same experiments and are provided in FIG. 16. For the first time, the inventors have showed that D-Arg$^2$-β-Pro$^7$-Ang III exhibited marked AT2R:AT1R selectivity since this ratio was >300,000 and was most likely under-estimated since this ligand did not substantially displace the Ang II-radioligand even at 10 μM (FIG. 16). Like β-Pro$^7$-Ang III (Del Borgo et al 2015 Clin. Sci.), the novel ligand D-Arg$^2$-β-Pro$^7$-Ang III was a functional agonist as it caused relaxation of pre-contracted murine aortic rings (FIG. 17). Unlike β-Pro$^7$-Ang III, the novel peptide D-Arg$^2$-β-Pro$^7$-Ang III was extremely stable in rat plasma since >80% of the compound was remaining after 24 hours (FIG. 18).

Figure 19:
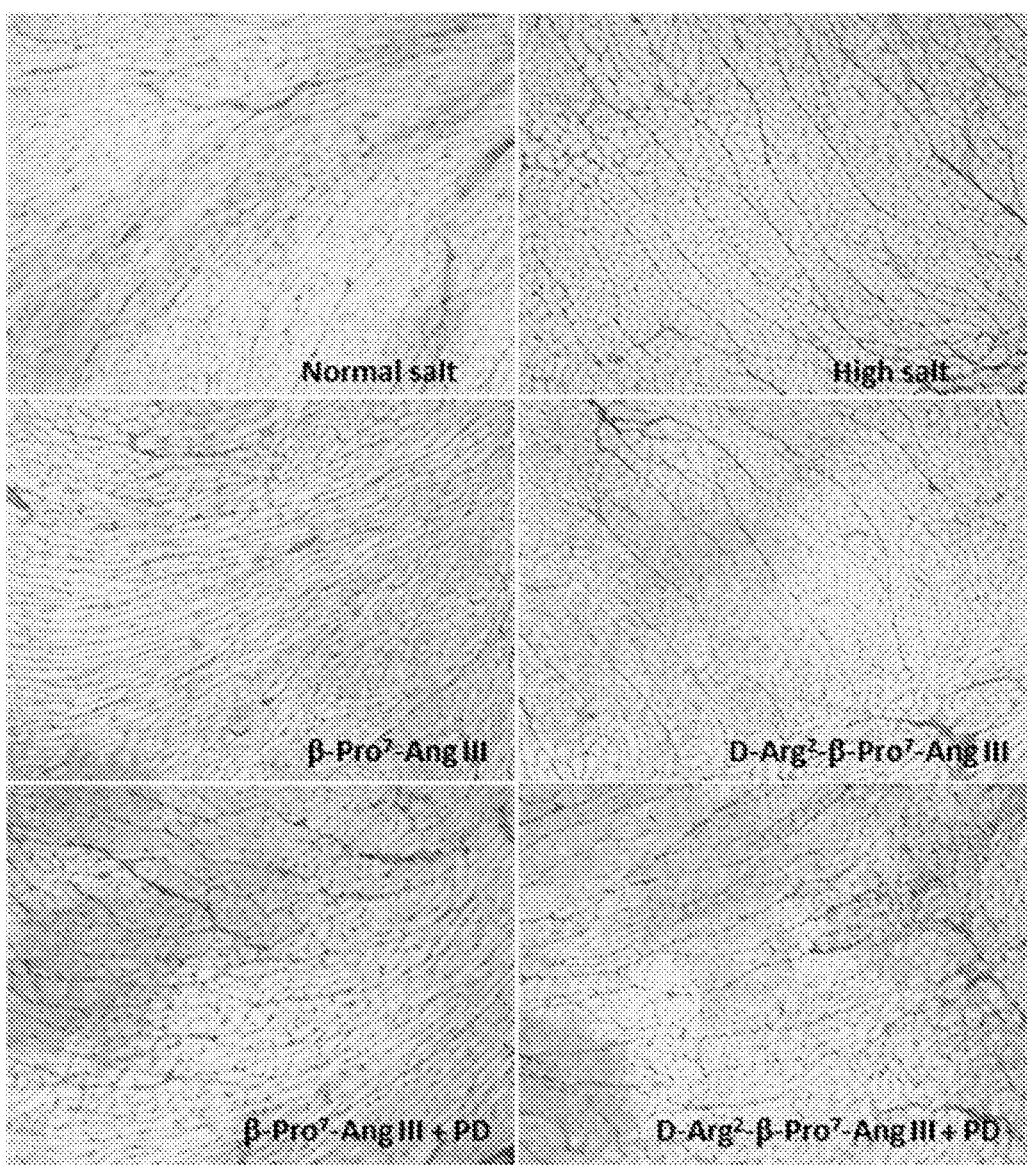
FIG. 19: β-Pro$^7$-Ang III and D-Arg$^2$-β-Pro$^7$-Ang III attenuates high salt (5%)-mediated fibrosis in mouse heart. Representative images are shown of transverse heart sections stained for collagen using picrosirius red (PSR) under bright field microscopy, taken from male FVB/N mice that were untreated (normal salt); fed a high salt diet for 8 weeks or received either β-Pro$^7$-Ang III or D-Arg$^2$-β-Pro$^7$-Ang III (75 pmol/kg/min subcutaneously via osmotic mini-pump) during weeks 5-8 while on a high salt diet.
Figure 20:
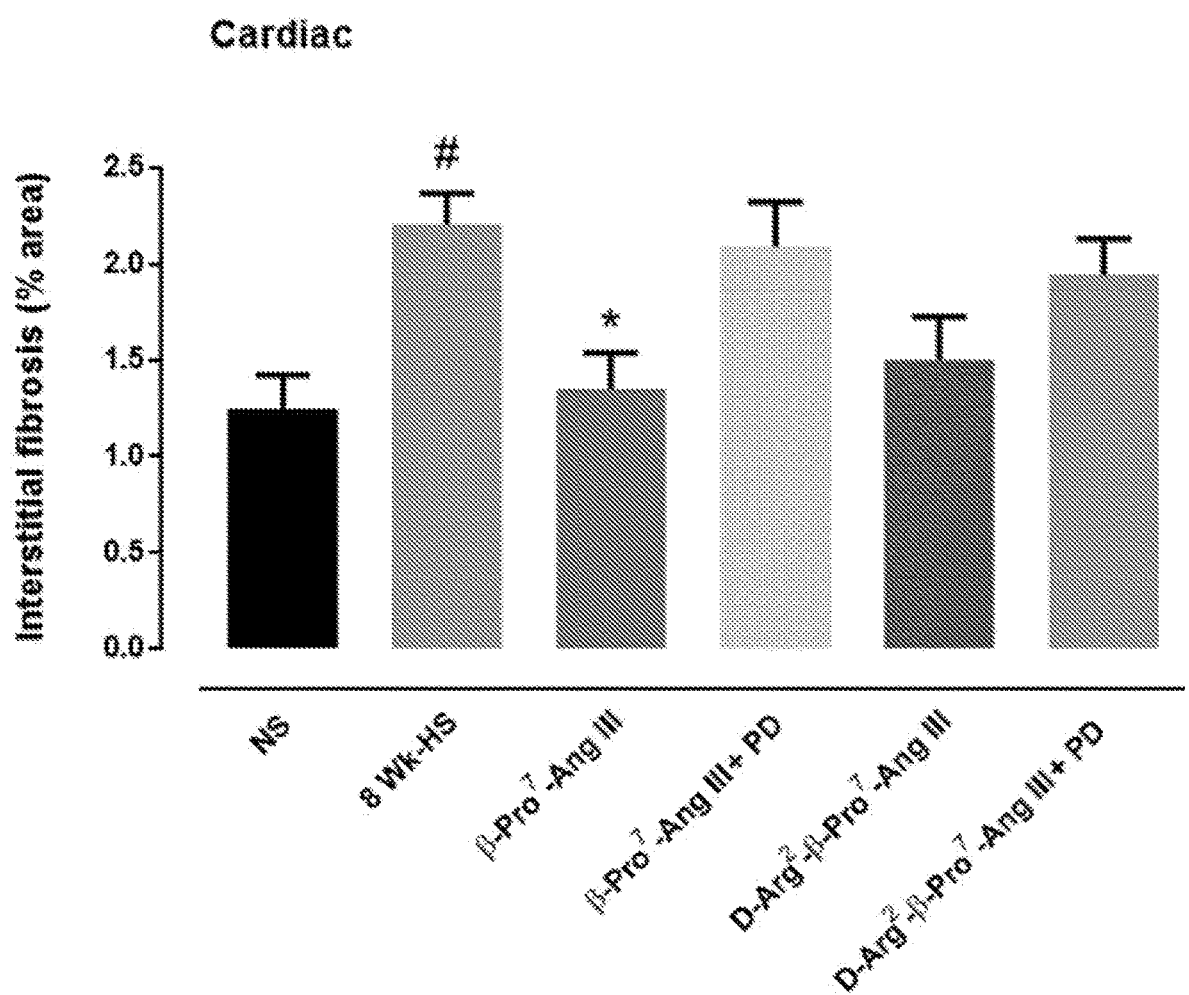
FIG. 20: AT2R stimulation by β-Pro$^7$-Ang III and D-Arg$^2$-β-Pro$^7$-Ang III attenuates high salt (5%)-mediated fibrosis in mouse heart, and these effects are absent when AT2R are concomitantly blocked. Mean data for cardiac fibrosis determined by picrosirius red, under polarised light microscopy, taken from male FVB/N mice that were untreated (normal salt); fed a high salt diet for 8 weeks (8HS) or received either β-Pro$^7$-Ang III or D-Arg$^2$-β-Pro$^7$-Ang III (both at 75 pmol/kg/min subcutaneously via osmotic mini-pump) alone during weeks 5-8 while on a high salt diet, or were co-treated with the AT2R antagonist PD123319 (PD; 1 mg/kg/day subcutaneously via osmotic mini-pump) (n=6-8). β-Pro$^7$-Ang III and D-Arg$^2$-β-Pro$^7$-Ang III both reversed the pro-fibrotic effects of high salt in the heart, while PD123319 attenuated the anti-fibrotic effects of these peptides. Data expressed as mean±s.e.m of percentage positive stained area for fibrosis. #$P<0.05$ versus normal salt (NS); *$P<0.05$ versus high salt (one way ANOVA with Tukey's correction for multiple comparisons).
Figure 21:
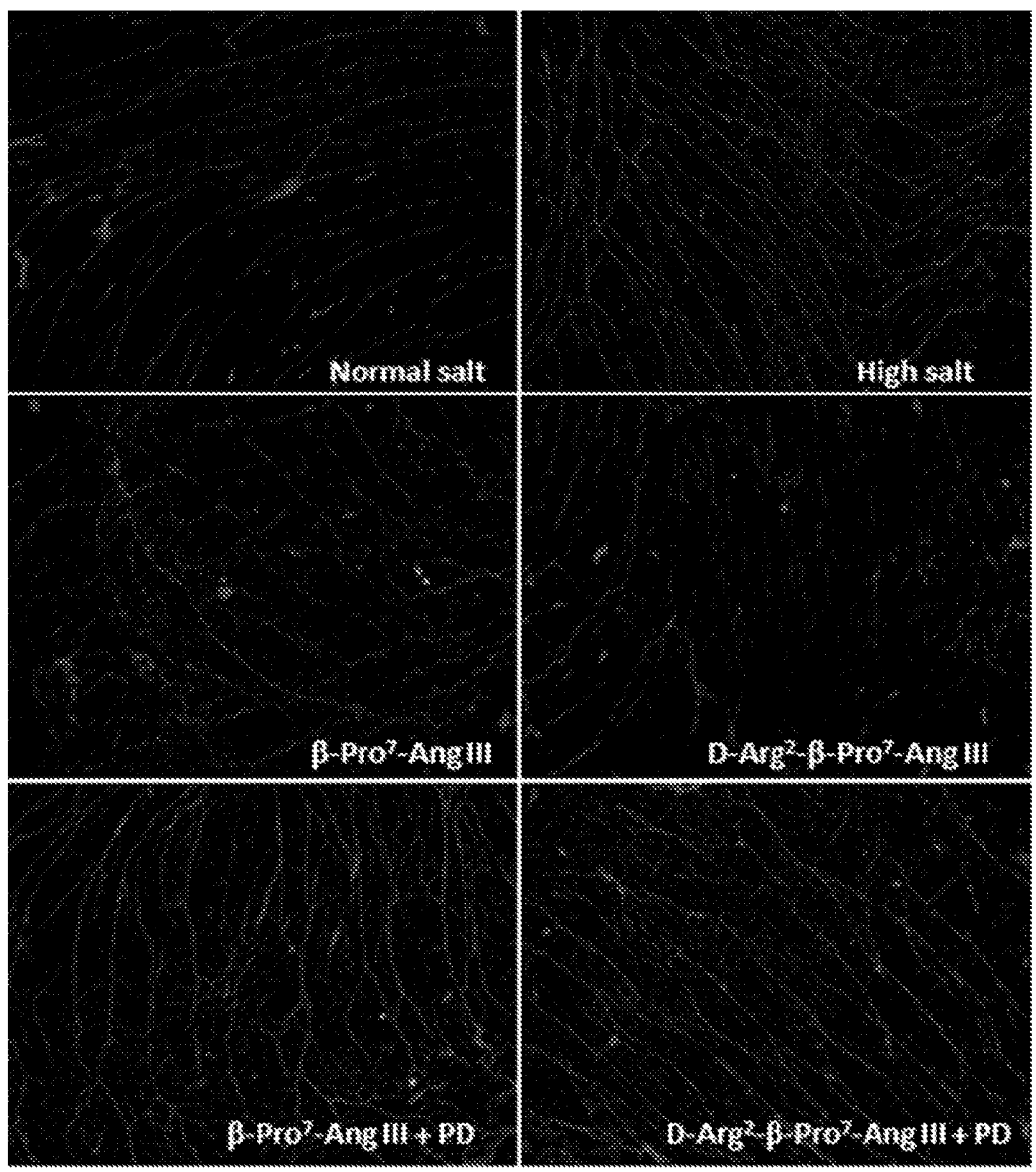
FIG. 21: β-Pro$^7$-Ang III and D-Arg$^2$-β-Pro$^7$-Ang III attenuates high salt (5%)-mediated myofibroblast differentiation in mouse heart. Representative images are shown of transverse heart sections with positive stained immunofluorescence of myofibroblast differentiation determined by α-SMA (marker for myofibroblast expression), taken from male FVB/N mice that were untreated (normal salt); fed a high salt diet for 8 weeks or received either β-Pro$^7$-Ang III or D-Arg$^2$-β-Pro$^7$-Ang III (75 pmol/kg/min subcutaneously via osmotic mini-pump) during weeks 5-8 while on a high salt diet.
Figure 22:
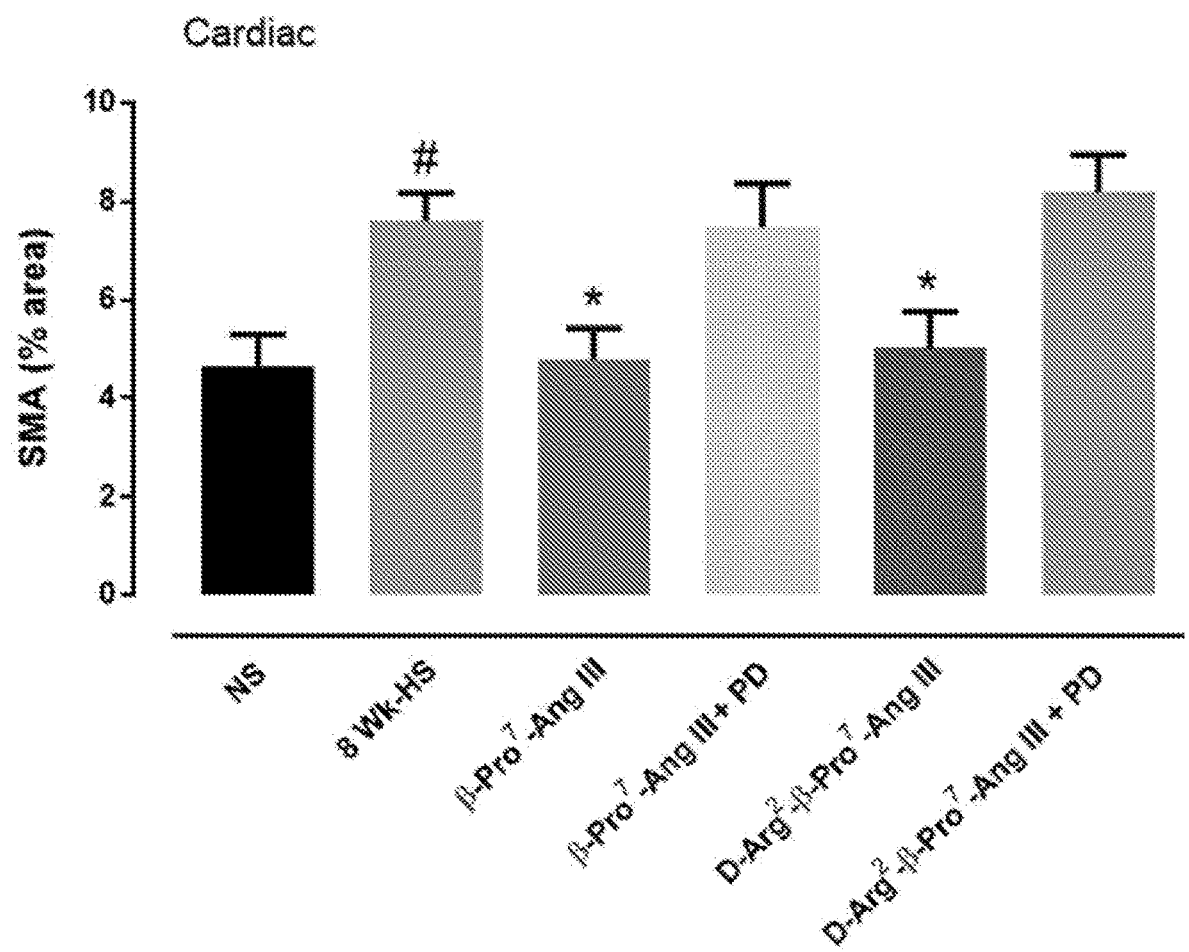
FIG. 22: AT2R stimulation by β-Pro$^7$-Ang III and D-Arg$^2$-β-Pro$^7$-Ang III attenuates high salt (5%)-mediated myofibroblast differentiation in mouse heart, and these effects are absent when AT2R are concomitantly blocked. Mean data for myofibroblast differentiation determined by α-SMA, taken from male FVB/N mice that were untreated (normal salt); fed a high salt diet for 8 weeks (8HS) or received either β-Pro$^7$-Ang III or D-Arg$^2$-β-Pro$^7$-Ang III (both at 75 pmol/kg/min subcutaneously via osmotic mini-pump) alone during weeks 5-8 while on a high salt diet, or were co-treated with the AT2R antagonist PD123319 (PD; 1 mg/kg/day subcutaneously via osmotic mini-pump) (n=6-8). β-Pro$^7$-Ang III and D-Arg$^2$-β-Pro$^7$-Ang III both reversed myofibroblast differentiation induced by high salt in the heart, while PD123319 attenuated the inhibitory effects of these peptides. Data expressed as mean±s.e.m of percentage positive stained area for α-SMA. #$P<0.05$ versus normal salt (NS); *$P<0.05$ versus high salt (one way ANOVA with Tukey's correction for multiple comparisons).

Using analogous experimental protocols and techniques to those already described in Examples 3 and 4, both β-Pro$^7$-Ang III and D-Arg$^2$-β-Pro$^7$-Ang III, given during weeks 5-8 of high salt diet, reversed established cardiac fibrosis, and these anti-fibrotic effects were attenuated when the AT2R antagonist PD123319 (1 mg/kg/day subcutaneous infusion) was co-administered (FIGS. 19 and 20). In addition, high salt evoked an increase in myofibroblast differentiation as evidenced by increased α-SMA staining in the heart (FIG. 21) which clearly contributes to collagen production. Consistent with the fibrosis data, both β-Pro$^7$-Ang III and D-Arg$^2$-β-Pro$^7$-Ang III fully reversed the high salt-induced myofibroblast differentiation via an AT2R-sensitive mechanism as these effects were again blocked by the AT2R antagonist PD123313 (FIGS. 21 and 22).

Figure 23:
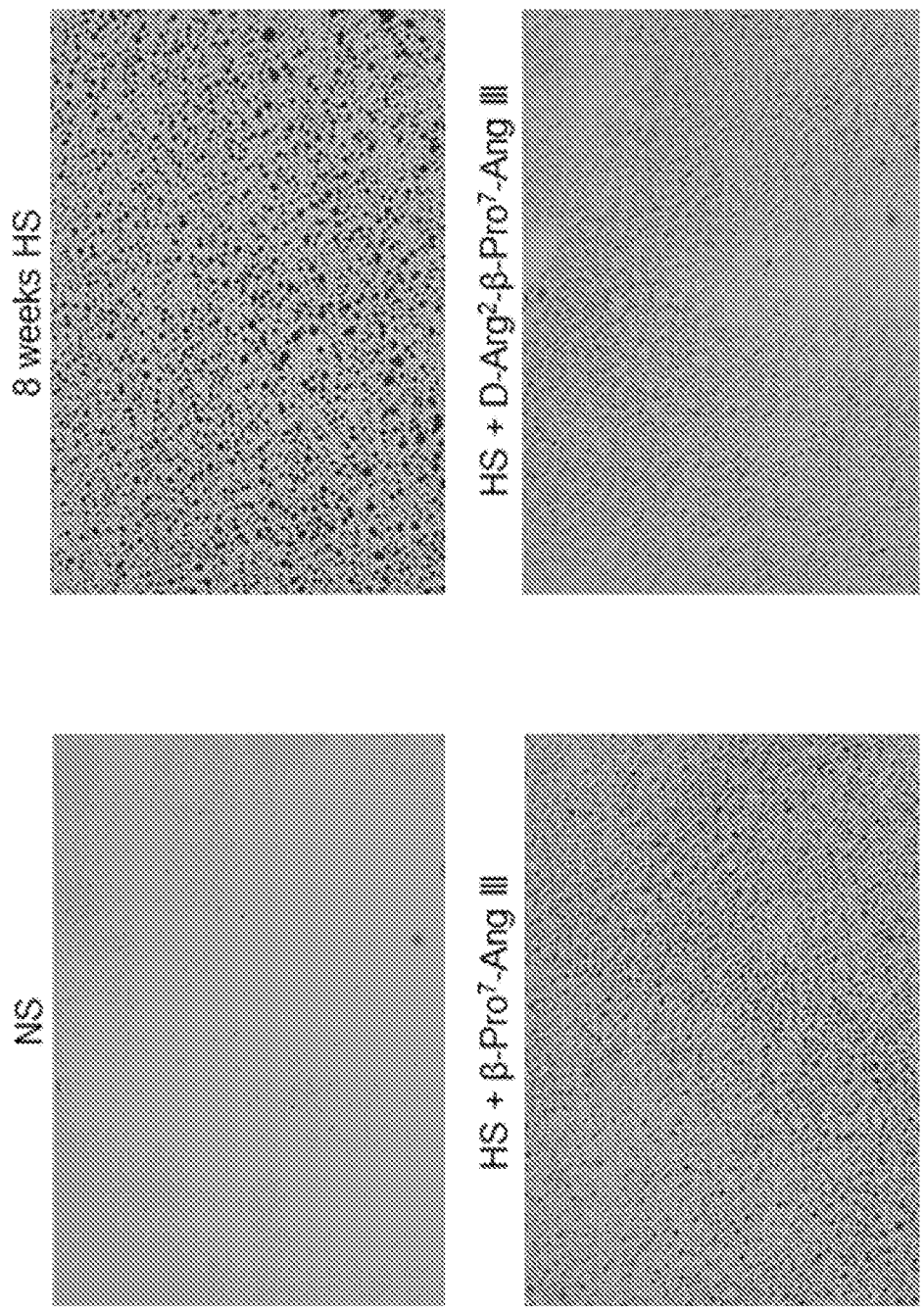
FIG. 23: Representative images of liver sections from male FVB/N mice that were either untreated (fed normal salt; NS); fed a high salt (5%) diet for 8 weeks or received either β-Pro$^7$-Ang III or D-Arg$^2$-β-Pro$^7$-Ang III (both at 75 pmol/kg/min subcutaneously via osmotic mini-pump) during weeks 5-8 while on a high salt diet. Transverse sections were stained with Oil Red 0 to indicate steatosis (fatty deposits). Macrovesicular steatosis is indicated by large red dots/circles.
Figure 24:
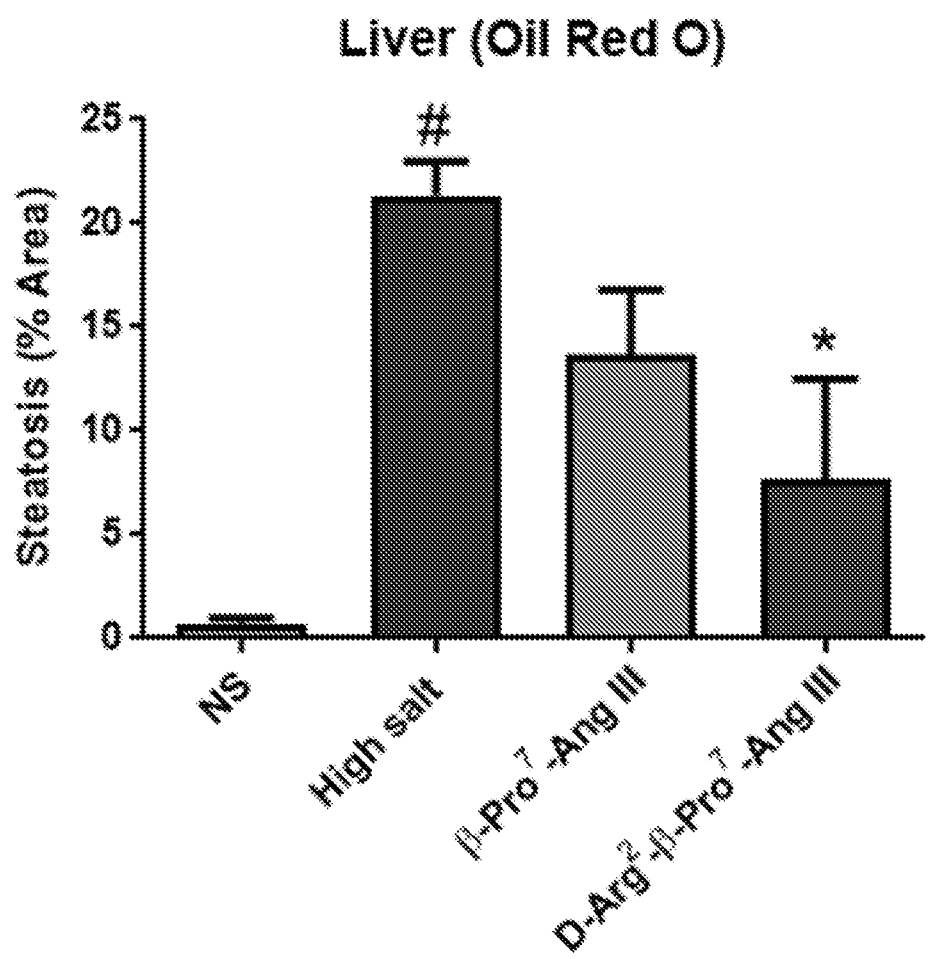
FIG. 24: AT2R stimulation by β-Pro$^7$-Ang III and D-Arg$^2$-β-Pro$^7$-Ang III attenuates high salt (5%)-mediated steatosis in mouse liver. Mean data for steatosis determined by Oil Red 0, taken from male FVB/N mice that were untreated (normal salt); fed a high salt diet for 8 weeks or received either β-Pro$^7$-Ang III or D-Arg$^2$-β-Pro$^7$-Ang III (both at 75 pmol/kg/min subcutaneously via osmotic mini-pump) during weeks 5-8 while on a high salt diet (n=5). High salt-induced liver steatosis was partially reversed by β-Pro$^7$-Ang III and D-Arg$^2$-β-Pro$^7$-Ang III. Data expressed as mean±s.e.m of percentage positive stained area for steatosis. #$P<0.05$ versus normal salt (NS); *$P<0.05$ versus high salt (one way ANOVA with Tukey's correction for multiple comparisons).
Figure 25:
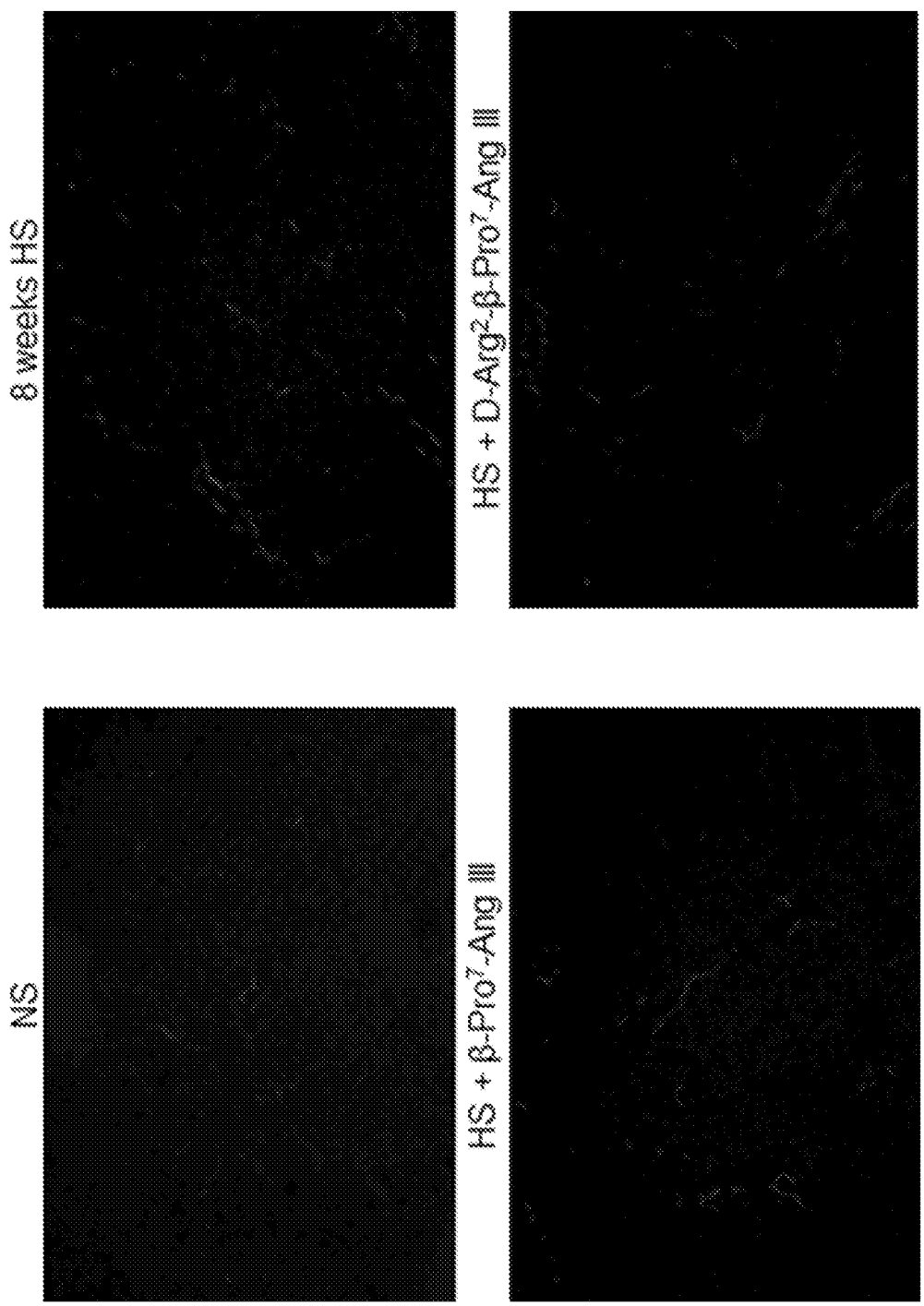
FIG. 25: Representative images of liver sections from male FVB/N mice that were either untreated (fed normal salt; NS); fed a high salt (5%) diet for 8 weeks or received either β-Pro$^7$-Ang III or D-Arg$^2$-β-Pro$^7$-Ang III (both at 75 pmol/kg/min subcutaneously via osmotic mini-pump) during weeks 5-8 while on a high salt diet. Transverse sections were stained with picrosirius red, under polarized light microscopy, to indicate collagen deposition.
Figure 26:
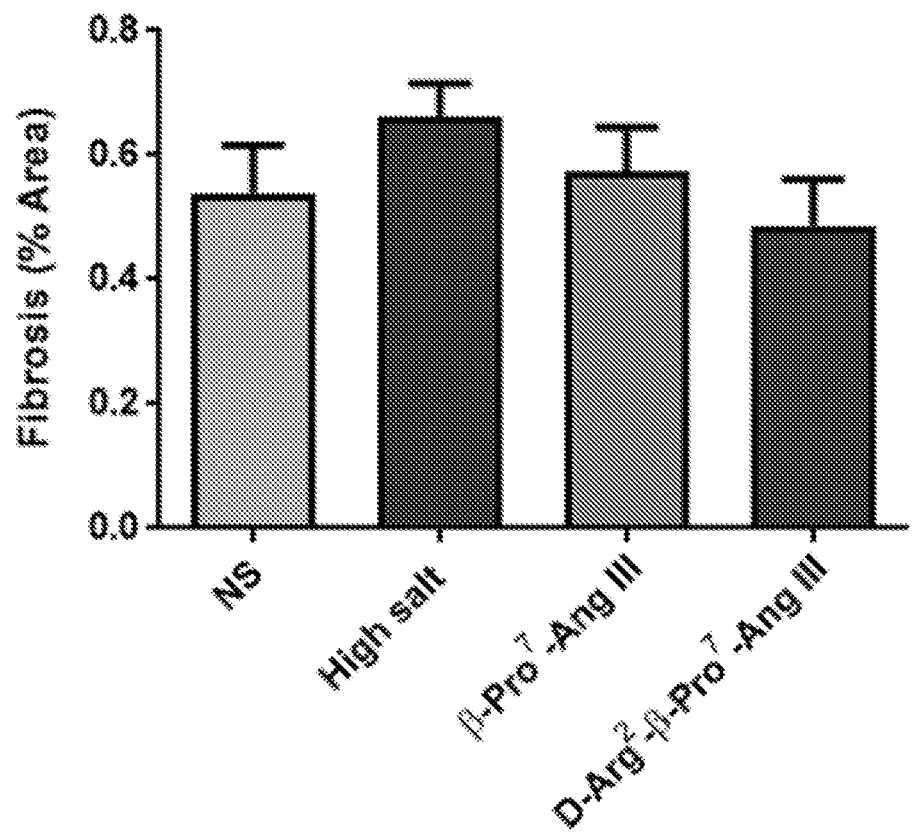
FIG. 26: AT2R stimulation by β-Pro$^7$-Ang III and D-Arg$^2$-β-Pro$^7$-Ang III appears to attenuate high salt (5%)-mediated fibrosis in mouse liver. Data for liver fibrosis determined by picrosirius red staining (under polarized light microscopy) shows that the pro-fibrotic effects of high salt were only modest in these experiments. Nevertheless, D-Arg$^2$-β-Pro$^7$-Ang III (75 pmol/kg/min subcutaneously via osmotic mini-pump) reversed liver fibrosis to untreated (normal salt) levels. Data expressed as mean±s.e.m of percentage positive stained area for fibrosis (n=6-8).

High salt induced marked steatosis (FIG. 23) but only mild liver fibrosis (FIG. 25) in these experiments. The highly AT2R selective and stable compound D-Arg$^2$-β-Pro$^7$-Ang III significantly reduced steatosis (FIG. 24) and normalised liver fibrosis (FIG. 26), albeit from a mildly fibrotic phenotype. Interestingly, D-Arg$^2$-β-Pro$^7$-Ang III appeared to be more effective at inhibiting lipid accumulation in the liver than β-Pro$^7$-Ang III, which may relate to enhanced hepatic metabolism of the less stable, β-Pro$^7$-Ang III.

Figure 27:
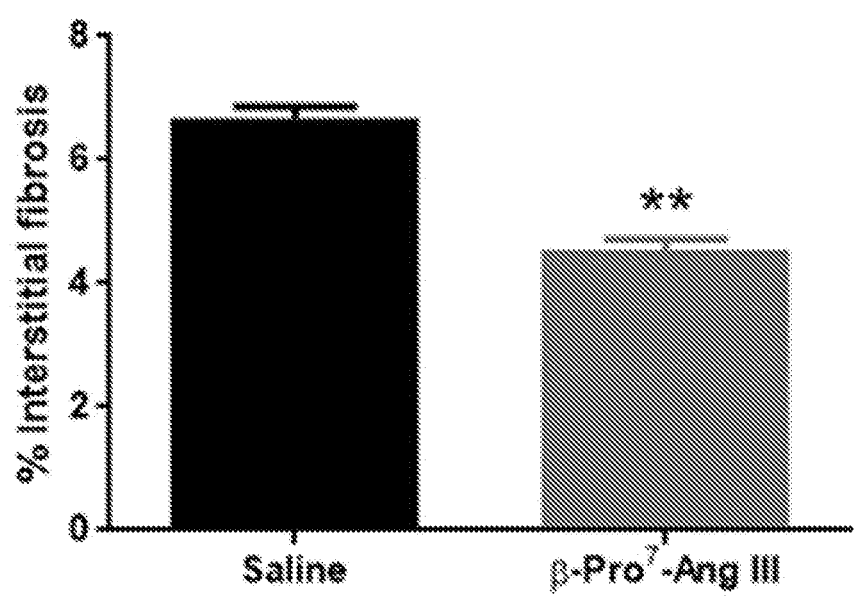
FIG. 27: AT2R stimulation by β-Pro$^7$-Ang III attenuates cardiac fibrosis in stroke-prone spontaneously hypertensive rats (SHRSP). Mean data for cardiac fibrosis determined by picrosirius red staining of transverse heart sections, under bright field microscopy, taken from ~25-week old, male stroke-prone spontaneously hypertensive rats (SHRSP) that received either saline or β-Pro$^7$-Ang III (75 pmol/kg/min subcutaneously via osmotic mini-pump) for 4 weeks (n=3-4). Data expressed as mean±s.e.m of percentage positive stained area for fibrosis. **P<0.01 versus saline (unpaired t-test).

For the first time, β-Pro$^7$-Ang III was tested at the same dose, duration and route of administration (75 pmol/kg/min subcutaneously via osmotic mini-pump for 4 weeks) in adult male stroke-prone spontaneously hypertensive rats (SHRSP). This rat model exhibits elevated blood pressure and is a conventional model to examine antihypertensive drug effects and organ remodelling. In these experiments, β-Pro$^7$-Ang III significantly reduced cardiac fibrosis, assessed by picrosirius red staining (FIG. 27), indicating that AT2R stimulation with β-Pro$^7$-Ang III and related compounds will reduce cardiac fibrosis in a variety of models. However, this peptide did not affect SBP.

Example 7

Figure 28:
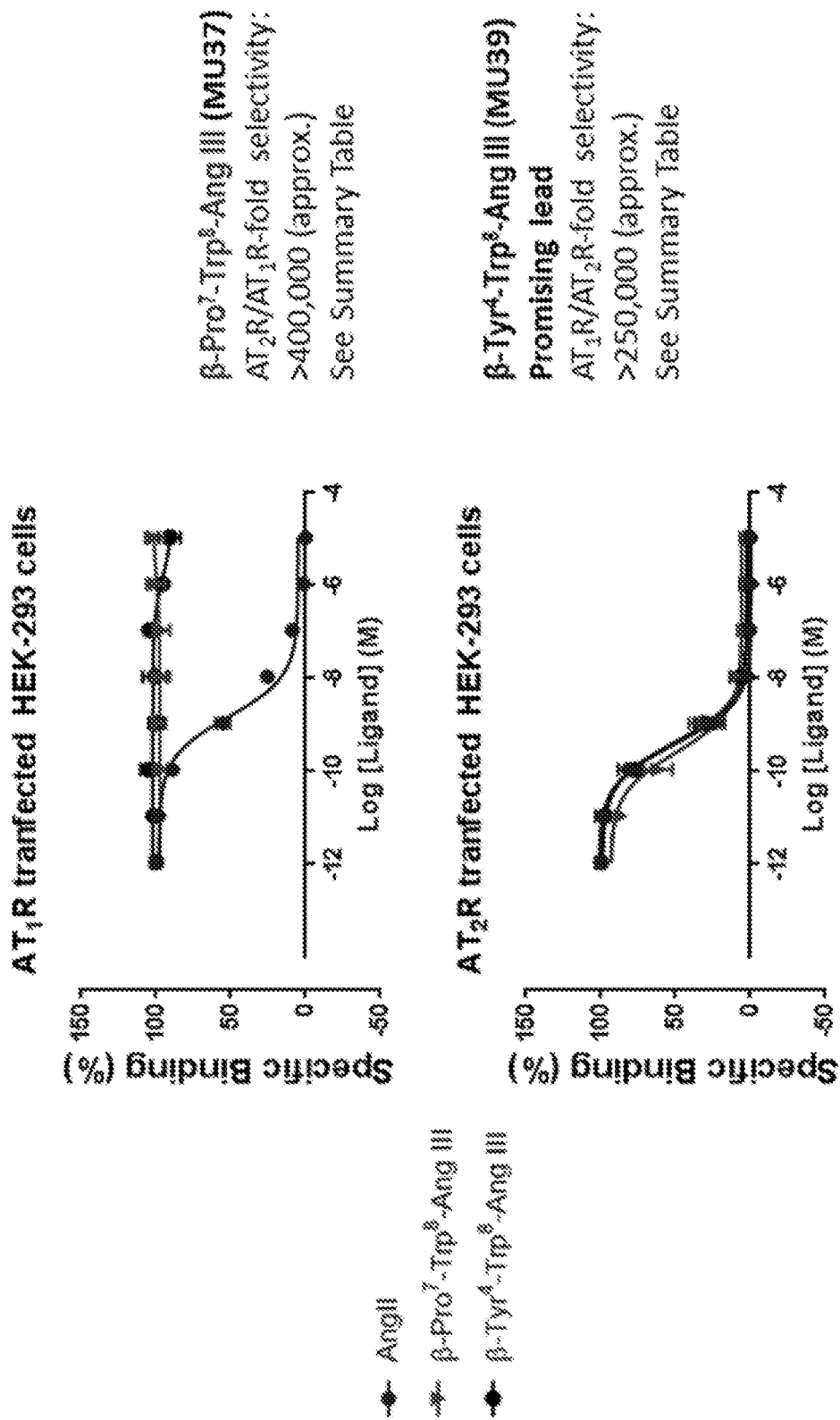
FIG. 28: Competition radioligand binding assays to determine the ability of β-Pro$^7$-Trp$^8$-Ang III, β-Tyro-Trp$^8$-Ang III and Ang II to displace the nonselective iodinated ligand $^{125}$I-Sar$^1$-Ile$^8$-AngII from either AT1R (top panel) or AT2R (bottom panel) in transfected HEK-293 cells. Typically, the ability of compounds of interest to displace the Ang II radioligand from both AT1R and AT2R will lead to the generation of IC50 values that determine the relative ability of test compounds to interact with both receptors. In this instance, Ang II readily binds to both AT1R and AT2R, whereas both β-Pro$^7$-Trp$^8$-Ang III and β-Tyr$^4$-Trp$^8$-Ang III bind poorly at AT1R, but with high affinity at AT2R. This results in relative selectivities of β-Pro$^7$-Trp$^8$-Ang III and β-Tyr$^4$-Trp$^8$-Ang III for AT2Rs over AT1R that are conservatively estimated at >250,000-400,000-fold (see Table 3).
Figure 29:
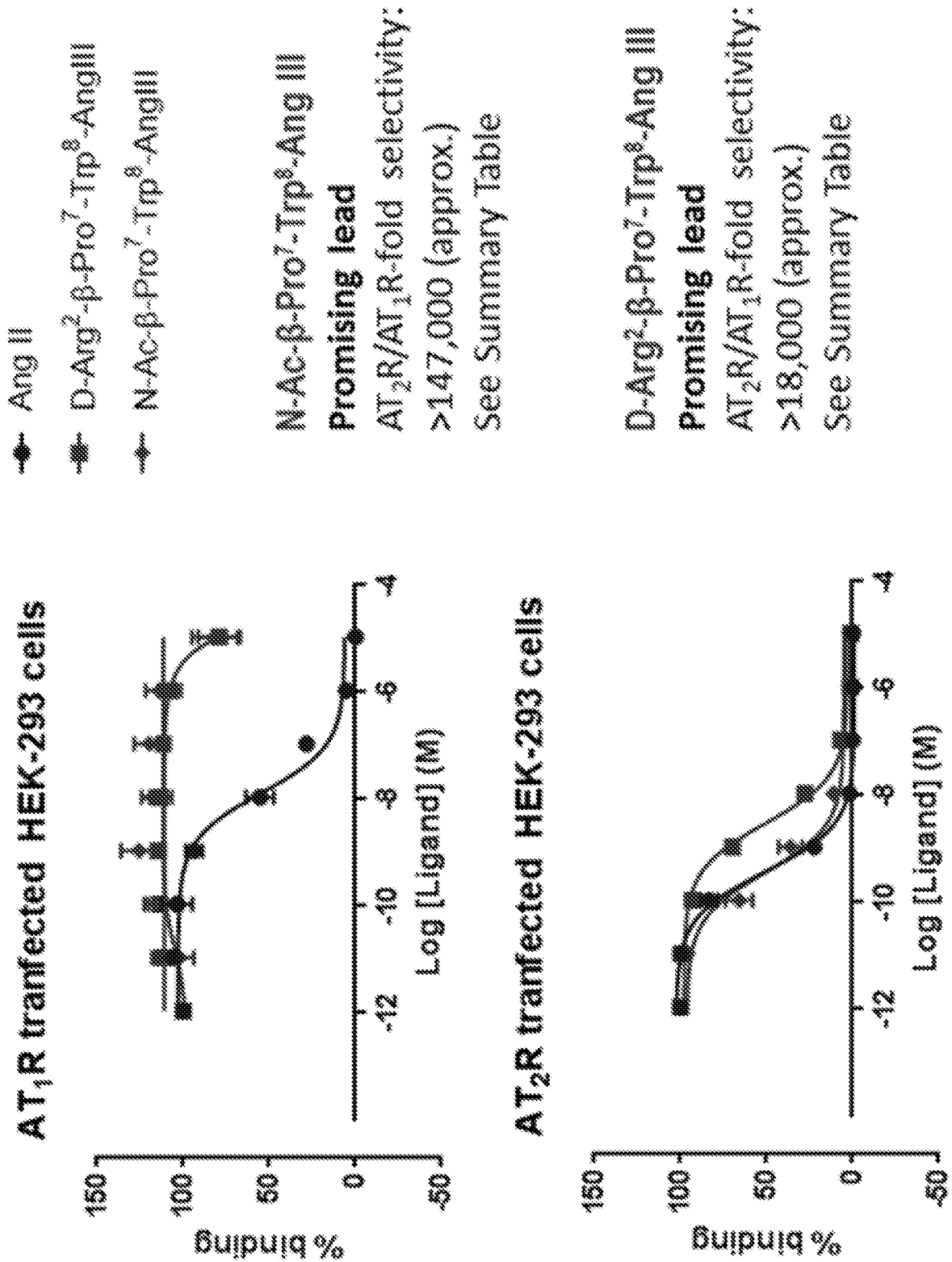
FIG. 29: Competition radioligand binding assays to determine the ability of N—Ac—Pro$^7$-Trp$^8$-Ang III, D-Arg$^2$-β-Pro$^7$-Trp$^8$-Ang III and Ang II to displace the nonselective iodinated ligand $^{125}$I-Sar$^1$-Ile$^8$-AngII from either AT1R (top panel) or AT2R (bottom panel) in transfected HEK-293 cells. In this instance, Ang II readily binds to both AT1R and AT2R, whereas both N—Ac—Pro$^7$-Trp$^8$-Ang III and D-Arg$^2$-β-Pro$^7$-Trp$^8$-Ang III bind poorly at AT1R, but with high affinity at AT2R. This results in relative selectivities of N—Ac—Pro$^7$-Trp$^8$-Ang III and D-Arg$^2$-β-Pro$^7$-Trp$^8$-Ang III for AT2R over AT1R that are conservatively estimated at >18,000-147,000-fold (see Table 3).
Figure 36:
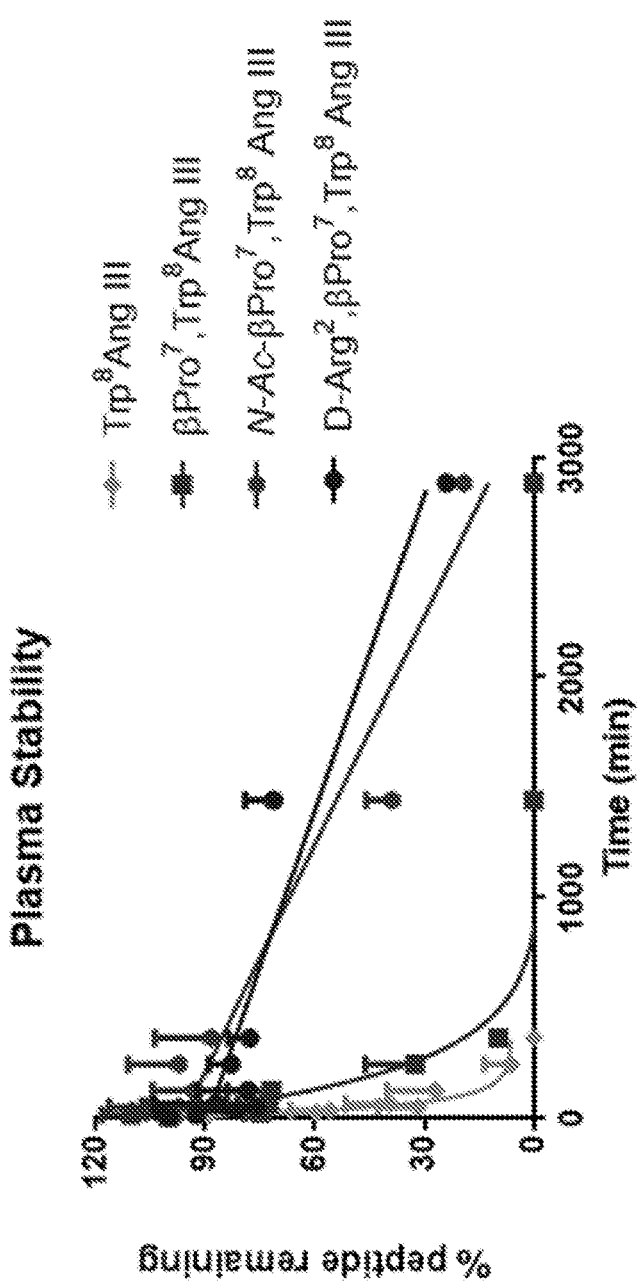
FIG. 36: In vitro plasma stability of various lead compounds. The peptides were incubated for various times in plasma obtained from male spontaneously hypertensive rats (SHR). Approximate plasma half lives are listed for each compound (n=3).

Radioligand Binding Profiles at AT1R and AT2R of a Number of n-Substituted Ang III Derivatives, and Examples Demonstrating that Novel AT2R Agonists Exert Anti-Fibrotic Effects in the Heart and Kidney A number of modifications to the β-Pro$^7$-Ang III template and a β-Trp$^8$-Ang III template have been synthesised and their AT2R:AT1R selectivities determined. In particular binding profiles are provided for β-Pro$^7$-Trp$^8$-Ang III and β-Tyro-Trp$^8$-Ang III (FIG. 28) and N—Ac—β-Pro$^7$-Trp$^8$-Ang III and D-Arg$^2$-β-Pro$^7$-Trp$^8$-Ang III (FIG. 29), together with their plasma stability (FIG. 36). These ligands exhibit exquisite AT2R selectivity ranging from >18,000-fold to >400,000-fold selective for AT2R (e.g. β-Pro$^7$-Trp$^8$-Ang III). These values may in fact underestimate the respective AT2R:AT1R selectivity ratios since there was often minimal AT1R binding at 10 μM. Additionally, a number of these novel peptides were highly stable with half-lives >25 hours (FIG. 36).

Figure 30:
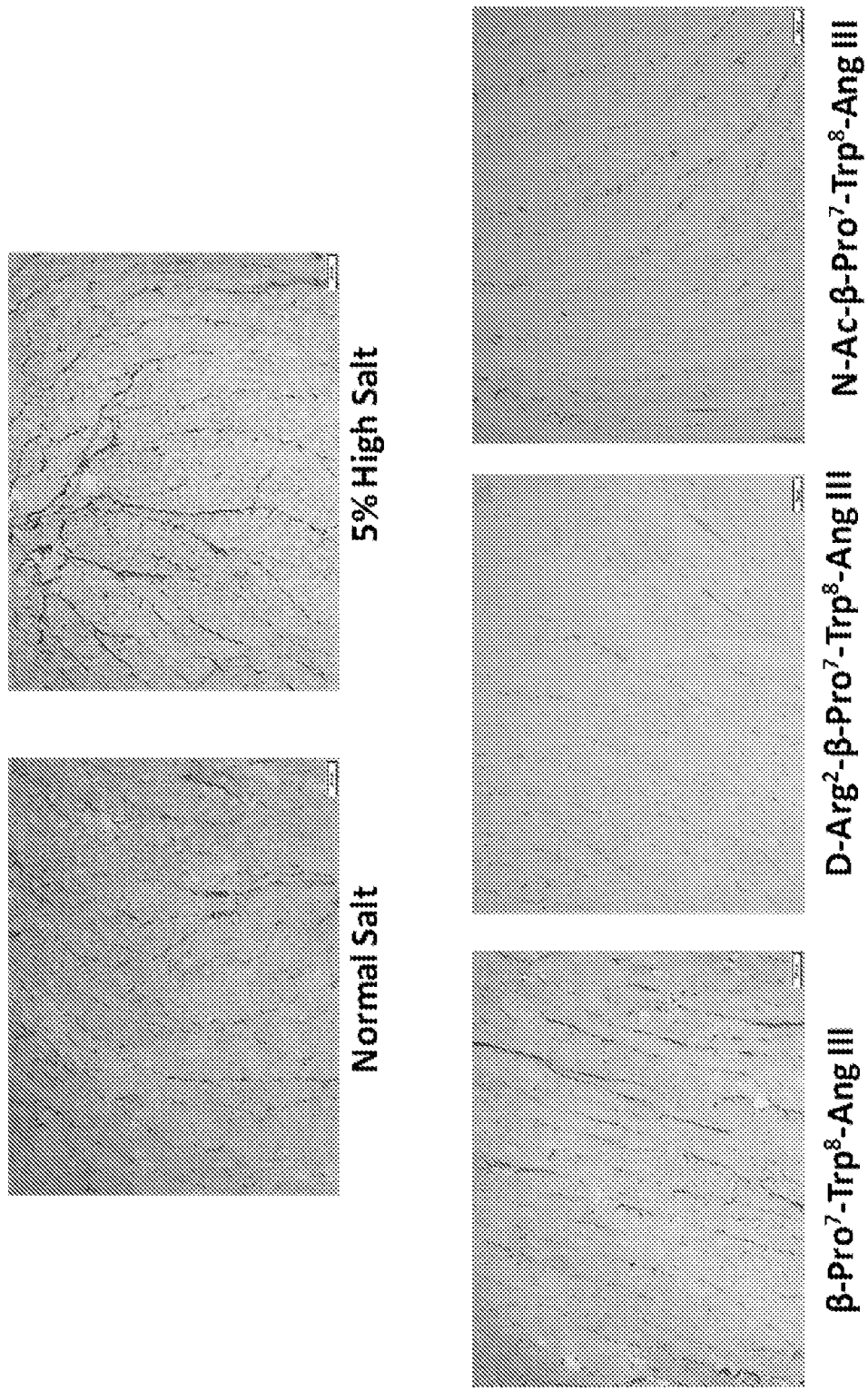
FIG. 30: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated fibrosis in mouse heart. Representative images are shown of transverse heart sections stained for collagen using picrosirius red (PSR) under bright field microscopy, taken from male FVB/N mice that were untreated (normal salt); fed a high salt diet for 8 weeks or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet.
Figure 31:
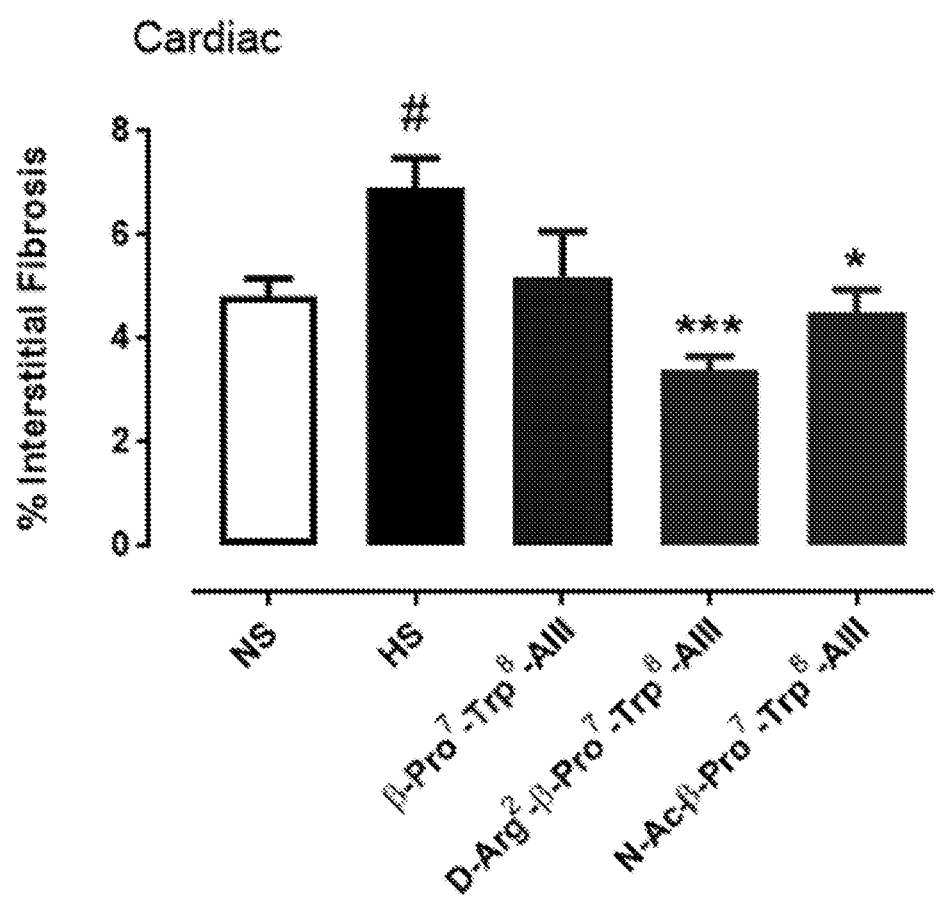
FIG. 31: AT2R stimulation by β-Pro$^7$-Trp$^8$-Ang III, D-Arg$^2$-β-Pro$^7$-Trp$^8$-Ang III or N—Ac—β-Pro$^7$-Trp$^8$-Ang III attenuates high salt (5%)-mediated fibrosis in mouse heart. Mean data for cardiac fibrosis determined by picrosirius red, under bright field microscopy, taken from male FVB/N mice that were untreated (normal salt; NS); fed a high salt diet for 8 weeks (HS) or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=7-9). All three AT2R agonists reversed the pro-fibrotic effects of high salt in the heart. Data expressed as mean±s.e.m of percentage positive stained area for fibrosis. #P<0.05 versus normal salt (NS); *P<0.05, ***P<0.001 versus high salt (one way ANOVA with Tukey's correction for multiple comparisons).

A number of compounds were tested as a 4-week treatment intervention against high salt-induced cardiac and renal fibrosis, as already described. In this study, β-Pro$^7$-Trp$^8$-Ang III, D-Arg$^2$-β-Pro$^7$-Trp$^8$-Ang III, and N—Ac—β-Pro$^7$-Trp$^8$-Ang III all reversed cardiac fibrosis (FIGS. 30 and 31). Further analysis of β-Pro$^7$-Trp$^8$-Ang III, D-Arg$^2$-β-

Figure 32:
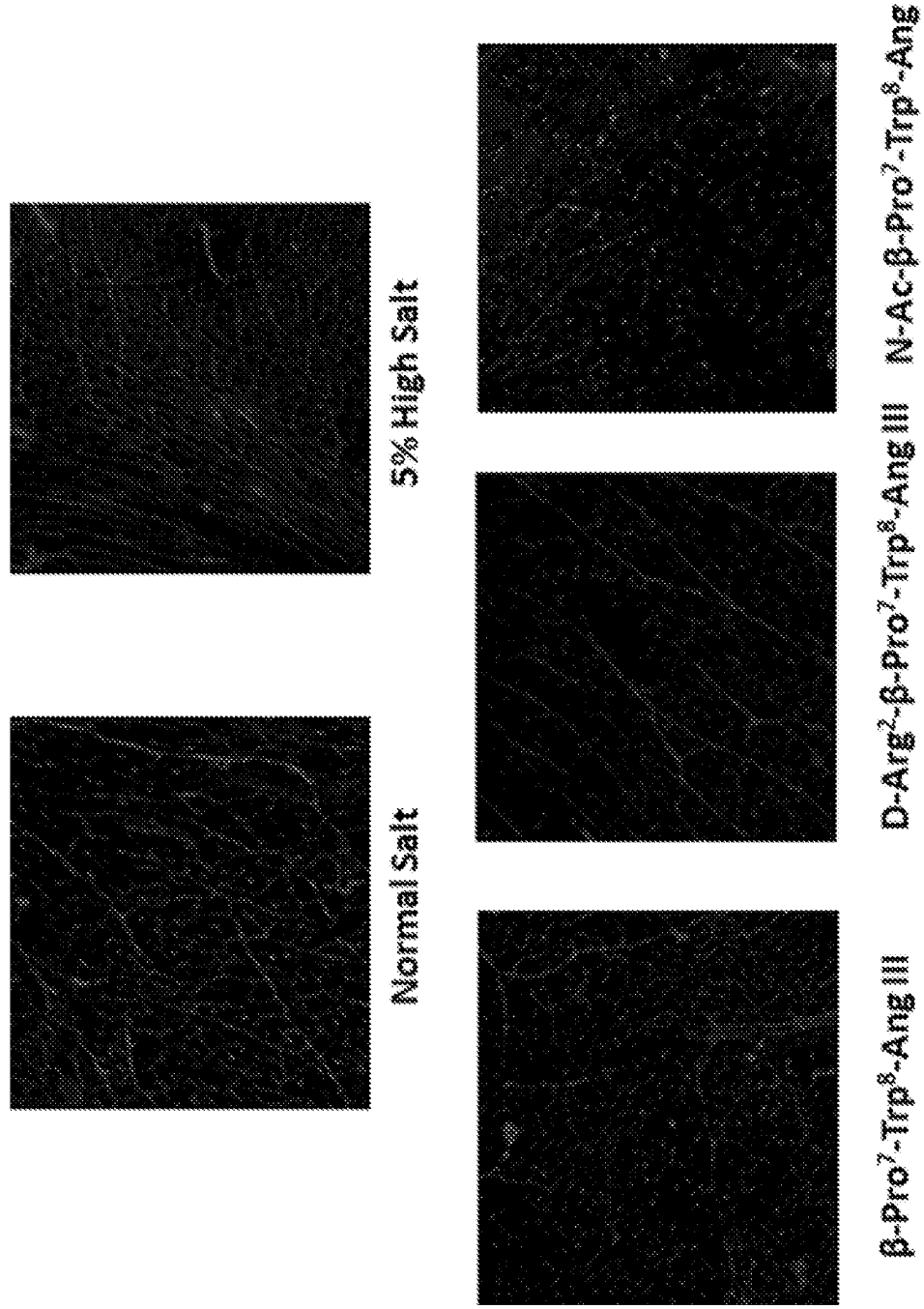
FIG. 32: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated myofibroblast differentiation in mouse heart. Representative images are shown of transverse heart sections with positive stained immunofluorescence of myofibroblast differentiation determined by α-SMA (marker for myofibroblast expression), taken from male FVB/N mice that were untreated (normal salt); fed a high salt diet for 8 weeks or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet.
Figure 33:
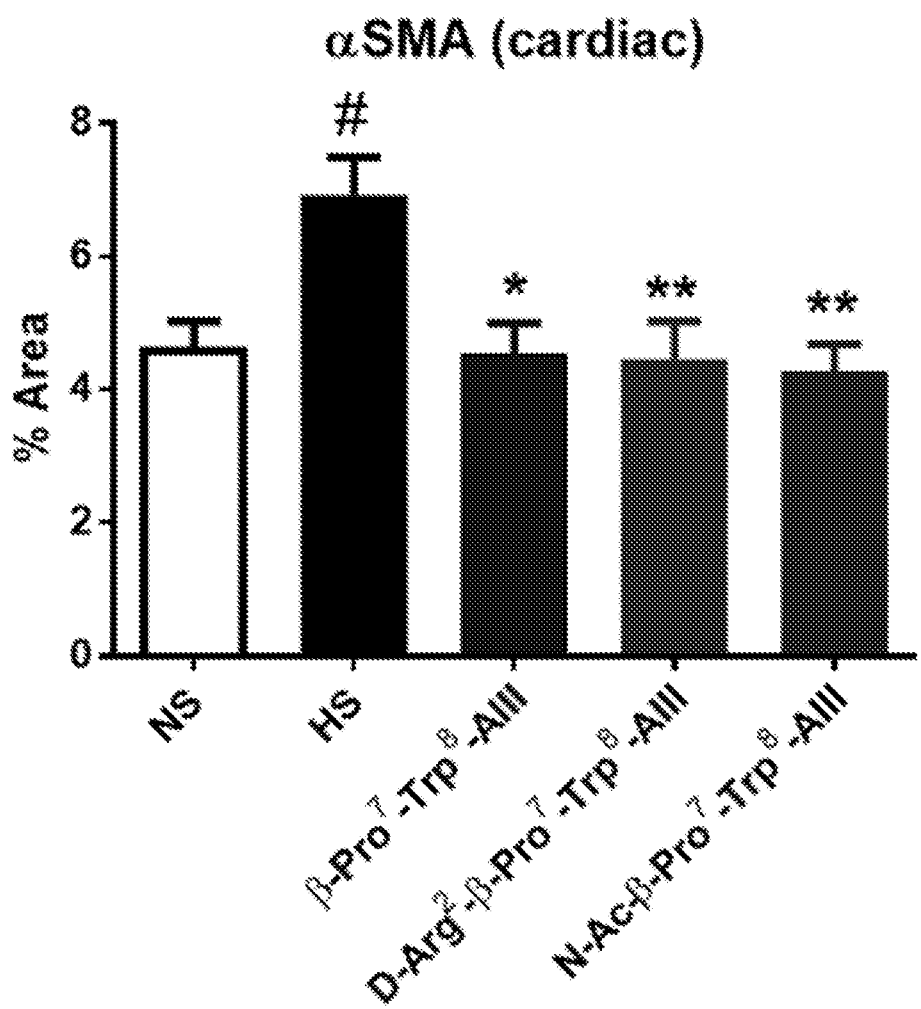
FIG. 33: AT2R stimulation by β-Pro$^7$-Trp$^8$-Ang III, D-Arg$^2$-β-Pro$^7$-Trp$^8$-Ang III or N—Ac—β-Pro$^7$-Trp$^8$-Ang III attenuates high salt (5%)-mediated myofibroblast differentiation in mouse heart. Mean data for myofibroblast differentiation determined by α-SMA, taken from male FVB/N mice that were untreated (normal salt; NS); fed a high salt diet for 8 weeks (HS) or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=7-9). All three AT2R agonists reversed the myofibroblast differentiation caused by high salt in the heart. Data expressed as mean±s.e.m of percentage positive stained area for α-SMA. #P<0.05 versus normal salt (NS); *P<0.05, **P<0.01 versus high salt (HS) (one way ANOVA with Tukey's correction for multiple comparisons).
Figure 34:
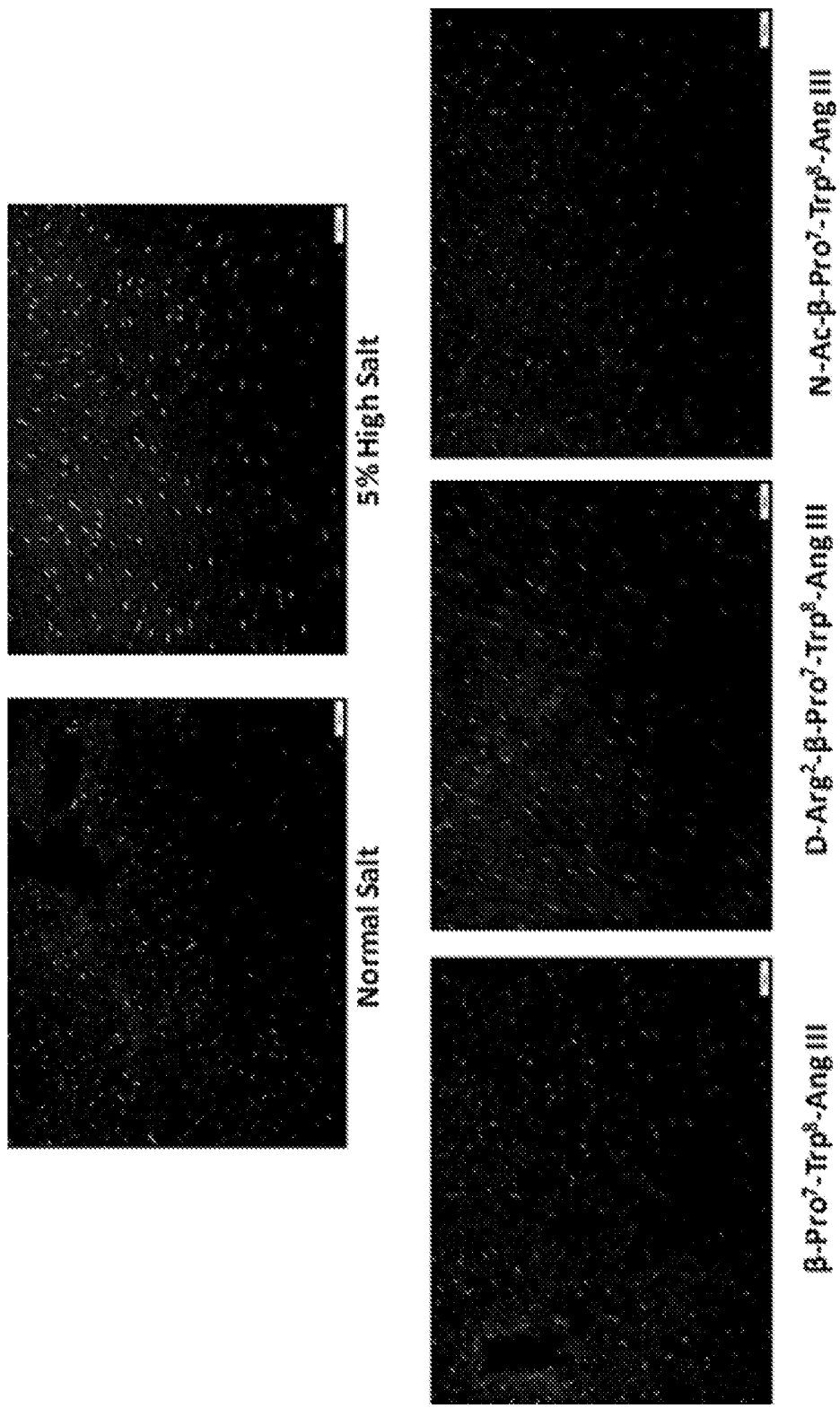
FIG. 34: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated inflammation in mouse heart. Representative images are shown of positive stained immunofluorescence in transverse heart sections by measuring the pro-inflammatory marker NFκB (measured via phospho-IκBα expression using immunofluorescence staining), taken from male FVB/N mice that were untreated (normal salt); fed a high salt diet for 8 weeks or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet.
Figure 35:
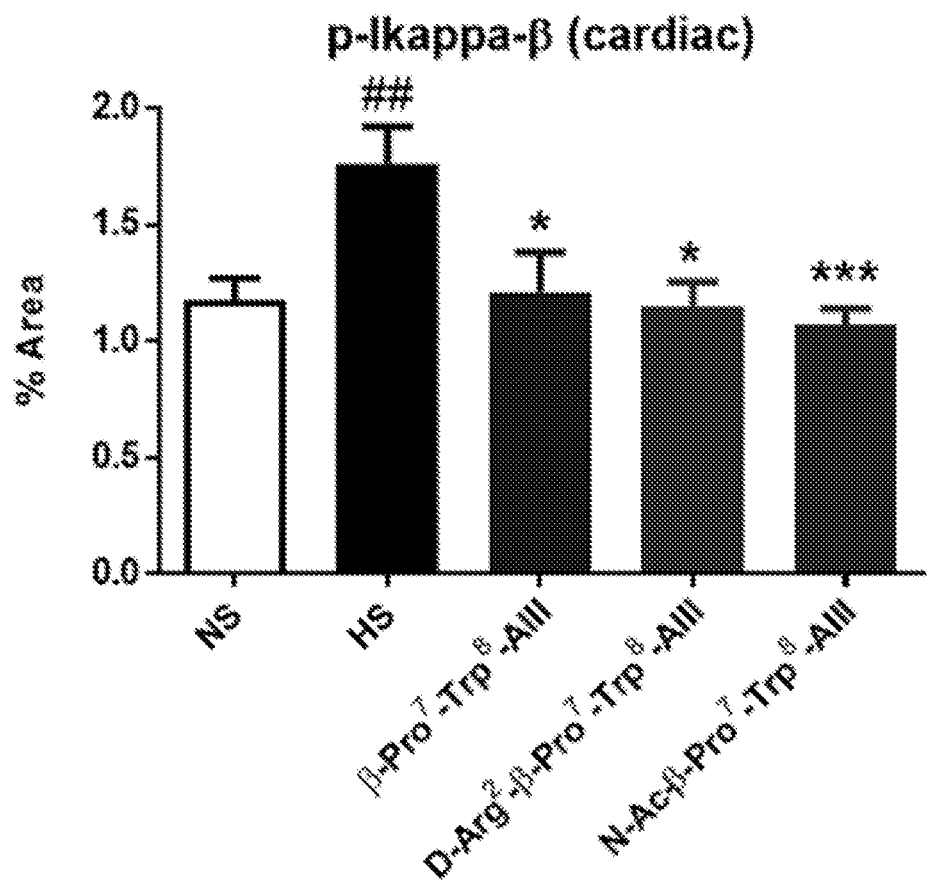
FIG. 35: AT2R stimulation by β-Pro$^7$-Trp$^8$-Ang III, D-Arg$^2$-β-Pro$^7$-Trp$^8$-Ang III or N—Ac—β-Pro$^7$-Trp$^8$-Ang III attenuates high salt (5%)-mediated inflammation in mouse heart. Quantification of positive stained immunofluorescence in transverse heart sections by measuring the pro-inflammatory marker NFκB (measured via phospho-IκBα expression using immunofluorescence staining), taken from male FVB/N mice that were untreated (normal salt; NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=6-9). All three AT2R agonists reversed the cardiac inflammation caused by high salt in the heart. Data expressed as mean±s.e.m of percentage positive stained area. ##P<0.01 versus normal salt (NS); *P<0.05, ***P<0.001 versus high salt (HS) (one way ANOVA with Tukey's correction for multiple comparisons).

Pro⁷-Trp⁸-Ang III, and N—Ac—β-Pro⁷-Trp⁸-Ang III revealed that these peptides reversed myofibroblast differentiation (FIGS. 32 and 33) and expression of P-IκBα (marker for NFκB activation) (FIGS. 34 and 35) induced by high salt. Analogous anti-fibrotic and anti-inflammatory effects also occurred in the kidneys following 4-week treatment intervention with these three compounds in the high salt-fed model.

Figure 37:
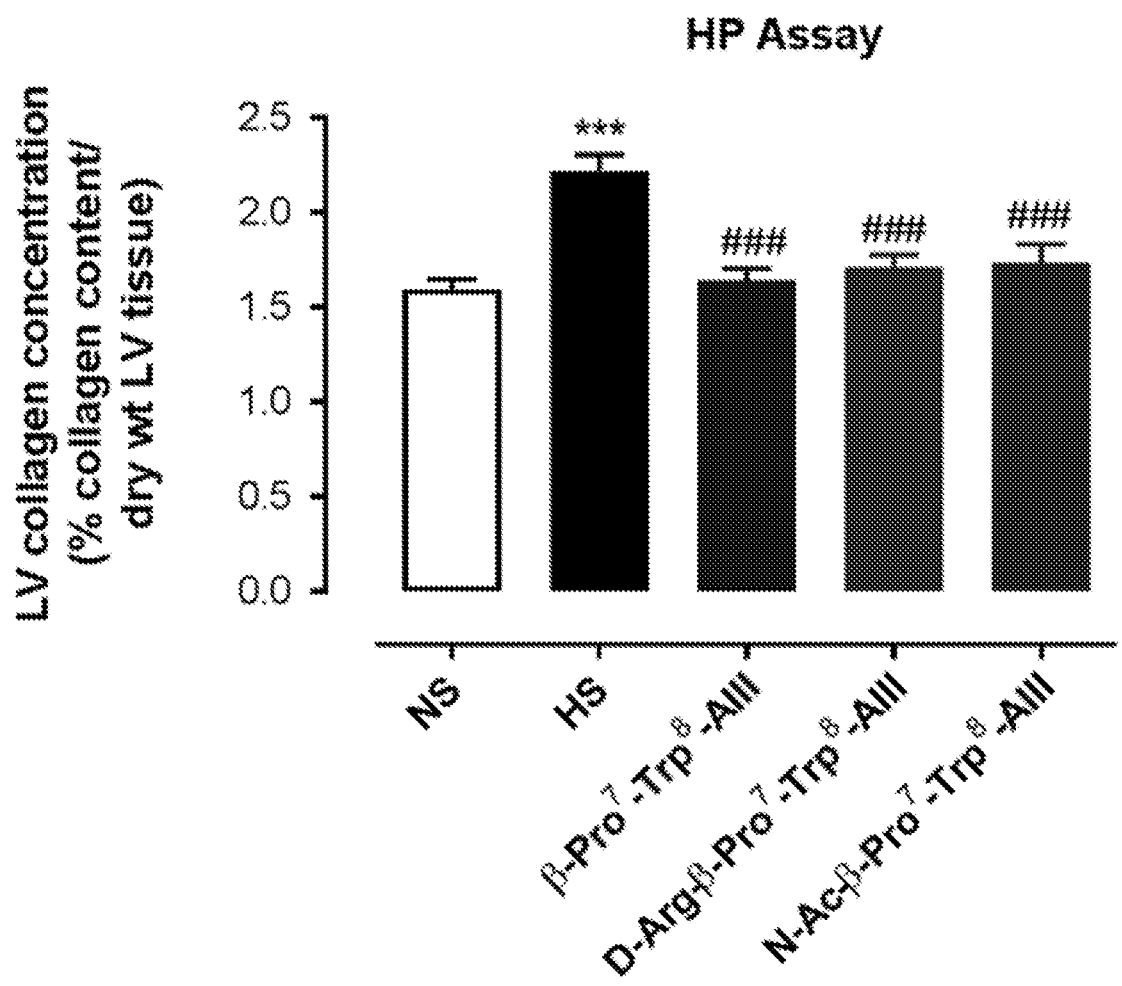
FIG. 37: AT2R stimulation by β-Pro$^7$-Trp$^8$-Ang III, D-Arg$^2$-β-Pro$^7$-Trp$^8$-Ang III or N—Ac—β-Pro$^7$-Trp$^8$-Ang III attenuates high salt (5%)-mediated fibrosis in mouse heart. Mean data for cardiac fibrosis determined by hydroxyproline (HP) analysis, taken from male FVB/N mice that were untreated (normal salt; NS); fed a high salt diet for 8 weeks (HS) or received β-Pro$^7$-Trp$^8$-Ang III, D-Arg$^2$-β-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=7-8). All three AT2R agonists reversed the pro-fibrotic effects of high salt in the heart. Data expressed as mean±s.e.m of left ventricle (LV) % collagen content normalised to LV weight. ***P<0.001 versus NS; ###P<0.001 versus HS (one way ANOVA with Tukey's correction for multiple comparisons).
Figure 38:
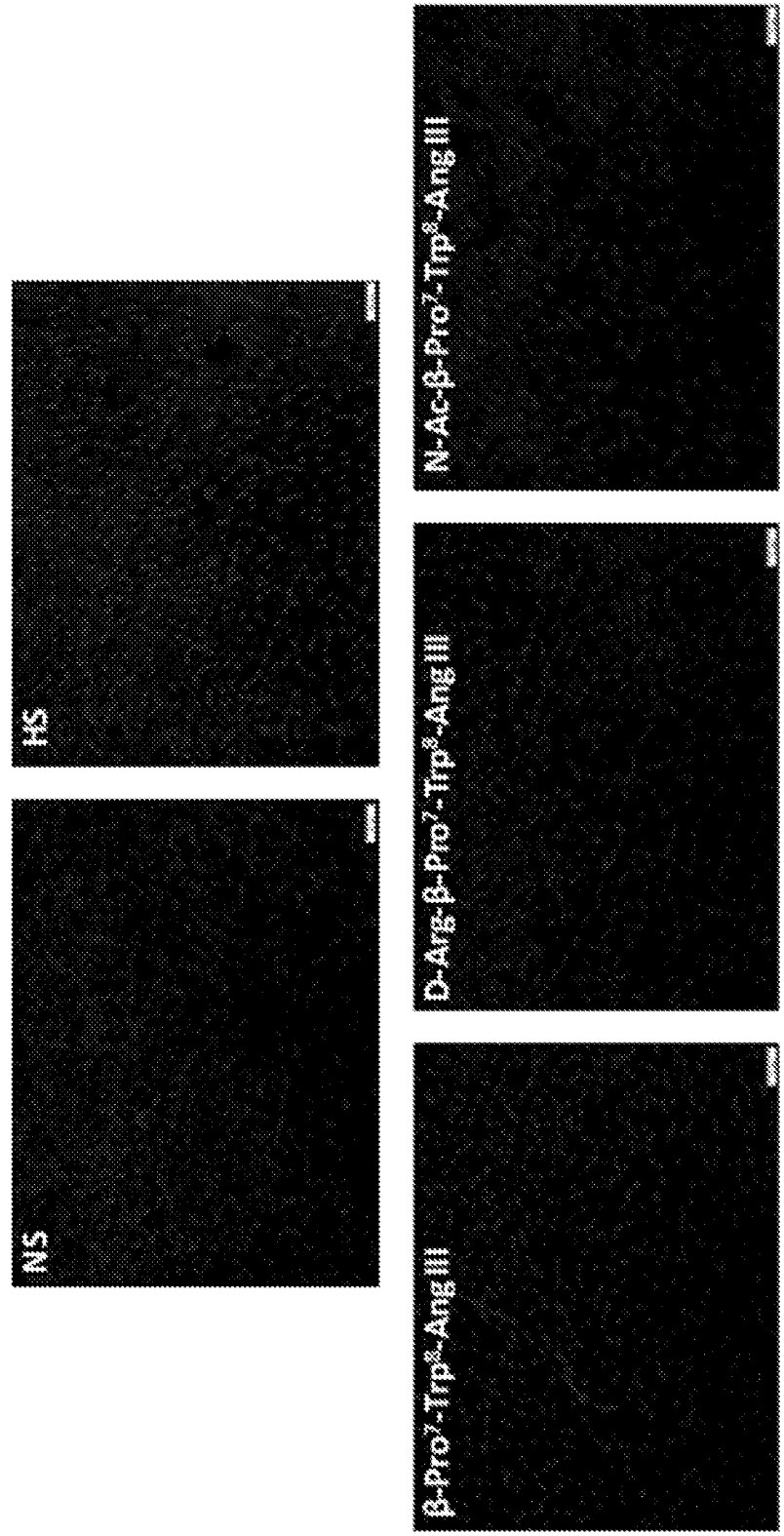
FIG. 38: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated oxidative stress in mouse heart. Left-hand panel: Representative images are shown of transverse heart sections stained for dihydroethedium (DHE), as a measure of oxidative stress, taken from male FVB/N mice that were untreated (normal salt, NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet. Right-hand panel: Mean data for cardiac oxidative stress, taken from male FVB/N mice that were untreated (normal salt; NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=5-7). All three AT2R agonists reversed the oxidative stress effects of high salt in the heart. Data expressed as mean±s.e.m of percentage positive stained area for DHE. ** P<0.01 versus normal salt (NS); #P<0.05 versus high salt (one way ANOVA with Tukey's correction for multiple comparisons).
Figure 38:
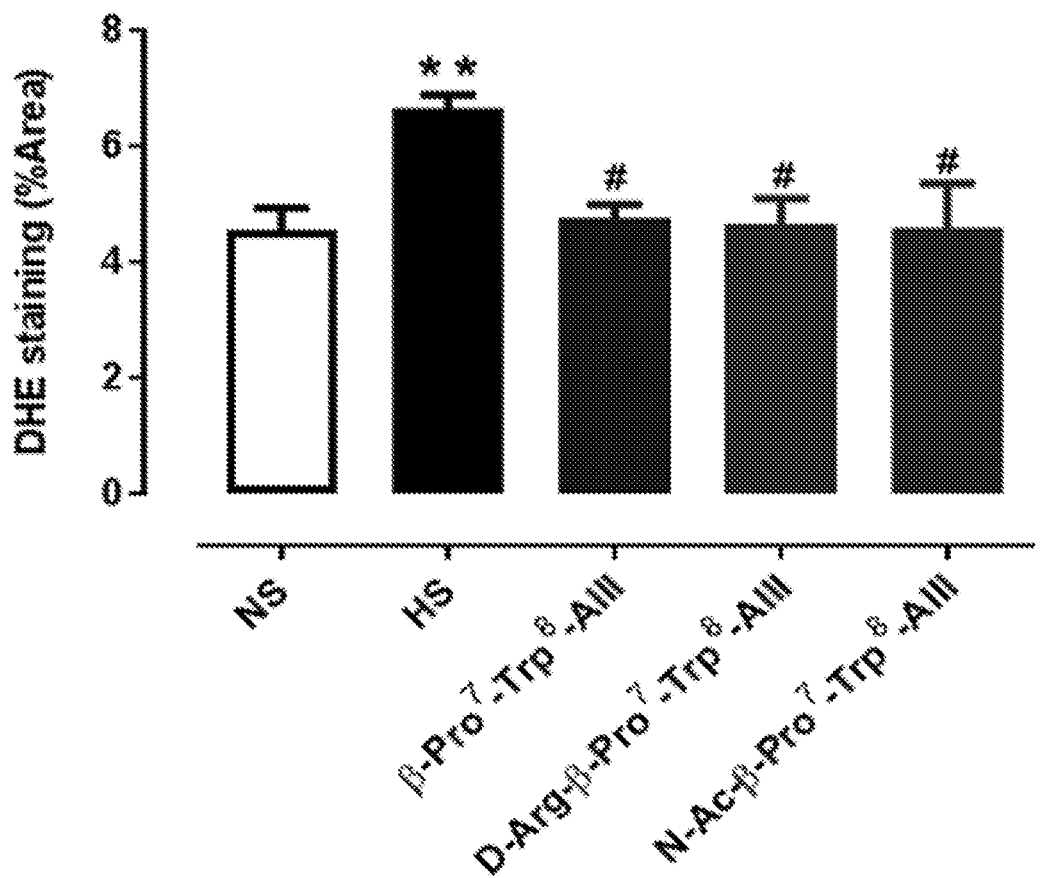
Figure 39:
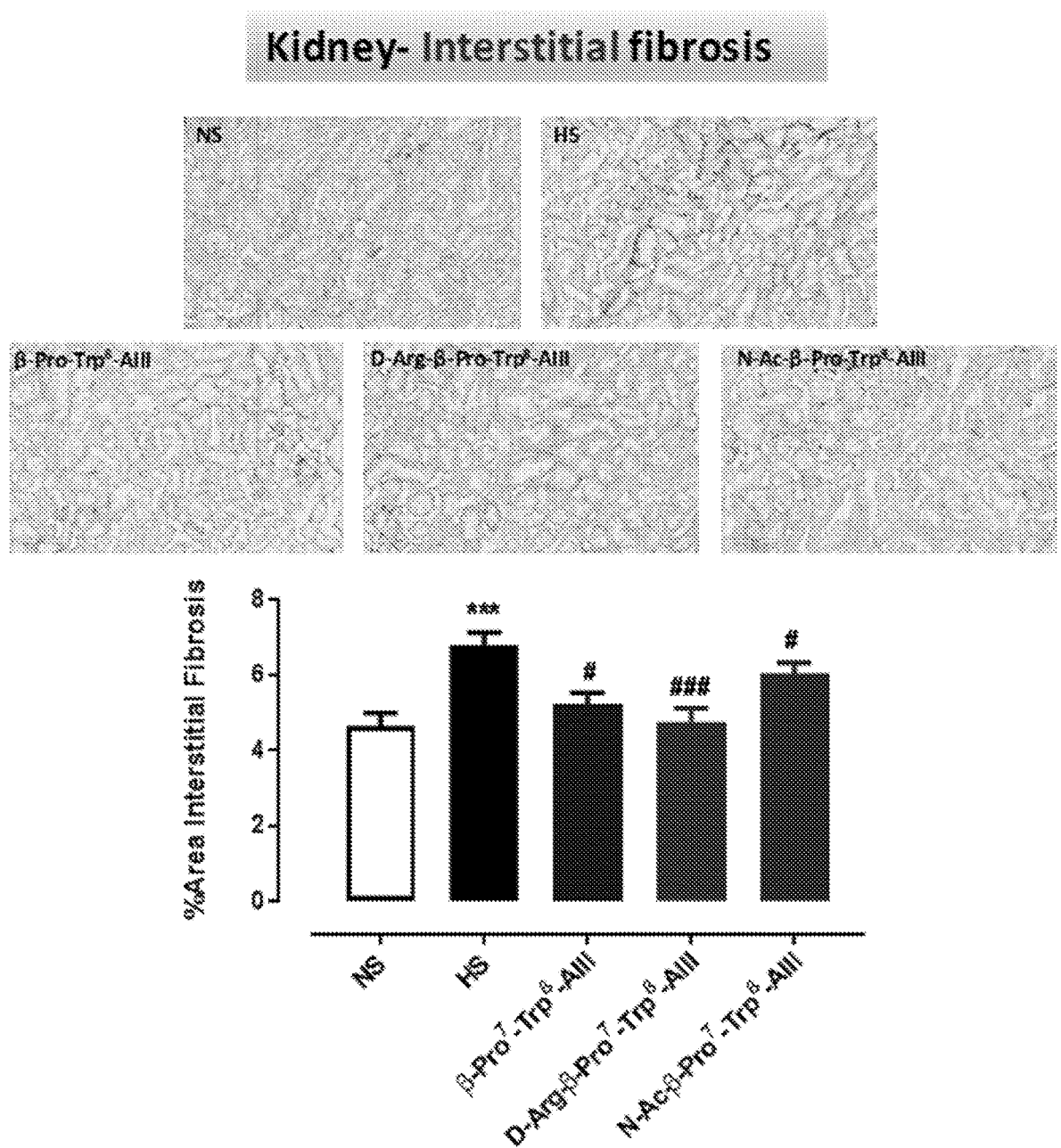
FIG. 39: β-Pro$^7$-Trp$^8$-Ang III, D-Arg$^2$-β-Pro$^7$-Trp$^8$-Ang III and N—Ac—β-Pro$^7$-Trp$^8$-Ang III attenuates high salt (5%)-mediated fibrosis in mouse kidney. Left-hand panel: Representative images are shown of transverse kidney sections stained for tubulointerstitial fibrosis determined by picrosirius red, under bright field microscopy, taken from male FVB/N mice that were untreated (normal salt, NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet. Corresponding mean data are shown below for renal tubulointerstitial fibrosis, taken from male FVB/N mice that were untreated (normal salt; NS); fed a high salt diet for 8 weeks (HS) or received β-Pro$^7$-Trp$^8$-Ang III, D-Arg$^2$-δ-Pro$^7$-Trp$^8$-Ang III or N—Ac—β-Pro$^7$-Trp$^8$-Ang III (each 75 pmol/kg/min subcutaneously via osmotic mini-pump) during weeks 5-8 while on a high salt diet (n=6-10). All three AT2R agonists reversed the tubulointerstitial fibrosis caused by high salt in the kidney. Data expressed as mean±s.e.m of percentage positive tubulointerstitial area stained for picrosirius red. *** P<0.001 versus normal salt (NS); #P<0.05, ###P<0.001 versus high salt (one way ANOVA with Tukey's correction for multiple comparisons).
Figure 39:
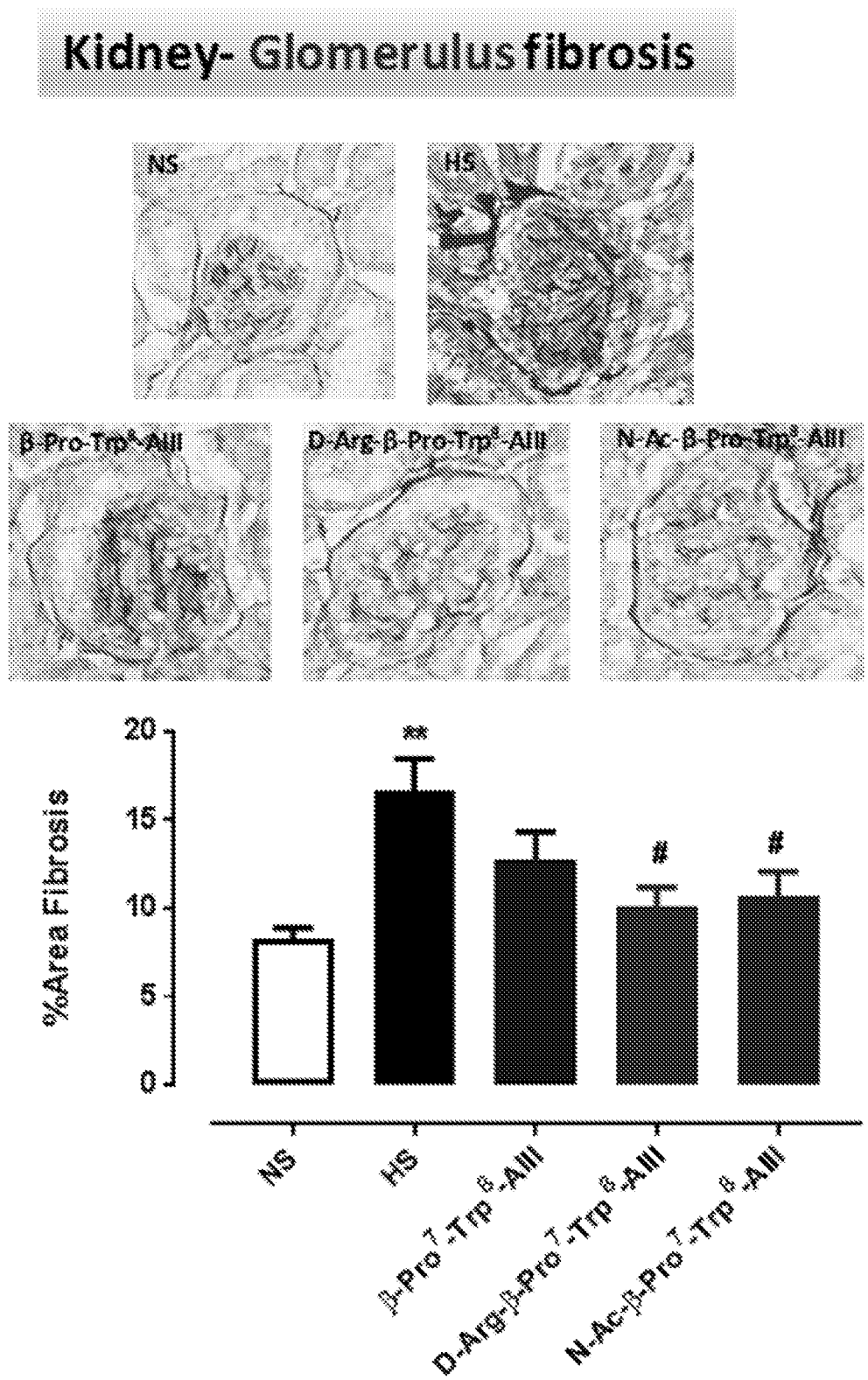

All three AT2R selective agonists:
- reversed the pro-fibrotic effects of high salt in the heart, determined by hydroxyproline analysis (FIG. 37);
- reversed the oxidative stress effects of high salt in the heart (FIG. 38);
- reversed the tubulointerstitial and glomerular fibrosis caused by high salt in the kidney (FIG. 39);
- reversed the pro-fibrotic effects of high salt in the kidney, determined by hydroxyproline analysis (FIG. 40);
- reversed high salt-induced macrophage infiltration in the kidney (FIG. 41); and
- reversed high salt-induced renal inflammation in the kidney (FIG. 42).

The inventors have demonstrated that a number of unique angiotensin-derived compounds exhibit very high selectivity for AT2Rs. Extensive data is provided herein in which AT2R stimulation reversed established cardiac fibrosis and similar anti-fibrotic effects were noted in kidney and liver and a marked reduction in hepatic steatosis. The strength of the current study is the demonstration that pharmacological stimulation of AT2Rs by a number of unique, selective AT2R agonists reversed established cardiac fibrosis in a similar manner. An excessive buildup of collagen exacerbates cardiac stiffness and decreases compliance leading to cardiac dysfunction which may lead to CHF or impede recovery from MI, or contribute to impaired renal function. This situation is exacerbated by hypertension and by senescence.

Organ fibrosis is multifactorial, with tissue injury involving a complex interplay between pro-fibrotic cytokines such as TGF-β1 and other inflammatory mediators, which then act synergistically to increase ECM deposition. Therefore, pharmacological treatment to reverse existing ECM and organ dysfunction is highly desirable and is currently an unmet clinical need. It is well described in experimental and clinical literature that AT2R expression is increased in cardiovascular and renal disease and such enhanced AT2R expression is thought to be a compensatory response to offset deleterious AT1R-mediated effects. The clinical relevance of AT2R as a therapeutic target was confirmed by the results herein since selective AT2R agonists described herein were able to fully reverse cardiac fibrosis by abrogating upstream fibrogenic mechanisms, such as myofibroblast differentiation and TGF-β1 expression.

Fibrosis is often preceded by inflammation, due to infiltration of inflammatory cells during the initial phase of injury and the subsequent production of multiple cytokines. NFκB activation increases chemoattractants such as MCP-1 and ICAM-1, promoting inflammatory cell infiltration into the diseased heart whereby monocytes are differentiated into macrophages which also produce superoxide and TGF-β1 that induce myofibroblast differentiation and aggravates cardiac fibrosis. Indeed, NFκB activation is a key pro-inflammatory event that affects transcription of various ECM genes and inflammatory genes and exacerbates organ fibrosis. Importantly, AT2R stimulation dampened NFκB activation (assessed by P-IκBα expression) and tissue infiltration by macrophages (F4/80 expression). Thus, given the cross-talk between inflammatory and fibrotic pathways, it is likely that the anti-inflammatory effects caused by AT2R activation contributed to the normalization of cardiac fibrosis. At the same time, ECM is degraded by proteases such as MMPs. An AT2R agonist increased MMP-13 in the heart, suggesting that collagen degradation, together with decreased collagen synthesis, contributed to the anti-fibrotic phenotype of exemplified by AT2R stimulation.

The inventors have synthesised many combinations of β-amino acid substitutions to Ang peptides, in combination with N- and C-terminal substitutions and have provided evidence that these modifications are highly selective for AT2Rs over AT1Rs. The clinical relevance of these peptides is highlighted when considering the unmodified peptide. The endogenous peptide, Ang III, exhibits only modest selectivity for AT2R ('15-30-fold in current literature), yet it is considered as the endogenous ligand to stimulate AT2Rs in the body (Carey (2015) Adv Chronic Kidney Dis, 22: 2014-10). For example, Ang III infused directly into the kidney will promote natriuresis and diuresis, together with increased NO-cGMP levels, via AT2Rs (Padia et al., (2006) Hypertension, 47: 537-44; Padia et al., (2007) Hypertension, 49: 625-30). However, Ang III could never be used as a potential anti-fibrotic agent since it readily stimulates AT1Rs and causes marked excitatory effects such as increased blood pressure (Del Borgo et al 2015).

Therefore, it is of great interest to determine a potential threshold for AT2R selectivity, beyond which threshold a compound is likely to exert a predominant AT2R (and not AT1R) stimulatory effect in the body. In the current study, the inventors modelled this concept by investigating a range of peptide compounds with varying AT2R:AT1R selectivity for their ability to inhibit collagen production in HCFs. Given that AT2R agonists inhibit TGF-β1-mediated collagen production (FIGS. 3 and 4), the inventors determined the effects of a number of Ang peptides to inhibit collagen production. Indeed, compounds with only modest AT2R:AT1R selectivity failed to significantly reduce collagen production and only compounds with an AT2R:AT1R ratio >100 exhibited some anti-fibrotic effects in vitro. Therefore, because of the ubiquitous expression and predominant pro-fibrotic, pro-inflammatory and pro-oxidative stress effects of AT1Rs in the cardiovascular system, it likely that compounds with an AT2R:AT1R selectivity ratio of >100 may be required in vivo to avoid confounding effects of AT1R stimulation.

In conclusion, AT2R stimulation with various series of synthetic peptides derived from endogenous Ang fragments virtually abolished cardiac and renal fibrosis and symptoms of non-alcoholic fatty liver disease. These effects were often superior to those of ACE inhibition or AT1R blockade when tested in head to head comparisons. The mechanisms underlying AT2R-mediated organ protection are likely to be multifactorial. These effects include an altered balance of the ECM (decreased production and increased degradation) that favours reduced fibrosis, together with a variety of anti-inflammatory effects. Collectively, these findings suggest that AT2Rs play a key role in limiting the pathogenesis of cardiovascular disease and highlight the potential of pharmacological stimulation of AT2R as a novel therapeutic strategy, particularly for difficult-to-treat end-organ damage that occurs with aging and/or hypertension- or cardiovascular-related injury.

The invention claimed is:

1. A peptide that exhibits greater than about 100-fold selectivity for the AT2R than for the AT1R, wherein the peptide consists of:

D-Arg-Val-Tyr-Ile-His-βPro-Trp; (SEQ ID NO: 10)

N-Ac-Arg-Val-Tyr-Ile-His-βPro-Trp; (SEQ ID NO: 10)

Arg-Val-Tyr-Ile-His-βPro-Trp; (SEQ ID NO: 10)

Tetrazole-CONH-Arg-Val-Tyr-Ile-Tyr-βPro-Trp; (SEQ ID NO: 10)

Nicotinamido-Arg-Val-Tyr-Ile-His-βPro-Trp; (SEQ ID NO: 10)
or

Cholate-Arg-Val-Tyr-Ile-His-βPro-Trp. (SEQ ID NO: 10)

2. The peptide according to claim 1, wherein the peptide consists of the amino acid sequence: Arg-Val-Tyr-Ile-His-βPro-Trp (SEQ ID NO: 10).

3. The peptide according to claim 1, wherein the peptide has a half-life greater than 30 minutes in vivo.

4. A pharmaceutical composition for treating fibrosis comprising a peptide according to claim 1 and a pharmaceutically acceptable diluent, excipient or carrier.

5. The peptide of claim 1, wherein the N-terminal amino acid of the peptide is a D-amino acid, and/or the peptide is modified at the N-terminus.

6. The peptide of claim 5, wherein the peptide is modified at the N-terminus to be conjugated to one or both of a vitamin and a bile acid.

7. The peptide of claim 1, wherein the peptide is modified at the N-terminus by conjugation of Nicotinamide.

8. The peptide of claim 1, wherein the peptide is modified at the N-terminus by acetylation, N-terminal pyroglutamation, PEGylation, lipidation, glycosylation, or N-methylation.

9. The peptide of claim 1, wherein the peptide is modified at the N-terminus by capping with imidazole carboxylate or tetrazole carboxylate.

10. The peptide of claim 2, wherein the peptide is modified at the N-terminus to be conjugated to one or both of a vitamin and a bile acid.

11. The peptide of claim 2, wherein the peptide is modified at the N-terminus by conjugation of Nicotinamide.

12. The peptide of claim 2, wherein the peptide is modified at the N-terminus by acetylation, N-terminal pyroglutamation, PEGylation, lipidation, glycosylation, or N-methylation.

13. The peptide of claim 2, wherein the peptide is modified at the N-terminus by capping with imidazole carboxylate or tetrazole carboxylate.

14. A method of treating fibrosis in an individual comprising administering to the individual a peptide according to claim 1, thereby treating fibrosis in the individual.

15. A method of treating fibrosis in an individual comprising administering to the individual a peptide according to claim 2, thereby treating fibrosis in the individual.

16. The method according to claim 14, wherein the peptide exhibits an IC50 for the AT2R of less than about 100 nM, 50 nM, 20 nM, 10 nM, 9 nM, 8 nM, 7 nM, 6 nM, 5 nM, 4 nM, 3 nM, 2 nM, 1 nM and/or an IC50 for the AT1R of greater than 100 nM, 200 nM, 300 nM, 400 nM, 500 nM, 600 nM, 700 nM, 800 nM, 10 μM, or 50 μM.

17. The method according to claim 14, wherein the fibrosis is age-induced, injury-induced, stress-induced or diet-induced, or hypertension-induced, or is selected from the group consisting of cardiac fibrosis, liver fibrosis, kidney fibrosis, vascular fibrosis, lung fibrosis and dermal fibrosis.

* * * * *

SEQUENCE LISTING

<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<223> OTHER INFORMATION: Human sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 1

Xaa Xaa Val Tyr Ile Xaa Pro Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Human sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 2

Asp Arg Val Tyr Ile His Pro Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: Human sequence
<220> FEATURE:
<221> NAME/KEY: misc_feature
<222> LOCATION: (7)..(7)
<223> OTHER INFORMATION: Xaa can be any naturally occurring amino acid

<400> SEQUENCE: 3

Arg Val Tyr Ile His Pro Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: Human sequence
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Val Tyr Ile His Pro Xaa
1               5

```
<210> SEQ ID NO 5
<211> LENGTH: 8
<212> TYPE: PRT
<213> ORGANISM: Artificial Sequence
<220> FEATURE:
<223> OTHER INFORMATION: Human sequence

<400> SEQUENCE: 5

Asp Arg Val Tyr Ile His Pro Phe
1               5

<210> SEQ ID NO 6
<211> LENGTH: 7
<212> TYPE: PRT
<213> ORGANISM: Artificial Sequence
<220> FEATURE:
<223> OTHER INFORMATION: Human sequence

<400> SEQUENCE: 6

Arg Val Tyr Ile His Pro Phe
1               5

<210> SEQ ID NO 7
<211> LENGTH: 6
<212> TYPE: PRT
<213> ORGANISM: Artificial Sequence
<220> FEATURE:
<223> OTHER INFORMATION: Human sequence

<400> SEQUENCE: 7

Val Tyr Ile His Pro Phe
1               5

<210> SEQ ID NO 8
<211> LENGTH: 8
<212> TYPE: PRT
<213> ORGANISM: Artificial Sequence
<220> FEATURE:
<223> OTHER INFORMATION: Human sequence

<400> SEQUENCE: 8

Asp Arg Val Tyr Ile His Pro Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Human sequence

<400> SEQUENCE: 9

Arg Val Tyr Ile His Pro Ile
1               5

<210> SEQ ID NO 10
<211> LENGTH: 7
<212> TYPE: PRT
<213> ORGANISM: Artificial Sequence
<220> FEATURE:
<223> OTHER INFORMATION: Human sequence

<400> SEQUENCE: 10

Arg Val Tyr Ile His Pro Trp
1               5

<210> SEQ ID NO 11
```

```
<211> LENGTH: 8
<212> TYPE: PRT
<213> ORGANISM: Artificial Sequence
<220> FEATURE:
<223> OTHER INFORMATION: Human sequence

<400> SEQUENCE: 11

Asp Arg Val Tyr Ile His Pro Ala
 1               5

<210> SEQ ID NO 12
<211> LENGTH: 7
<212> TYPE: PRT
<213> ORGANISM: Artificial Sequence
<220> FEATURE:
<223> OTHER INFORMATION: Human sequence

<400> SEQUENCE: 12

Arg Val Tyr Ile His Pro Ala
 1               5

<210> SEQ ID NO 13
<211> LENGTH: 6
<212> TYPE: PRT
<213> ORGANISM: Artificial Sequence
<220> FEATURE:
<223> OTHER INFORMATION: Human sequence

<400> SEQUENCE: 13

Val Tyr Ile Tyr Pro Trp
 1               5

<210> SEQ ID NO 14
<211> LENGTH: 6
<212> TYPE: PRT
<213> ORGANISM: Artificial Sequence
<220> FEATURE:
<223> OTHER INFORMATION: Human sequence

<400> SEQUENCE: 14

Val Tyr Ile His Pro Trp
 1               5

<210> SEQ ID NO 15
<211> LENGTH: 7
<212> TYPE: PRT
<213> ORGANISM: Artificial Sequence
<220> FEATURE:
<223> OTHER INFORMATION: Human sequence

<400> SEQUENCE: 15

Arg Val Tyr Ile Tyr Pro Trp
 1               5

<210> SEQ ID NO 16
<211> LENGTH: 8
<212> TYPE: PRT
<213> ORGANISM: Artificial Sequence
<220> FEATURE:
<223> OTHER INFORMATION: Human sequence

<400> SEQUENCE: 16

Asp Arg Val Tyr Ile Tyr Pro Trp
 1               5

<210> SEQ ID NO 17
<211> LENGTH: 6
```

```
<212> TYPE: PRT
<213> ORGANISM: Artificial Sequence
<220> FEATURE:
<223> OTHER INFORMATION: Human sequence

<400> SEQUENCE: 17

Val Tyr Ile Tyr Pro Phe
1               5

<210> SEQ ID NO 18
<211> LENGTH: 7
<212> TYPE: PRT
<213> ORGANISM: Artificial Sequence
<220> FEATURE:
<223> OTHER INFORMATION: Human sequence

<400> SEQUENCE: 18

Arg Val Tyr Ile Tyr Pro Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Human sequence

<400> SEQUENCE: 19

Asp Arg Val Tyr Ile Tyr Pro Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Human sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 20

Xaa Xaa Val Tyr Ile His Pro Xaa
1               5

<210> SEQ ID NO 21
<211> LENGTH: 8
<212> TYPE: PRT
<213> ORGANISM: Artificial Sequence
<220> FEATURE:
<223> OTHER INFORMATION: Human sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 21

Xaa Arg Val Tyr Ile His Pro Xaa
1               5
```